United States Patent
Maiyuran et al.

(10) Patent No.: US 8,497,115 B2
(45) Date of Patent: Jul. 30, 2013

(54) METHODS FOR PRODUCING SECRETED POLYPEPTIDES

(75) Inventors: Suchindra Maiyuran, Gold River, CA (US); Ana Fidantsef, Davis, CA (US); Howard Brody, Davis, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 13/350,384

(22) Filed: Jan. 13, 2012

(65) Prior Publication Data

US 2012/0122191 A1     May 17, 2012

Related U.S. Application Data

(62) Division of application No. 12/135,611, filed on Jun. 9, 2008, now abandoned, which is a division of application No. 10/837,318, filed on Apr. 30, 2004, now Pat. No. 7,393,664.

(60) Provisional application No. 60/467,766, filed on May 2, 2003.

(51) Int. Cl.
*C12N 1/15* (2006.01)
*C12N 15/00* (2006.01)
*C07H 21/04* (2006.01)

(52) U.S. Cl.
USPC .................. 435/254.11; 435/320.1; 536/23.1

(58) Field of Classification Search
None
See application file for complete search history.

(56) References Cited

U.S. PATENT DOCUMENTS

| 4,435,307 A | 3/1984 | Barbesgaard et al. |
| 5,861,271 A | 1/1999 | Fowler et al. |
| 6,015,703 A | 1/2000 | White et al. |
| 6,159,720 A | 12/2000 | Murashima et al. |

FOREIGN PATENT DOCUMENTS

WO      9117243 A1      11/1991

OTHER PUBLICATIONS

Heijne Wong, A new method for predicting signal sequence cleavage sites, Nucleic Acids Research, V. 14, No. 11, 1986, pp. 4683-4690.
Margolles-Clark et al. 1996, Appl Environ Microbiol 62 (10),3840-3846.
Zeilinger et al. 1996 J Biol Chem 271 41 25624-25629.
Stangl et al. 1993, Curr Genet 23, 115-122.
Teeri et al. 1983, Biotechnol, p. 696-699.

*Primary Examiner* — Nancy T Vogel
(74) *Attorney, Agent, or Firm* — Robert L. Starnes

(57) ABSTRACT

The present invention relates to methods for producing a polypeptide, comprising: (a) cultivating a fungal host cell in a medium conducive for the production of the polypeptide, wherein the fungal host cell comprises a nucleic acid construct comprising a first nucleotide sequence encoding a signal peptide operably linked to a second nucleotide sequence encoding the polypeptide, wherein the first nucleotide sequence is foreign to the second nucleotide sequence and the 3' end of the first nucleotide sequence is immediately upstream of the initiator codon of the second nucleotide sequence. The present invention also relates to the isolated signal peptide sequences and to constructs, vectors, and fungal host cells comprising the signal peptide sequences operably linked to nucleotide sequences encoding polypeptides.

7 Claims, 22 Drawing Sheets

ATG AAG CTT GGT TGG ATC GAG GTG GCC GCA TTG GCG GCT GCC TCA GTA GTC AGT GCC
 M   K   L   G   W   I   E   V   A   A   L   A   A   A   S   V   V   S   A

Fig 8

ATG CGT TCC TCC CCC CTC CTC CGC TCC GCC GTT GTG GCC GCC CTG CCG GTG TTG GCC CTT GCC
 M   R   S   S   P   L   L   R   S   A   V   V   A   A   L   P   V   L   A   L   A

SEQUENCE LISTING

```
<160> NUMBER OF SEQ ID NOS: 64

<210> SEQ ID NO 1
<211> LENGTH: 22
<212> TYPE: DNA
<213> ORGANISM: Aspergillus oryzae

<400> SEQUENCE: 1
gtgccccatg atacgcctcc gg                                              22

<210> SEQ ID NO 2
<211> LENGTH: 26
<212> TYPE: DNA
<213> ORGANISM: Aspergillus oryzae

<400> SEQUENCE: 2
gagtcgtatt tccaaggctc ctgacc                                          26

<210> SEQ ID NO 3
<211> LENGTH: 24
<212> TYPE: DNA
<213> ORGANISM: Aspergillus oryzae

<400> SEQUENCE: 3
ggaggccatg aagtggacca acgg                                            24
```

```
<210> SEQ ID NO 4
<211> LENGTH: 45
<212> TYPE: DNA
<213> ORGANISM: Aspergillus niger

<400> SEQUENCE: 4
caccgtgaaa gccatgctct tccttcgtg tagaagacca gacag              45

<210> SEQ ID NO 5
<211> LENGTH: 45
<212> TYPE: DNA
<213> ORGANISM: Aspergillus niger

<400> SEQUENCE: 5
ctggtcttct acacgaagga aagagcatgg ctttcacggt gtctg              45

<210> SEQ ID NO 6
<211> LENGTH: 44
<212> TYPE: DNA
<213> ORGANISM: Aspergillus oryzae

<400> SEQUENCE: 6
ctatatacac aactggattt accatgggcc cgcggccgca gatc               44

<210> SEQ ID NO 7
<211> LENGTH: 44
<212> TYPE: DNA
<213> ORGANISM: Aspergillus oryzae

<400> SEQUENCE: 7
gatctgcggc cgcgggccca tggtaaatcc agttgtgtat atag               44

<210> SEQ ID NO 8
<211> LENGTH: 29
<212> TYPE: DNA
<213> ORGANISM: Trichoderma reesei

<400> SEQUENCE: 8
aacgttaatt aaggaatcgt tttgtgttt                                29

<210> SEQ ID NO 9
<211> LENGTH: 29
<212> TYPE: DNA
<213> ORGANISM: Trichoderma reesei

<400> SEQUENCE: 9
agtactagta gctccgtggc gaaagcctg                                29

<210> SEQ ID NO 10
<211> LENGTH: 31
<212> TYPE: DNA
<213> ORGANISM: Humicola insolens

<400> SEQUENCE: 10
ttgaattgaa aatagattga tttaaaactt c                             31

<210> SEQ ID NO 11
<211> LENGTH: 25
<212> TYPE: DNA
<213> ORGANISM: Humicola insolens

<400> SEQUENCE: 11
ttgcatgcgt aatcatggtc atagc                                    25
```

```
<210> SEQ ID NO 12
<211> LENGTH: 26
<212> TYPE: DNA
<213> ORGANISM: Saccharomyces cerevisiae

<400> SEQUENCE: 12
ttgaattcat gggtaataac tgatat                                          26

<210> SEQ ID NO 13
<211> LENGTH: 32
<212> TYPE: DNA
<213> ORGANISM: Saccharomyces cerevisiae

<400> SEQUENCE: 13
aaatcaatct attttcaatt caattcatca tt                                   32

<210> SEQ ID NO 14
<211> LENGTH: 45
<212> TYPE: DNA
<213> ORGANISM: Aspergillus oryzae

<400> SEQUENCE: 14
ggatgctgtt gactccggaa atttaacggt ttggtcttgc atccc                     45

<210> SEQ ID NO 15
<211> LENGTH: 44
<212> TYPE: DNA
<213> ORGANISM: Aspergillus oryzae

<400> SEQUENCE: 15
ggtattgtcc tgcagacggc aatttaacgg cttctgcgaa tcgc                      44

<210> SEQ ID NO 16
<211> LENGTH: 29
<212> TYPE: DNA
<213> ORGANISM: Humicola insolens

<400> SEQUENCE: 16
aagcttaagc atgcgttcct cccccctcc                                       29

<210> SEQ ID NO 17
<211> LENGTH: 32
<212> TYPE: DNA
<213> ORGANISM: Humicola insolens

<400> SEQUENCE: 17
ctgcagaatt ctacaggcac tgatggtacc ag                                   32

<210> SEQ ID NO 18
<211> LENGTH: 32
<212> TYPE: DNA
<213> ORGANISM: Humicola insolens

<400> SEQUENCE: 18
ctgcagaatt ctacaggcac tgatggtacc ag                                   32

<210> SEQ ID NO 19
<211> LENGTH: 36
<212> TYPE: DNA
<213> ORGANISM: Humicola insolens

<400> SEQUENCE: 19
accgcggact gcgcatcatg cgttcctccc ccctcc                               36
```

<210> SEQ ID NO 20
<211> LENGTH: 29
<212> TYPE: DNA
<213> ORGANISM: Trichoderma reesei

<400> SEQUENCE: 20
aaacgtcgac cgaatgtagg attgttatc                                29

<210> SEQ ID NO 21
<211> LENGTH: 17
<212> TYPE: DNA
<213> ORGANISM: Trichoderma reesei

<400> SEQUENCE: 21
gatgcgcagt ccgcggt                                             17

<210> SEQ ID NO 22
<211> LENGTH: 29
<212> TYPE: DNA
<213> ORGANISM: Trichoderma reesei

<400> SEQUENCE: 22
aaacgtcgac cgaatgtagg attgttatc                                29

<210> SEQ ID NO 23
<211> LENGTH: 36
<212> TYPE: DNA
<213> ORGANISM: Trichoderma reesei

<400> SEQUENCE: 23
ggagggggga ggaacgcatg atgcgcagtc cgcggt                        36

<210> SEQ ID NO 24
<211> LENGTH: 29
<212> TYPE: DNA
<213> ORGANISM: Trichoderma reesei

<400> SEQUENCE: 24
aaacgtcgac cgaatgtagg attgttatc                                29

<210> SEQ ID NO 25
<211> LENGTH: 32
<212> TYPE: DNA
<213> ORGANISM: Trichoderma reesei

<400> SEQUENCE: 25
ctgcagaatt ctacaggcac tgatggtacc ag                            32

<210> SEQ ID NO 26
<211> LENGTH: 46
<212> TYPE: DNA
<213> ORGANISM: Trichoderma reesei

<400> SEQUENCE: 26
atagtcaacc gcggactgcg catcatgaag cttggttgga tcgagg             46

<210> SEQ ID NO 27
<211> LENGTH: 26
<212> TYPE: DNA
<213> ORGANISM: Trichoderma reesei

<400> SEQUENCE: 27
actagtttac tgggccttag gcagcg                                   26

<210> SEQ ID NO 28
<211> LENGTH: 26
<212> TYPE: DNA
<213> ORGANISM: Trichoderma reesei

<400> SEQUENCE: 28
gtcgactcga agcccgaatg taggat        26

<210> SEQ ID NO 29
<211> LENGTH: 45
<212> TYPE: DNA
<213> ORGANISM: Trichoderma reesei

<400> SEQUENCE: 29
cctcgatcca accaagcttc atgatgcgca gtccgcggtt gacta        45

<210> SEQ ID NO 30
<211> LENGTH: 42
<212> TYPE: DNA
<213> ORGANISM: Aspergillus oryzae

<400> SEQUENCE: 30
tgccggtgtt ggcccttgcc aaggatgatc tcgcgtactc cc        42

<210> SEQ ID NO 31
<211> LENGTH: 28
<212> TYPE: DNA
<213> ORGANISM: Aspergillus oryzae

<400> SEQUENCE: 31
gactagtctt actgggcctt aggcagcg        28

<210> SEQ ID NO 32
<211> LENGTH: 30
<212> TYPE: DNA
<213> ORGANISM: Aspergillus oryzae

<400> SEQUENCE: 32
acgcgtcgac cgaatgtagg attgttatcc        30

<210> SEQ ID NO 33
<211> LENGTH: 42
<212> TYPE: DNA
<213> ORGANISM: Aspergillus oryzae

<400> SEQUENCE: 33
gggagtacgc gagatcatcc ttggcaaggg ccaacaccgg ca        42

<210> SEQ ID NO 34
<211> LENGTH: 57
<212> TYPE: DNA
<213> ORGANISM: Aspergillus oryzae

<400> SEQUENCE: 34
atgaagcttg gttggatcga ggtggccgca ttggcggctg cctcagtagt cagtgcc        57

<210> SEQ ID NO 35
<211> LENGTH: 19
<212> TYPE: PRT
<213> ORGANISM: Aspergillus oryzae

<400> SEQUENCE: 35

Met Lys Leu Gly Trp Ile Glu Val Ala Ala Leu Ala Ala Ala Ser Val

```
1               5                   10                  15
Val Ser Ala

<210> SEQ ID NO 36
<211> LENGTH: 63
<212> TYPE: DNA
<213> ORGANISM: Humicola insolens

<400> SEQUENCE: 36
atgcgttcct ccccccctcct ccgctccgcc gttgtggccg ccctgccggt gttggccctt      60
gcc                                                                    63

<210> SEQ ID NO 37
<211> LENGTH: 21
<212> TYPE: PRT
<213> ORGANISM: Humicola insolens

<400> SEQUENCE: 37

Met Arg Ser Ser Pro Leu Leu Arg Ser Ala Val Val Ala Ala Leu Pro
1               5                   10                  15
Val Leu Ala Leu Ala
            20

<210> SEQ ID NO 38
<211> LENGTH: 32
<212> TYPE: DNA
<213> ORGANISM: Aspergillus oryzae

<400> SEQUENCE: 38
gcagatctac catgaagctt ggttggatcg ag                                    32

<210> SEQ ID NO 39
<211> LENGTH: 30
<212> TYPE: DNA
<213> ORGANISM: Aspergillus oryzae

<400> SEQUENCE: 39
gcctcagatt actgggcctt aggcagcgag                                       30

<210> SEQ ID NO 40
<211> LENGTH: 40
<212> TYPE: DNA
<213> ORGANISM: Humicola insolens

<400> SEQUENCE: 40
aatccgacta gtggatctac catgcgttcc tccccccctcc                            40

<210> SEQ ID NO 41
<211> LENGTH: 32
<212> TYPE: DNA
<213> ORGANISM: Humicola insolens

<400> SEQUENCE: 41
gcgggcctcg agttactggg ccttaggcag cg                                    32

<210> SEQ ID NO 42
<211> LENGTH: 2586
<212> TYPE: DNA
<213> ORGANISM: Aspergillus oryzae
<220> FEATURE:
<221> NAME/KEY: CDS
<222> LOCATION: (1)..(2583)

<400> SEQUENCE: 42
```

| | | | | | | | | | | | | | | | | |
|---|---|---|---|---|---|---|---|---|---|---|---|---|---|---|---|---|
| atg | aag | ctt | ggt | tgg | atc | gag | gtg | gcc | gca | ttg | gcg | gct | gcc | tca | gta | 48 |
| Met | Lys | Leu | Gly | Trp | Ile | Glu | Val | Ala | Ala | Leu | Ala | Ala | Ala | Ser | Val | |
| 1 | | | | 5 | | | | | 10 | | | | | 15 | | |
| gtc | agt | gcc | aag | gat | gat | ctc | gcg | tac | tcc | cct | cct | ttc | tac | cct | tcc | 96 |
| Val | Ser | Ala | Lys | Asp | Asp | Leu | Ala | Tyr | Ser | Pro | Pro | Phe | Tyr | Pro | Ser | |
| | | | 20 | | | | | 25 | | | | | 30 | | | |
| cca | tgg | gca | gat | ggt | cag | ggt | gaa | tgg | gcg | gaa | gta | tac | aaa | cgc | gct | 144 |
| Pro | Trp | Ala | Asp | Gly | Gln | Gly | Glu | Trp | Ala | Glu | Val | Tyr | Lys | Arg | Ala | |
| | | 35 | | | | | 40 | | | | | 45 | | | | |
| gta | gac | ata | gtt | tcc | cag | atg | acg | ttg | aca | gag | aaa | gtc | aac | tta | acg | 192 |
| Val | Asp | Ile | Val | Ser | Gln | Met | Thr | Leu | Thr | Glu | Lys | Val | Asn | Leu | Thr | |
| | 50 | | | | | 55 | | | | | 60 | | | | | |
| act | gga | aca | gga | tgg | caa | cta | gag | agg | tgt | gtt | gga | caa | act | ggc | agt | 240 |
| Thr | Gly | Thr | Gly | Trp | Gln | Leu | Glu | Arg | Cys | Val | Gly | Gln | Thr | Gly | Ser | |
| 65 | | | | | 70 | | | | | 75 | | | | | 80 | |
| gtt | ccc | aga | ctc | aac | atc | ccc | agc | ttg | tgt | ttg | cag | gat | agt | cct | ctt | 288 |
| Val | Pro | Arg | Leu | Asn | Ile | Pro | Ser | Leu | Cys | Leu | Gln | Asp | Ser | Pro | Leu | |
| | | | | 85 | | | | | 90 | | | | | 95 | | |
| ggt | att | cgt | ttc | tcg | gac | tac | aat | tca | gct | ttc | cct | gcg | ggt | gtt | aat | 336 |
| Gly | Ile | Arg | Phe | Ser | Asp | Tyr | Asn | Ser | Ala | Phe | Pro | Ala | Gly | Val | Asn | |
| | | | 100 | | | | | 105 | | | | | 110 | | | |
| gtc | gct | gcc | acc | tgg | gac | aag | acg | ctc | gcc | tac | ctt | cgt | ggt | cag | gca | 384 |
| Val | Ala | Ala | Thr | Trp | Asp | Lys | Thr | Leu | Ala | Tyr | Leu | Arg | Gly | Gln | Ala | |
| | | 115 | | | | | 120 | | | | | 125 | | | | |
| atg | ggt | gag | gag | ttc | agt | gat | aag | ggt | att | gac | gtt | cag | ctg | ggt | cct | 432 |
| Met | Gly | Glu | Glu | Phe | Ser | Asp | Lys | Gly | Ile | Asp | Val | Gln | Leu | Gly | Pro | |
| | 130 | | | | | 135 | | | | | 140 | | | | | |
| gct | gct | ggc | cct | ctc | ggt | gct | cat | ccg | gat | ggc | ggt | aga | aac | tgg | gaa | 480 |
| Ala | Ala | Gly | Pro | Leu | Gly | Ala | His | Pro | Asp | Gly | Gly | Arg | Asn | Trp | Glu | |
| 145 | | | | | 150 | | | | | 155 | | | | | 160 | |
| ggt | ttc | tca | cca | gat | cca | gcc | ctc | acc | ggt | gta | ctt | ttt | gcg | gag | acg | 528 |
| Gly | Phe | Ser | Pro | Asp | Pro | Ala | Leu | Thr | Gly | Val | Leu | Phe | Ala | Glu | Thr | |
| | | | | 165 | | | | | 170 | | | | | 175 | | |
| att | aag | ggt | att | caa | gat | gct | ggt | gtc | att | gcg | aca | gct | aag | cat | tat | 576 |
| Ile | Lys | Gly | Ile | Gln | Asp | Ala | Gly | Val | Ile | Ala | Thr | Ala | Lys | His | Tyr | |
| | | | 180 | | | | | 185 | | | | | 190 | | | |
| atc | atg | aac | gaa | caa | gag | cat | ttc | cgc | caa | caa | ccc | gag | gct | gcg | ggt | 624 |
| Ile | Met | Asn | Glu | Gln | Glu | His | Phe | Arg | Gln | Gln | Pro | Glu | Ala | Ala | Gly | |
| | | 195 | | | | | 200 | | | | | 205 | | | | |
| tac | gga | ttc | aac | gta | agc | gac | agt | ttg | agt | tcc | aac | gtt | gat | gac | aag | 672 |
| Tyr | Gly | Phe | Asn | Val | Ser | Asp | Ser | Leu | Ser | Ser | Asn | Val | Asp | Asp | Lys | |
| | 210 | | | | | 215 | | | | | 220 | | | | | |
| act | atg | cat | gaa | ttg | tac | ctc | tgg | ccc | ttc | gcg | gat | gca | gta | cgc | gct | 720 |
| Thr | Met | His | Glu | Leu | Tyr | Leu | Trp | Pro | Phe | Ala | Asp | Ala | Val | Arg | Ala | |
| 225 | | | | | 230 | | | | | 235 | | | | | 240 | |
| gga | gtc | ggt | gct | gtc | atg | tgc | tct | tac | aac | caa | atc | aac | aac | agc | tac | 768 |
| Gly | Val | Gly | Ala | Val | Met | Cys | Ser | Tyr | Asn | Gln | Ile | Asn | Asn | Ser | Tyr | |
| | | | | 245 | | | | | 250 | | | | | 255 | | |
| ggt | tgc | gag | aat | agc | gaa | act | ctg | aac | aag | ctt | ttg | aag | gcg | gag | ctt | 816 |
| Gly | Cys | Glu | Asn | Ser | Glu | Thr | Leu | Asn | Lys | Leu | Leu | Lys | Ala | Glu | Leu | |
| | | | 260 | | | | | 265 | | | | | 270 | | | |
| ggt | ttc | caa | ggc | ttc | gtc | atg | agt | gat | tgg | acc | gct | cat | cac | agc | ggc | 864 |
| Gly | Phe | Gln | Gly | Phe | Val | Met | Ser | Asp | Trp | Thr | Ala | His | His | Ser | Gly | |
| | | 275 | | | | | 280 | | | | | 285 | | | | |
| gta | ggc | gct | gct | tta | gca | ggt | ctg | gat | atg | tcg | atg | ccc | ggt | gat | gtt | 912 |
| Val | Gly | Ala | Ala | Leu | Ala | Gly | Leu | Asp | Met | Ser | Met | Pro | Gly | Asp | Val | |
| | 290 | | | | | 295 | | | | | 300 | | | | | |
| acc | ttc | gat | agt | ggt | acg | tct | ttc | tgg | ggt | gca | aac | ttg | acg | gtc | ggt | 960 |
| Thr | Phe | Asp | Ser | Gly | Thr | Ser | Phe | Trp | Gly | Ala | Asn | Leu | Thr | Val | Gly | |
| 305 | | | | | 310 | | | | | 315 | | | | | 320 | |

```
gtc ctt aac ggt aca atc ccc caa tgg cgt gtt gac gac atg gct gtc    1008
Val Leu Asn Gly Thr Ile Pro Gln Trp Arg Val Asp Asp Met Ala Val
            325             330             335 cgt atc atg gcc gct tat tac aag gtt ggc cgc gac acc aaa tac acc    1056
Arg Ile Met Ala Ala Tyr Tyr Lys Val Gly Arg Asp Thr Lys Tyr Thr
            340             345             350 cct ccc aac ttc agc tcg tgg acc agg gac gaa tat ggt ttc gcg cat    1104
Pro Pro Asn Phe Ser Ser Trp Thr Arg Asp Glu Tyr Gly Phe Ala His
            355             360             365 aac cat gtt tcg gaa ggt gct tac gag agg gtc aac gaa ttc gtg gac    1152
Asn His Val Ser Glu Gly Ala Tyr Glu Arg Val Asn Glu Phe Val Asp
    370             375             380 gtg caa cgc gat cat gcc gac cta atc cgt cgc atc ggc gcg cag agc    1200
Val Gln Arg Asp His Ala Asp Leu Ile Arg Arg Ile Gly Ala Gln Ser
385             390             395             400 act gtt ctg ctg aag aac aag ggt gcc ttg ccc ttg agc cgc aag gaa    1248
Thr Val Leu Leu Lys Asn Lys Gly Ala Leu Pro Leu Ser Arg Lys Glu
                405             410             415 aag ctg gtc gcc ctt ctg gga gag gat gcg ggt tcc aac tcg tgg ggc    1296
Lys Leu Val Ala Leu Leu Gly Glu Asp Ala Gly Ser Asn Ser Trp Gly
            420             425             430 gct aac ggc tgt gat gac cgt ggt tgc gat aac ggt acc ctt gcc atg    1344
Ala Asn Gly Cys Asp Asp Arg Gly Cys Asp Asn Gly Thr Leu Ala Met
            435             440             445 gcc tgg ggt agc ggt act gcg aat ttc cca tac ctc gtg aca cca gag    1392
Ala Trp Gly Ser Gly Thr Ala Asn Phe Pro Tyr Leu Val Thr Pro Glu
            450             455             460 cag gcg att cag aac gaa gtt ctt cag ggc cgt ggt aat gtc ttc gcc    1440
Gln Ala Ile Gln Asn Glu Val Leu Gln Gly Arg Gly Asn Val Phe Ala
465             470             475             480 gtg acc gac agt tgg gcg ctc gac aag atc gct gcg gct gcc cgc cag    1488
Val Thr Asp Ser Trp Ala Leu Asp Lys Ile Ala Ala Ala Ala Arg Gln
                485             490             495 gcc agc gta tct ctc gtg ttc gtc aac tcc gac tca gga gaa ggc tat    1536
Ala Ser Val Ser Leu Val Phe Val Asn Ser Asp Ser Gly Glu Gly Tyr
            500             505             510 ctt agt gtg gat gga aat gag ggc gat cgt aac aac atc act ctg tgg    1584
Leu Ser Val Asp Gly Asn Glu Gly Asp Arg Asn Asn Ile Thr Leu Trp
            515             520             525 aag aac ggc gac aat gtg gtc aag acc gca gcg aat aac tgt aac aac    1632
Lys Asn Gly Asp Asn Val Val Lys Thr Ala Ala Asn Asn Cys Asn Asn
            530             535             540 acc gtt gtc atc atc cac tcc gtc gga cca gtt ttg atc gat gaa tgg    1680
Thr Val Val Ile Ile His Ser Val Gly Pro Val Leu Ile Asp Glu Trp
545             550             555             560 tat gac cac ccc aat gtc act ggt att ctc tgg gct ggt ctg cca ggc    1728
Tyr Asp His Pro Asn Val Thr Gly Ile Leu Trp Ala Gly Leu Pro Gly
            565             570             575 cag gag tct ggt aac tcc att gcc gat gtg ctg tac ggt cgt gtc aac    1776
Gln Glu Ser Gly Asn Ser Ile Ala Asp Val Leu Tyr Gly Arg Val Asn
            580             585             590 cct ggc gcc aag tct cct ttc act tgg ggc aag acc cgg gag tcg tat    1824
Pro Gly Ala Lys Ser Pro Phe Thr Trp Gly Lys Thr Arg Glu Ser Tyr
            595             600             605 ggt tct ccc ttg gtc aag gat gcc aac aat ggc aac gga gcg ccc cag    1872
Gly Ser Pro Leu Val Lys Asp Ala Asn Asn Gly Asn Gly Ala Pro Gln
            610             615             620 tct gat ttc acc cag ggt gtt ttc atc gat tac cgc cat ttc gat aag    1920
Ser Asp Phe Thr Gln Gly Val Phe Ile Asp Tyr Arg His Phe Asp Lys
625             630             635             640
```

```
ttc aat gag acc cct atc tac gag ttt ggc tac ggc ttg agc tac acc    1968
Phe Asn Glu Thr Pro Ile Tyr Glu Phe Gly Tyr Gly Leu Ser Tyr Thr
            645                 650                 655 acc ttc gag ctc tcc gac ctc cat gtt cag ccc ctg aac gcg tcc cga    2016
Thr Phe Glu Leu Ser Asp Leu His Val Gln Pro Leu Asn Ala Ser Arg
        660                 665                 670 tac act ccc acc agt ggc atg act gaa gct gca aag aac ttt ggt gaa    2064
Tyr Thr Pro Thr Ser Gly Met Thr Glu Ala Ala Lys Asn Phe Gly Glu
    675                 680                 685 att ggc gat gcg tcg gag tac gtg tat ccg gag ggg ctg gaa agg atc    2112
Ile Gly Asp Ala Ser Glu Tyr Val Tyr Pro Glu Gly Leu Glu Arg Ile
690                 695                 700 cat gag ttt atc tat ccc tgg atc aac tct acc gac ctg aag gca tcg    2160
His Glu Phe Ile Tyr Pro Trp Ile Asn Ser Thr Asp Leu Lys Ala Ser
705                 710                 715                 720 tct gac gat tct aac tac ggc tgg gaa gac tcc aag tat att ccc gaa    2208
Ser Asp Asp Ser Asn Tyr Gly Trp Glu Asp Ser Lys Tyr Ile Pro Glu
                725                 730                 735 ggc gcc acg gat ggg tct gcc cag ccc cgt ttg ccc gct agt ggt ggt    2256
Gly Ala Thr Asp Gly Ser Ala Gln Pro Arg Leu Pro Ala Ser Gly Gly
            740                 745                 750 gcc gga gga aac ccc ggt ctg tac gag gat ctt ttc cgc gtc tct gtg    2304
Ala Gly Gly Asn Pro Gly Leu Tyr Glu Asp Leu Phe Arg Val Ser Val
        755                 760                 765 aag gtc aag aac acg ggc aat gtc gcc ggt gat gaa gtt cct cag ctg    2352
Lys Val Lys Asn Thr Gly Asn Val Ala Gly Asp Glu Val Pro Gln Leu
    770                 775                 780 tac gtt tcc cta ggc ggc ccg aat gag ccc aag gtg gta ctg cgc aag    2400
Tyr Val Ser Leu Gly Gly Pro Asn Glu Pro Lys Val Val Leu Arg Lys
785                 790                 795                 800 ttt gag cgt att cac ttg gcc cct tcg cag gag gcc gtg tgg aca acg    2448
Phe Glu Arg Ile His Leu Ala Pro Ser Gln Glu Ala Val Trp Thr Thr
                805                 810                 815 acc ctt acc cgt cgt gac ctt gca aac tgg gac gtt tcg gct cag gac    2496
Thr Leu Thr Arg Arg Asp Leu Ala Asn Trp Asp Val Ser Ala Gln Asp
            820                 825                 830 tgg acc gtc act cct tac ccc aag acg atc tac gtt gga aac tcc tca    2544
Trp Thr Val Thr Pro Tyr Pro Lys Thr Ile Tyr Val Gly Asn Ser Ser
        835                 840                 845 cgg aaa ctg ccg ctc cag gcc tcg ctg cct aag gcc cag taa           2586
Arg Lys Leu Pro Leu Gln Ala Ser Leu Pro Lys Ala Gln
    850                 855                 860

<210> SEQ ID NO 43
<211> LENGTH: 861
<212> TYPE: PRT
<213> ORGANISM: Aspergillus oryzae

<400> SEQUENCE: 43

Met Lys Leu Gly Trp Ile Glu Val Ala Ala Leu Ala Ala Ala Ser Val
1               5                   10                  15

Val Ser Ala Lys Asp Asp Leu Ala Tyr Ser Pro Pro Phe Tyr Pro Ser
            20                  25                  30

Pro Trp Ala Asp Gly Gln Gly Glu Trp Ala Glu Val Tyr Lys Arg Ala
        35                  40                  45

Val Asp Ile Val Ser Gln Met Thr Leu Thr Glu Lys Val Asn Leu Thr
    50                  55                  60

Thr Gly Thr Gly Trp Gln Leu Glu Arg Cys Val Gly Gln Thr Gly Ser
65                  70                  75                  80
```

```
Val Pro Arg Leu Asn Ile Pro Ser Leu Cys Leu Gln Asp Ser Pro Leu
                85                  90                  95

Gly Ile Arg Phe Ser Asp Tyr Asn Ser Ala Phe Pro Ala Gly Val Asn
            100                 105                 110

Val Ala Ala Thr Trp Asp Lys Thr Leu Ala Tyr Leu Arg Gly Gln Ala
        115                 120                 125

Met Gly Glu Glu Phe Ser Asp Lys Gly Ile Asp Val Gln Leu Gly Pro
    130                 135                 140

Ala Ala Gly Pro Leu Gly Ala His Pro Asp Gly Gly Arg Asn Trp Glu
145                 150                 155                 160

Gly Phe Ser Pro Asp Pro Ala Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Met Asn Glu Gln Glu His Phe Arg Gln Gln Pro Glu Ala Ala Gly
        195                 200                 205

Tyr Gly Phe Asn Val Ser Asp Ser Leu Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Glu Asn Ser Glu Thr Leu Asn Lys Leu Leu Lys Ala Glu Leu
            260                 265                 270

Gly Phe Gln Gly Phe Val Met Ser Asp Trp Thr Ala His His Ser Gly
        275                 280                 285

Val Gly Ala Ala Leu Ala Gly Leu Asp Met Ser Met Pro Gly Asp Val
    290                 295                 300

Thr Phe Asp Ser Gly Thr Ser Phe Trp Gly Ala Asn Leu Thr Val Gly
305                 310                 315                 320

Val Leu Asn Gly Thr Ile Pro Gln Trp Arg Val Asp Asp Met Ala Val
                325                 330                 335

Arg Ile Met Ala Ala Tyr Tyr Lys Val Gly Arg Asp Thr Lys Tyr Thr
            340                 345                 350

Pro Pro Asn Phe Ser Ser Trp Thr Arg Asp Glu Tyr Gly Phe Ala His
        355                 360                 365

Asn His Val Ser Glu Gly Ala Tyr Glu Arg Val Asn Glu Phe Val Asp
    370                 375                 380

Val Gln Arg Asp His Ala Asp Leu Ile Arg Ile Gly Ala Gln Ser
385                 390                 395                 400

Thr Val Leu Leu Lys Asn Lys Gly Ala Leu Pro Leu Ser Arg Lys Glu
                405                 410                 415

Lys Leu Val Ala Leu Leu Gly Glu Asp Ala Gly Ser Asn Ser Trp Gly
            420                 425                 430

Ala Asn Gly Cys Asp Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
    450                 455                 460

Gln Ala Ile Gln Asn Glu Val Leu Gln Gly Arg Gly Asn Val Phe Ala
465                 470                 475                 480

Val Thr Asp Ser Trp Ala Leu Asp Lys Ile Ala Ala Ala Arg Gln
                485                 490                 495

Ala Ser Val Ser Leu Val Phe Val Asn Ser Asp Ser Gly Glu Gly Tyr
            500                 505                 510
```

```
Leu Ser Val Asp Gly Asn Glu Gly Asp Arg Asn Asn Ile Thr Leu Trp
        515                 520                 525

Lys Asn Gly Asp Asn Val Val Lys Thr Ala Ala Asn Asn Cys Asn Asn
530                 535                 540

Thr Val Val Ile Ile His Ser Val Gly Pro Val Leu Ile Asp Glu Trp
545                 550                 555                 560

Tyr Asp His Pro Asn Val Thr Gly Ile Leu Trp Ala Gly Leu Pro Gly
                565                 570                 575

Gln Glu Ser Gly Asn Ser Ile Ala Asp Val Leu Tyr Gly Arg Val Asn
            580                 585                 590

Pro Gly Ala Lys Ser Pro Phe Thr Trp Gly Lys Thr Arg Glu Ser Tyr
        595                 600                 605

Gly Ser Pro Leu Val Lys Asp Ala Asn Asn Gly Asn Gly Ala Pro Gln
    610                 615                 620

Ser Asp Phe Thr Gln Gly Val Phe Ile Asp Tyr Arg His Phe Asp Lys
625                 630                 635                 640

Phe Asn Glu Thr Pro Ile Tyr Glu Phe Gly Tyr Gly Leu Ser Tyr Thr
                645                 650                 655

Thr Phe Glu Leu Ser Asp Leu His Val Gln Pro Leu Asn Ala Ser Arg
            660                 665                 670

Tyr Thr Pro Thr Ser Gly Met Thr Glu Ala Ala Lys Asn Phe Gly Glu
        675                 680                 685

Ile Gly Asp Ala Ser Glu Tyr Val Tyr Pro Glu Gly Leu Glu Arg Ile
    690                 695                 700

His Glu Phe Ile Tyr Pro Trp Ile Asn Ser Thr Asp Leu Lys Ala Ser
705                 710                 715                 720

Ser Asp Asp Ser Asn Tyr Gly Trp Glu Asp Ser Lys Tyr Ile Pro Glu
                725                 730                 735

Gly Ala Thr Asp Gly Ser Ala Gln Pro Arg Leu Pro Ala Ser Gly Gly
            740                 745                 750

Ala Gly Gly Asn Pro Gly Leu Tyr Glu Asp Leu Phe Arg Val Ser Val
        755                 760                 765

Lys Val Lys Asn Thr Gly Asn Val Ala Gly Asp Glu Val Pro Gln Leu
    770                 775                 780

Tyr Val Ser Leu Gly Gly Pro Asn Glu Pro Lys Val Val Leu Arg Lys
785                 790                 795                 800

Phe Glu Arg Ile His Leu Ala Pro Ser Gln Glu Ala Val Trp Thr Thr
                805                 810                 815

Thr Leu Thr Arg Arg Asp Leu Ala Asn Trp Asp Val Ser Ala Gln Asp
            820                 825                 830

Trp Thr Val Thr Pro Tyr Pro Lys Thr Ile Tyr Val Gly Asn Ser Ser
        835                 840                 845

Arg Lys Leu Pro Leu Gln Ala Ser Leu Pro Lys Ala Gln
    850                 855                 860

<210> SEQ ID NO 44
<211> LENGTH: 31
<212> TYPE: DNA
<213> ORGANISM: Aspergillus fumigatus

<400> SEQUENCE: 44
actggattta ccatgagatt cggttggctc g                               31

<210> SEQ ID NO 45
<211> LENGTH: 31
```

```
<212> TYPE: DNA
<213> ORGANISM: Aspergillus fumigatus

<400> SEQUENCE: 45
agtcacctct agttactagt agacacgggg c                                    31

<210> SEQ ID NO 46
<211> LENGTH: 3060
<212> TYPE: DNA
<213> ORGANISM: Aspergillus fumigatus

<400> SEQUENCE: 46
atgagattcg gttggctcga ggtggccgct ctgacggccg cttctgtagc caatgcccag     60
gtttgtgatg ctttcccgtc attgtttcgg atatagttga caatagtcat ggaaataatc    120
aggaattggc tttctctcca ccattctacc cttcgccttg ggctgatggc cagggagagt    180
gggcagatgc ccatcgacgc gccgtcgaga tcgtttctca gatgacactg gcggagaagg    240
ttaaccttac aacgggtact gggtgggttg cgactttttt gttgacagtg agctttcttc    300
actgaccatc tacacagatg gaaatggac cgatgcgtcg gtcaaaccgg cagcgttccc     360
aggtaagctt gcaattctgc aacaacgtgc aagtgtagtt gctaaaacgc ggtggtgcag    420
acttggtatc aactggggtc tttgtggcca ggattcccct ttgggtatcc gtttctgtga    480
gctatacccg cggagtcttt cagtccttgt attatgtgct gatgattgtc tctgtatagc    540
tgacctcaac tccgccttcc ctgctggtac taatgtcgcc gcgacatggg acaagacact    600
cgcctacctt cgtggcaagg ccatgggtga ggaattcaac gacaagggcg tggacatttt    660
gctggggcct gctgctggtc ctctcggcaa atacccggac ggcggcagaa tctgggaagg    720
cttctctcct gatccggttc tcactggtgt acttttcgcc gaaactatca agggtatcca    780
agacgcgggt gtgattgcta ctgccaagca ttacattctg aatgaacagg agcatttccg    840
acaggttggc gaggcccagg atatggttaa catcacg gagacgatca gctccaacgt       900
ggatgacaag accatgcacg agttgtacct tggtgagta gttgacactg caaatgagga    960
ccttgattga tttgactgac ctggaatgca ggccccttgc agatgctgtg cgcggtaaga   1020
ttttccgtag acttgacctc gcgacgaaga atcgctgac gaaccatcgt agctggcgtt    1080
ggcgctgtca tgtgttccta caatcaaatc aacaacagct acggttgtca aaacagtcaa   1140
actctcaaca agctcctcaa ggctgagctg ggcttccaag gcttcgtcat gagtgactgg   1200
agcgctcacc acagcggtgt cggcgctgcc ctcgctgggt tggatatgtc gatgcctgga   1260
gacatttcct tcgacgacgg actctccttc tggggcacga acctaactgt cagtgttctt   1320
aacggcaccg ttccagcctg gcgtgtcgat gacatggctg ttcgtatcat gaccgcgtac   1380
tacaaggttg gtcgtgaccg tcttcgtatt ccccctaact tcagctcctg gaccgggat    1440 gagtacggct gggagcattc tgctgtctcc gagggagcct ggaccaaggt gaacgacttc   1500
gtcaatgtgc agcgcagtca ctctcagatc atccgtgaga ttggtgccgc tagtacagtg   1560
ctcttgaaga acacgggtgc tcttcctttg accggcaagg aggttaaagt gggtgttctc   1620
ggtgaagacg ctggttccaa cccgtgggt gctaacggct gccccgaccg cggctgtgat    1680
aacggcactc ttgctatggc ctggggtagt ggtactgcca acttcccta ccttgtcacc    1740 cccgagcagg ctatccagcg agaggtcatc agcaacggcg gcaatgtctt tgctgtgact   1800
gataacgggg ctctcagcca gatggcagat gttgcatctc aatccaggtg agtgcgggct   1860
cttagaaaaa gaacgttctc tgaatgaagt tttttaacca ttgcgaacag cgtgtctttg   1920
gtgtttgtca acgccgactc tggagagggt ttcatcagtg tcgacggcaa cgagggtgac   1980
```

```
cgcaaaaatc tcactctgtg aagaacggc gaggccgtca ttgacactgt tgtcagccac    2040
tgcaacaaca cgattgtggt tattcacagt gttgggcccg tcttgatcga ccggtggtat    2100
gataacccca acgtcactgc catcatctgg gccggcttgc ccggtcagga gagtggcaac    2160
tccctggtcg acgtgctcta tggccgcgtc aaccccagcg ccaagacccc gttcacctgg    2220
ggcaagactc gggagtctta cggggctccc ttgctcaccg agcctaacaa tggcaatggt    2280
gctccccagg atgatttcaa cgagggcgtc ttcattgact accgtcactt tgacaagcgc    2340
aatgagaccc ccatttatga gtttggccat ggcttgagct acaccacctt tggttactct    2400
caccttcggg ttcaggccct caatagttcg agttcggcat atgtcccgac tagcggagag    2460
accaagcctg cgccaaccta tggtgagatc ggtagtgccg ccgactacct gtatcccgag    2520
ggtctcaaaa gaattaccaa gtttatttac ccttggctca actcgaccga cctcgaggat    2580
tcttctgacg acccgaacta cggctgggag gactcggagt acattcccga aggcgctagg    2640
gatgggtctc ctcaaccct cctgaaggct ggcggcgctc tggtggtaa ccctacccctt    2700 tatcaggatc ttgttagggt gtcggccacc ataaccaaca ctggtaacgt cgccggttat    2760
gaagtccctc aattggtgag tgacccgcat gttccttgcg ttgcaatttg gctaactcgc    2820
ttctagtatg tttcactggg cggaccgaac gagcctcggg tcgttctgcg caagttcgac    2880
cgaatcttcc tggctcctgg ggagcaaaag gtttggacca cgactcttaa ccgtcgtgat    2940
ctcgccaatt gggatgtgga ggctcaggac tgggtcatca caaagtaccc caagaaagtg    3000
cacgtcggca gctcctcgcg taagctgcct ctgagagcgc tctgccccg tgtctactag    3060
```

<210> SEQ ID NO 47
<211> LENGTH: 863
<212> TYPE: PRT
<213> ORGANISM: Aspergillus fumigatus

<400> SEQUENCE: 47

```
Met Arg Phe Gly Trp Leu Glu Val Ala Ala Leu Thr Ala Ala Ser Val
1               5                  10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
    130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190
```

```
Ile Leu Asn Glu Gln Glu His Phe Arg Gln Val Gly Glu Ala Gln Gly
            195                 200                 205

Tyr Gly Tyr Asn Ile Thr Glu Thr Ile Ser Ser Asn Val Asp Asp Lys
            210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
            260                 265                 270

Gly Phe Gln Gly Phe Val Met Ser Asp Trp Ser Ala His His Ser Gly
            275                 280                 285

Val Gly Ala Ala Leu Ala Gly Leu Asp Met Ser Met Pro Gly Asp Ile
            290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
            325                 330                 335

Arg Ile Met Thr Ala Tyr Tyr Lys Val Gly Arg Asp Arg Leu Arg Ile
            340                 345                 350

Pro Pro Asn Phe Ser Ser Trp Thr Arg Asp Glu Tyr Gly Trp Glu His
            355                 360                 365

Ser Ala Val Ser Glu Gly Ala Trp Thr Lys Val Asn Asp Phe Val Asn
            370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
            405                 410                 415

Val Lys Val Gly Val Leu Gly Glu Asp Ala Gly Ser Asn Pro Trp Gly
            420                 425                 430

Ala Asn Gly Cys Pro Asp Arg Gly Cys Asp Asn Gly Thr Leu Ala Met
            435                 440                 445

Ala Trp Gly Ser Gly Thr Ala Asn Phe Pro Tyr Leu Val Thr Pro Glu
            450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
            485                 490                 495

Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
            515                 520                 525

Lys Asn Gly Glu Ala Val Ile Asp Thr Val Val Ser His Cys Asn Asn
530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
            595                 600                 605

Gly Ala Pro Leu Leu Thr Glu Pro Asn Asn Gly Asn Gly Ala Pro Gln
```

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
            645                 650                 655

Thr Phe Gly Tyr Ser His Leu Arg Val Gln Ala Leu Asn Ser Ser Ser
                660                 665                 670

Ser Ala Tyr Val Pro Thr Ser Gly Glu Thr Lys Pro Ala Pro Thr Tyr
            675                 680                 685

Gly Glu Ile Gly Ser Ala Ala Asp Tyr Leu Tyr Pro Glu Gly Leu Lys
690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
            755                 760                 765

Ser Ala Thr Ile Thr Asn Thr Gly Asn Val Ala Gly Tyr Glu Val Pro
770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
            835                 840                 845

Ser Ser Arg Lys Leu Pro Leu Arg Ala Pro Leu Pro Arg Val Tyr
        850                 855                 860

<210> SEQ ID NO 48
<211> LENGTH: 2592
<212> TYPE: DNA
<213> ORGANISM: Aspergillus fumigatus

<400> SEQUENCE: 48
atgagattcg gttggctcga ggtggccgct ctgacggccg cttctgtagc caatgcccag      60
gaattggctt tctctccacc attctaccct tcgccttggg ctgatggcca gggagagtgg     120
gcagatgccc atcgacgcgc cgtcgagatc gtttctcaga tgacactggc ggagaaggtt     180
aaccttacaa cgggtactgg atgggaaatg gaccgatgcg tcggtcaaac cggcagcgtt     240
cccagacttg gtatcaactg ggtctttgt ggccaggatt ccctttgg tatccgtttc       300 tctgacctca actccgcctt ccctgctggt actaatgtcg ccgcgacatg ggacaagaca     360
ctcgcctacc ttcgtggcaa ggccatgggt gaggaattca cgacaaggg cgtggacatt      420 ttgctggggc ctgctgctgg tcctctcggc aaataccgg acggcggcag aatctgggaa      480
ggcttctctc ctgatccggt tctcactggt gtactttcg ccgaaactat caagggtatc      540
caagacgcgg gtgtgattgc tactgccaag cattacattc tgaatgaaca ggagcatttc     600
cgacaggttg gcgaggccca gggatatggt tacaacatca ggagacgat cagctccaac     660 gtggatgaca gaccatgca cgagttgtac ctttggccct tgcagatgc tgtgcgcgct     720 ggcgttggcg ctgtcatgtg ttcctacaat caaatcaaca acagctacgg ttgtcaaaac    780

```
agtcaaactc tcaacaagct cctcaaggct gagctgggct tccaaggctt cgtcatgagt    840
gactggagcg ctcaccacag cggtgtcggc gctgccctcg ctgggttgga tatgtcgatg    900
cctggagaca tttccttcga cgacggactc tccttctggg cacgaacct aactgtcagt    960
gttcttaacg caccgttcc agcctggcgt gtcgatgaca tggctgttcg tatcatgacc   1020
gcgtactaca aggttggtcg tgaccgtctt cgtattcccc ctaacttcag ctcctggacc   1080
cgggatgagt acggctggga gcattctgct gtctccgagg agcctggac caaggtgaac   1140
gacttcgtca atgtgcagcg cagtcactct cagatcatcc gtgagattgg tgccgctagt   1200
acagtgctct tgaagaacac gggtgctctt cctttgaccg gcaaggaggt taaagtgggt   1260
gttctcggtg aagacgctgg ttccaacccg tggggtgcta acggctgccc cgaccgcggc   1320
tgtgataacg gcactcttgc tatggcctgg ggtagtggta ctgccaactt cccttacctt   1380
gtcaccccg agcaggctat ccagcgagag gtcatcagca acggcggcaa tgtctttgct   1440
gtgactgata cggggctct cagccagatg gcagatgttg catctcaatc cagcgtgtct   1500
ttggtgtttg tcaacgccga ctctggagag ggtttcatca gtgtcgacgg caacgagggt   1560
gaccgcaaaa atctcactct gtggaagaac ggcgaggccg tcattgacac tgttgtcagc   1620
cactgcaaca acacgattgt ggttattcac agtgttgggc cgtcttgat cgaccggtgg   1680
tatgataacc ccaacgtcac tgccatcatc tgggccggct tgcccggtca ggagagtggc   1740
aactccctgg tcgacgtgct ctatggccgc gtcaaccca gcgccaagac cccgttcacc   1800
tggggcaaga ctcgggagtc ttacgggct cccttgctca ccgagcctaa caatggcaat   1860
ggtgctcccc aggatgattt caacgagggc gtcttcattg actaccgtca ctttgacaag   1920
cgcaatgaga cccccattta tgagtttggc catggcttga gctacaccac ctttggttac   1980
tctcaccttc gggttcaggc cctcaatagt tcgagttcgg catatgtccc gactagcgga   2040
gagaccaagc ctgcgccaac ctatggtgag atcggtagtg ccgccgacta cctgtatccc   2100
gagggtctca aaagaattac caagtttatt taccccttggc tcaactcgac cgacctcgag   2160
gattcttctg acgacccgaa ctacggctgg gaggactcgg agtacattcc cgaaggcgct   2220
agggatgggt ctcctcaacc cctcctgaag gctggcggcg ctcctggtgg taaccctacc   2280
ctttatcagg atcttgttag ggtgtcggcc accataacca acactggtaa cgtcgccggt   2340
tatgaagtcc ctcaattgta tgtttcactg ggcggaccga acgagcctcg ggtcgttctg   2400
cgcaagttcg accgaatctt cctggctcct ggggagcaaa aggtttggac cacgactctt   2460
aaccgtcgtg atctcgccaa ttgggatgtg gaggctcagg actgggtcat cacaaagtac   2520
cccaagaaag tgcacgtcgg cagctcctcg cgtaagctgc ctctgagagc gcctctgccc   2580
cgtgtctact ag                                                      2592
```

<210> SEQ ID NO 49
<211> LENGTH: 863
<212> TYPE: PRT
<213> ORGANISM: Aspergillus fumigatus

<400> SEQUENCE: 49

Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

-continued

```
Glu Ile Val Ser Gln Met Thr Leu Ala Glu Lys Val Asn Leu Thr Thr
 50                  55                  60

Gly Thr Gly Trp Glu Met Asp Arg Cys Val Gln Thr Gly Ser Val
 65                  70                  75                  80

Pro Arg Leu Gly Ile Asn Trp Gly Leu Cys Gly Gln Asp Ser Pro Leu
                 85                  90                  95

Gly Ile Arg Phe Ser Asp Leu Asn Ser Ala Phe Pro Ala Gly Thr Asn
                100                 105                 110

Val Ala Ala Thr Trp Asp Lys Thr Leu Ala Tyr Leu Arg Gly Lys Ala
                115                 120                 125

Met Gly Glu Glu Phe Asn Asp Lys Gly Val Asp Ile Leu Leu Gly Pro
130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
                180                 185                 190

Ile Leu Asn Glu Gln Glu His Phe Arg Gln Val Gly Glu Ala Gln Gly
                195                 200                 205

Tyr Gly Tyr Asn Ile Thr Glu Thr Ile Ser Ser Asn Val Asp Asp Lys
210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
                260                 265                 270

Gly Phe Gln Gly Phe Val Met Ser Asp Trp Ser Ala His His Ser Gly
                275                 280                 285

Val Gly Ala Ala Leu Ala Gly Leu Asp Met Ser Met Pro Gly Asp Ile
                290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
                340                 345                 350

Pro Pro Asn Phe Ser Ser Trp Thr Arg Asp Glu Tyr Gly Trp Glu His
                355                 360                 365

Ser Ala Val Ser Glu Gly Ala Trp Thr Lys Val Asn Asp Phe Val Asn
370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
                420                 425                 430

Ala Asn Gly Cys Pro Asp Arg Gly Cys Asp Asn Gly Thr Leu Ala Met
                435                 440                 445

Ala Trp Gly Ser Gly Thr Ala Asn Phe Pro Tyr Leu Val Thr Pro Glu
450                 455                 460

Gln Ala Ile Gln Arg Glu Val Ile Ser Asn Gly Gly Asn Val Phe Ala
465                 470                 475                 480
```

Val Thr Asp Asn Gly Ala Leu Ser Gln Met Ala Asp Val Ala Ser Gln
            485                 490                 495

Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
            515                 520                 525

Lys Asn Gly Glu Ala Val Ile Asp Thr Val Val Ser His Cys Asn Asn
530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
            595                 600                 605

Gly Ala Pro Leu Leu Thr Glu Pro Asn Asn Gly Asn Gly Ala Pro Gln
            610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
            675                 680                 685

Gly Glu Ile Gly Ser Ala Ala Asp Tyr Leu Tyr Pro Glu Gly Leu Lys
            690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
            755                 760                 765

Ser Ala Thr Ile Thr Asn Thr Gly Asn Val Ala Gly Tyr Glu Val Pro
770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
            835                 840                 845

Ser Ser Arg Lys Leu Pro Leu Arg Ala Pro Leu Pro Arg Val Tyr
            850                 855                 860

<210> SEQ ID NO 50
<211> LENGTH: 29
<212> TYPE: DNA
<213> ORGANISM: Aspergillus fumigatus

<400> SEQUENCE: 50

```
ggctcatgag attcggttgg ctcgaggtc                                      29

<210> SEQ ID NO 51
<211> LENGTH: 30
<212> TYPE: DNA
<213> ORGANISM: Aspergillus fumigatus

<400> SEQUENCE: 51
gccgttatca cagccgcggt cggggcagcc                                     30

<210> SEQ ID NO 52
<211> LENGTH: 30
<212> TYPE: DNA
<213> ORGANISM: Aspergillus fumigatus

<400> SEQUENCE: 52
ggctgccccg accgcggctg tgataacggc                                     30

<210> SEQ ID NO 53
<211> LENGTH: 35
<212> TYPE: DNA
<213> ORGANISM: Aspergillus fumigatus

<400> SEQUENCE: 53
gcttaattaa tctagtagac acggggcaga ggcgc                               35

<210> SEQ ID NO 54
<211> LENGTH: 16
<212> TYPE: DNA
<213> ORGANISM: Aspergillus fumigatus

<400> SEQUENCE: 54
acactggcgg agaagg                                                    16

<210> SEQ ID NO 55
<211> LENGTH: 18
<212> TYPE: DNA
<213> ORGANISM: Aspergillus fumigatus

<400> SEQUENCE: 55
gcccagggat atggttac                                                  18

<210> SEQ ID NO 56
<211> LENGTH: 19
<212> TYPE: DNA
<213> ORGANISM: Aspergillus fumigatus

<400> SEQUENCE: 56
cgactctgga gagggtttc                                                 19

<210> SEQ ID NO 57
<211> LENGTH: 19
<212> TYPE: DNA
<213> ORGANISM: Aspergillus fumigatus

<400> SEQUENCE: 57
ggactgggtc atcacaaag                                                 19

<210> SEQ ID NO 58
<211> LENGTH: 17
<212> TYPE: DNA
<213> ORGANISM: Aspergillus fumigatus

<400> SEQUENCE: 58
```

-continued

```
gcgagaggtc atcagca                                                    17

<210> SEQ ID NO 59
<211> LENGTH: 17
<212> TYPE: DNA
<213> ORGANISM: Aspergillus fumigatus

<400> SEQUENCE: 59
gtaaaacgac ggccagt                                                    17

<210> SEQ ID NO 60
<211> LENGTH: 16
<212> TYPE: DNA
<213> ORGANISM: Aspergillus fumigatus

<400> SEQUENCE: 60
caggaaacag ctatga                                                     16

<210> SEQ ID NO 61
<211> LENGTH: 69
<212> TYPE: DNA
<213> ORGANISM: Aspergillus fumigatus

<400> SEQUENCE: 61
cttcttgtta gtgcaatatc atatagaagt catcgactag tggatctacc atgagattcg    60
gttggctcg                                                             69

<210> SEQ ID NO 62
<211> LENGTH: 61
<212> TYPE: DNA
<213> ORGANISM: Aspergillus fumigatus

<400> SEQUENCE: 62
gcgtgaatgt aagcgtgaca taactaatta catgactcga gctagtagac acggggcaga    60
g                                                                     61

<210> SEQ ID NO 63
<211> LENGTH: 60
<212> TYPE: DNA
<213> ORGANISM: Aspergillus fumigatus

<400> SEQUENCE: 63
ccgctccgcc gttgtggccg ccctgccggt gttggccctt gccgaattgg ctttctctcc    60

<210> SEQ ID NO 64
<211> LENGTH: 17
<212> TYPE: DNA
<213> ORGANISM: Aspergillus fumigatus

<400> SEQUENCE: 64
ctggcgttgg cgctgtc                                                    17
```

METHODS FOR PRODUCING SECRETED POLYPEPTIDES

CROSS-REFERENCE TO RELATED APPLICATION

This application is a divisional of U.S. application Ser. No. 12/135,611, filed Jun. 9, 2008, which is a divisional of U.S. application Ser. No. 10/837,318, filed Apr. 30, 2004, which claims the benefit of U.S. Provisional Application No. 60/467,766, filed May 2, 2003, which applications are incorporated herein by reference.

STATEMENT AS TO RIGHTS TO INVENTIONS MADE UNDER FEDERALLY SPONSORED RESEARCH AND DEVELOPMENT

This invention was made with Government support under NREL Subcontract No. ZCO-30017-02, Prime Contract DE-AC36-98GO10337 awarded by the Department of Energy. The government has certain rights in this invention,

BACKGROUND OF THE INVENTION

1. Field of the Invention

The present invention relates to methods for producing secreted polypeptides. The present invention also relates to isolated nucleotide sequences encoding signal peptides and nucleic acid constructs, vectors, and host cells comprising the signal peptide sequences operably linked to nucleotide sequences encoding polypeptides.

2. Description of the Related Art

The recombinant production of a heterologous protein in a fungal host cell, particularly a filamentous fungal cell such as *Aspergillus* or a yeast cell such *Saccharomyces*, may provide for a more desirable vehicle for producing the protein in commercially relevant quantities.

Recombinant production of a heterologous protein is generally accomplished by constructing an expression cassette in which the DNA coding for the protein is placed under the expression control of a promoter, excised from a regulated gene, suitable for the host cell. The expression cassette is introduced into the host cell, usually by plasmid-mediated transformation. Production of the heterologous protein is then achieved by culturing the transformed host cell under inducing conditions necessary for the proper functioning of the promoter contained on the expression cassette.

Improvement of the recombinant production of proteins generally requires the availability of new regulatory sequences which are suitable for controlling the expression of the proteins in a host cell.

U.S. Pat. No. 6,015,703 discloses genetic constructs comprising a promoter, a xylanase secretion signal, and a mature beta-glucosidase coding region. The disclosed constructs, when expressed in recombinant microbes, dramatically increase the amount of beta-glucosidase produced relative to untransformed microbes.

WO 91/17243 discloses an endoglucanase V and the gene thereof from *Humicola insolens* DSM 1800.

It is an object of the present invention to provide improved methods for producing a polypeptide in a fungal host cell using signal peptide sequences.

SUMMARY OF THE INVENTION

The present invention relates to methods for producing a secreted polypeptide, comprising:

(a) cultivating a fungal host cell in a medium conducive for the production of the polypeptide, wherein the fungal host cell comprises a nucleic acid construct comprising a first nucleotide sequence encoding a signal peptide operably linked to a second nucleotide sequence encoding the polypeptide, wherein the first nucleotide sequence is foreign to the second nucleotide sequence, the 3' end of the first nucleotide sequence is immediately upstream of the initiator codon of the second nucleotide sequence, and the first nucleotide sequence is selected from the group consisting of:
  (i) a nucleotide sequence encoding a signal peptide having an amino acid sequence which has at least 70% identity with SEQ ID NO: 37;
  (ii) a nucleotide sequence having at least 70% homology with SEQ ID NO: 36; and
  (iii) a nucleotide sequence which hybridizes under stringency conditions with the nucleotides of SEQ ID NO: 36, or its complementary strand, wherein the stringency conditions are defined as prehybridization, hybridization, and washing post-hybridization at 5° C. to 10° C. below the calculated $T_m$ in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml, and washing once in 6×SCC plus 0.1% SDS for 15 minutes and twice each for 15 minutes using 6×SSC at 5° C. to 10° C. below the calculated $T_m$; and
(b) isolating the secreted polypeptide from the cultivation medium.

The present invention also relates to isolated signal peptide sequences and to constructs, vectors, and fungal host cells comprising the signal peptide sequences operably linked to nucleotide sequences encoding polypeptides.

BRIEF DESCRIPTION OF THE FIGURES

FIG. 8 shows the DNA sequence (SEQ ID NO: 34) and deduced amino acid sequence (SEQ ID NO: 35) of the secretion signal sequence of an *Aspergillus orzae* beta-glucosidase.
FIG. 9 shows the DNA sequence (SEQ ID NO: 36) and deduced amino acid sequence (SEQ ID NO: 37) of the secretion signal sequence of a *Humicola insolens* endoglucanase V.
FIG. 16 shows the genomic DNA sequence and the deduced amino acid sequence of an *Aspergillus fumigatus* beta-glucosidase (SEQ ID NOS: 46 and 47, respectively). The predicted signal peptide is underlined and predicted introns are italicized.

DETAILED DESCRIPTION OF THE INVENTION

Figure 1:
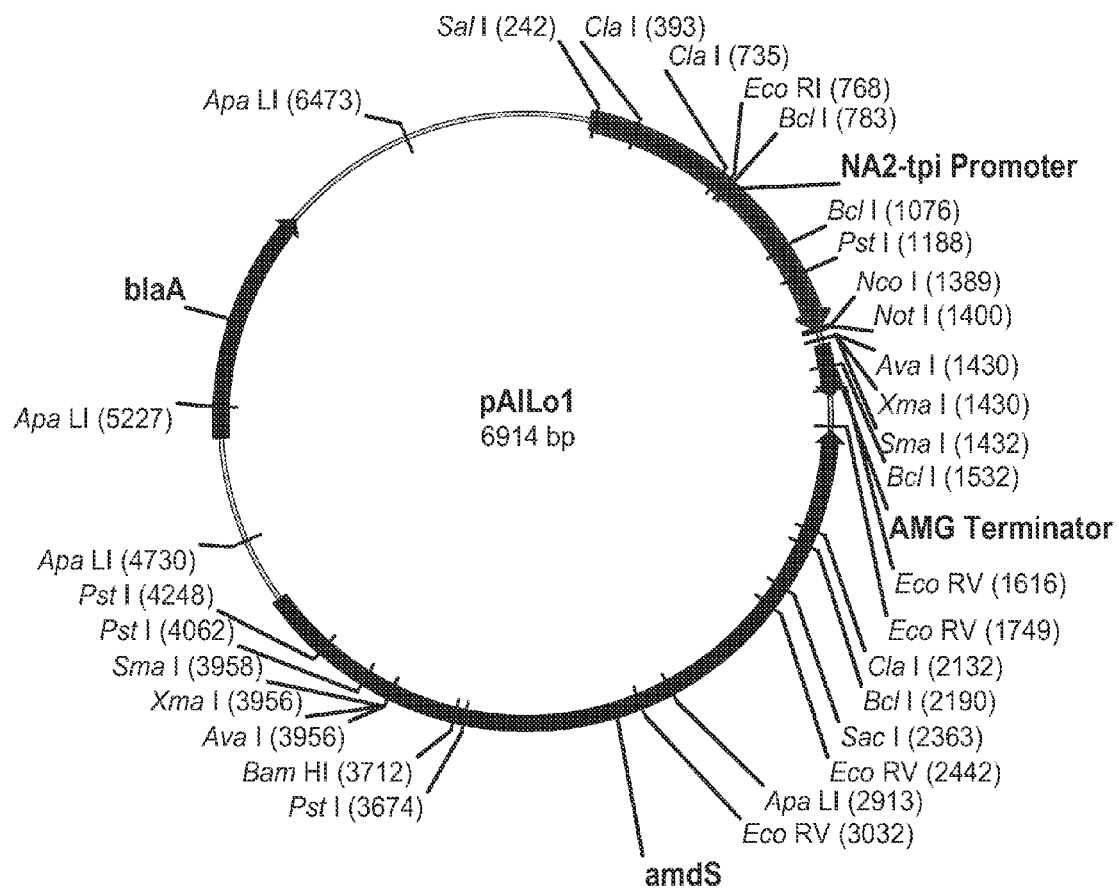
FIG. 1 shows a restriction map of pAlLo1.

The present invention relates to methods for producing a polypeptide, comprising: (a) cultivating a fungal host cell in a medium conducive for the production of the polypeptide, wherein the fungal host cell comprises a nucleic acid construct comprising a first nucleotide sequence encoding a signal peptide operably linked to a second nucleotide sequence encoding the polypeptide, wherein the first nucleotide sequence is foreign to the second nucleotide sequence and the 3' end of the first nucleotide sequence is immediately upstream of the initiator codon of the second nucleotide sequence. The first nucleotide sequence is selected from the group consisting of: (i) a nucleotide sequence encoding a signal peptide having an amino acid sequence which has at least 70% identity with SEQ ID NO: 37; (ii) a nucleotide sequence having at least 70% homology with SEQ ID NO: 36; and (iii) a nucleotide sequence which hybridizes under stringency conditions with the nucleotides of SEQ ID NO: 36, or its complementary strand, wherein the stringency conditions are defined as prehybridization, hybridization, and washing post-hybridization at 5° C. to 10° C. below the calculated $T_m$ in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml, and washing once in 6×SCC plus 0.1% SDS for 15 minutes and twice each for 15 minutes using 6×SSC at 5° C. to 10° C. below the calculated $T_m$; and (b) isolating the secreted polypeptide from the cultivation medium.

In the production methods of the present invention, the fungal host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection).

The polypeptides may be detected using methods known in the art that are specific for the polypeptides. These detection methods may include use of specific antibodies, formation of an enzyme product, or disappearance of an enzyme substrate.

In the methods of the present invention, the fungal cell preferably produces at least about 25% more, more preferably at least about 50% more, more preferably at least about 75% more, more preferably at least about 100% more, even more preferably at least about 200% more, most preferably at least about 300% more, and even most preferably at least about 400% more polypeptide relative to a fungal cell containing a native signal peptide sequence operably linked to a nucleotide sequence encoding the polypeptide when cultured under identical production conditions.

The resulting secreted polypeptide can be recovered directly from the medium by methods known in the art. For example, the polypeptide may be recovered from the nutrient medium by conventional procedures including, but not limited to, centrifugation, filtration, extraction, spray-drying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Signal Peptide Sequences

The term "signal peptide sequence" is defined herein as a peptide coding region that codes for an amino acid sequence linked to the amino terminus of a polypeptide and directs the encoded polypeptide into the cell's secretory pathway.

The term "operably linked" is defined herein as a configuration in which a control sequence, e.g., a signal peptide sequence, is appropriately placed at a position relative to a coding sequence such that the control sequence directs the production of a polypeptide encoded by the coding sequence.

The term "coding sequence" is defined herein as a nucleotide sequence that is transcribed into mRNA which is translated into a polypeptide when placed under the control of the appropriate control sequences. The boundaries of the coding sequence are generally determined by the start codon located at the beginning of the open reading frame of the 5' end of the mRNA and a stop codon located at the 3' end of the open reading frame of the mRNA. A coding sequence can include, but is not limited to, genomic DNA, cDNA, semisynthetic, synthetic, and recombinant nucleotide sequences.

The 5' end of the polypeptide coding sequence may contain a native signal peptide coding region naturally linked in translation reading frame with the segment of the coding region which encodes the polypeptide, wherein the signal peptide coding region of the present invention may simply replace the natural signal peptide coding region in order to enhance secretion of the polypeptide. Alternatively, the 5' end of the polypeptide coding sequence may lack a native signal peptide coding region.

In the methods of the present invention, the signal peptide sequence is foreign to the nucleotide sequence encoding a polypeptide of interest, but the signal peptide sequence or nucleotide sequence may be native to the fungal host cell.

In a first aspect, the isolated nucleotide sequences encoding a signal peptide have a degree of identity to SEQ ID NO: 37 of at least about 70%, preferably at least about 75%, more preferably at least about 80%, more preferably at least about 85%, even more preferably at least about 90%, most preferably at least about 95%, and even most preferably at least about 97%, which have the ability to direct a polypeptide into a cell's secretory pathway (hereinafter "homologous signal peptides"). In a preferred aspect, the homologous signal peptides have an amino acid sequence which differs by five amino acids, preferably by four amino acids, more preferably by three amino acids, even more preferably by two amino acids, and most preferably by one amino acid from SEQ ID NO: 37. For purposes of the present invention, the degree of identity between two amino acid sequences is determined by the Clustal method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

Preferably, the nucleotide sequences encode signal peptides that comprise the amino acid sequence of SEQ ID NO: 37, or allelic variants thereof; or fragments thereof that have the ability to direct the polypeptide into a cell's secretory pathway. In a more preferred aspect, a nucleotide sequence of the present invention encodes a signal peptide that comprises the amino acid sequence of SEQ ID NO: 37. In another preferred aspect, the nucleotide sequence encodes a signal peptide that consists of the amino acid sequence of SEQ ID NO: 37, or a fragment thereof, wherein the signal peptide fragment has the ability to direct a polypeptide into a cell's secretory pathway. In another more preferred aspect, the nucleotide sequence of the present invention encodes a signal peptide that consists of the amino acid sequence of SEQ ID NO: 37.

The present invention also encompasses nucleotide sequences which encode a signal peptide having the amino acid sequence of SEQ ID NO: 37, which differ from SEQ ID NO: 36 bp virtue of the degeneracy of the genetic code. The present invention also relates to subsequences of SEQ ID NO: 36 which encode fragments of SEQ ID NO: 37 which have the ability to direct a polypeptide into a cell's secretory pathway.

A subsequence of SEQ ID NO: 36 is a nucleic acid sequence encompassed by SEQ ID NO: 36 except that one or more nucleotides from the 5' and/or 3' end have been deleted. Preferably, a subsequence contains at least 45 nucleotides, more preferably at least 51 nucleotides, and most preferably at least 57 nucleotides. A fragment of SEQ ID NO: 37 is a polypeptide having one or more amino acids deleted from the amino and/or carboxy terminus of this amino acid sequence. Preferably, a fragment contains at least 15 amino acid residues, more preferably at least 17 amino acid residues, and most preferably at least 19 amino acid residues.

An allelic variant denotes any of two or more alternative forms of a gene occupying the same chomosomal locus. Allelic variation arises naturally through mutation, and may result in polymorphism within populations. Gene mutations can be silent (no change in the encoded signal peptide) or may encode signal peptides having altered amino acid sequences. The allelic variant of a signal peptide is a peptide encoded by an allelic variant of a gene.

In a preferred aspect, the first nucleotide sequence is the signal peptide coding sequence of the endoglucanase V gene contained in *Humicola insolens* DSM 1800.

In a second aspect, the isolated nucleic acid sequences encoding a signal peptide have a degree of homology to SEQ ID NO: 36 of at least about 70%, preferably at least about 75%, more preferably at least about 80%, more preferably at least about 85%, even more preferably at least about 90% homology, most preferably at least about 95% homology, and even most preferably at least about 97% homology, which encode a signal peptide; or allelic variants and subsequences of SEQ ID NO: 36 which encode signal peptide fragments which have the ability to direct a polypeptide into a cell's secretory pathway. For purposes of the present invention, the degree of homology between two nucleic acid sequences is determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

In a third aspect, the isolated nucleotide sequences encode signal peptides, wherein the nucleotide sequences hybridize under stringency conditions with the nucleotides of SEQ ID NO: 36, or its complementary strand (J. Sambrook, E. F. Fritsch, and T. Maniatus, 1989, *Molecular Cloning, A Laboratory Manual*, 2d edition, Cold Spring Harbor, N.Y.).

The nucleotide sequence of SEQ ID NO: 36 or a subsequence thereof, as well as the amino acid sequence of SEQ ID NO: 37 or a fragment thereof, may be used to design a nucleic acid probe to identify and clone DNA encoding signal peptides from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

Thus, a genomic DNA or cDNA library prepared from such other organisms may be screened for DNA which hybridizes with the probes described above and which encodes a signal peptide. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 36 or a subsequence thereof, the carrier material is used in a Southern blot. For purposes of the present invention, hybridization indicates that the nucleic acid sequence hybridizes to a labeled nucleic acid probe corresponding to the nucleic acid sequence shown in SEQ ID NO: 36, its complementary strand, or a subsequence thereof, under stringency conditions defined herein. Molecules to which the nucleic acid probe hybridizes under these conditions can be detected using X-ray film.

In a preferred aspect, the nucleic acid probe is a nucleotide sequence which encodes the signal peptide of SEQ ID NO: 37, or a subsequence thereof. In another preferred aspect, the nucleic acid probe is SEQ ID NO: 36. In another preferred aspect, the nucleic acid probe is the signal peptide coding sequence of the endoglucanase V gene contained in *Humicola insolens* DSM 1800.

For short probes which are about 15 nucleotides to about 60 nucleotides in length, stringency conditions are defined as prehybridization, hybridization, and washing post-hybridization at 5° C. to 10° C. below the calculated $T_m$ using the calculation according to Bolton and McCarthy (1962, *Proceedings of the National Academy of Sciences USA* 48: 1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 60 nucleotides in length, the carrier material is washed once in 6×SCC plus 0.1% SDS for 15 minutes and twice each for 15 minutes using 6×SSC at 5° C. to 10° C. below the calculated $T_m$.

In a fourth aspect, the isolated nucleic acid sequences encode variants of the signal peptide having an amino acid sequence of SEQ ID NO: 37 comprising a substitution, deletion, and/or insertion of one or more amino acids.

The amino acid sequences of the variant signal peptides may differ from the amino acid sequence of SEQ ID NO: 37 by an insertion or deletion of one or more amino acid residues and/or the substitution of one or more amino acid residues by different amino acid residues. Preferably, amino acid changes are of a minor nature, such as conservative amino acid substitutions that do not significantly affect the activity of the signal peptide; or small deletions, typically of one to about 5 amino acids.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally after the specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

The present invention also relates to the isolated signal peptide sequences disclosed supra.

Polypeptide Encoding Nucleotide Sequences

The polypeptide encoded by the second nucleotide sequence may be native or heterologous to the fungal host cell of interest.

The term "polypeptide" is not meant herein to refer to a specific length of the encoded product and, therefore, encompasses peptides, oligopeptides, and proteins. The term "heterologous polypeptide" is defined herein as a polypeptide which is not native to the fungal cell, a native polypeptide in which modifications have been made to alter the native sequence, or a native polypeptide whose expression is quantitatively altered as a result of a manipulation of the gene encoding the polypeptide by recombinant DNA techniques. The fungal cell may contain one or more copies of the nucleotide sequence encoding the polypeptide.

Preferably, the polypeptide is a hormone or variant thereof, enzyme, receptor or portion thereof, antibody or portion thereof, or reporter. In a preferred aspect, the polypeptide is an oxidoreductase, transferase, hydrolase, lyase, isomerase, or ligase. In a more preferred aspect, the polypeptide is an aminopeptidase, amylase, carbohydrase, carboxypeptidase, catalase, cellulase, cellobiohydrolase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, xylanase, or beta-xylosidase. In a most preferred aspect, the polypeptide is an endoglucanase, cellobiohydrolase, and/or beta-glucosidase useful in converting cellulose to glucose including, but not limited to, endoglucanase I, endoglucanase II, endoglucanse III, endoglucanase IV, endoglucanase V, cellobiohydrolase I, cellobiohydrolase II, and beta-glucosidase, Endoglucanase and cellobiohydrolase enzymes are collectively referred to as "cellulases."

The nucleotide sequence encoding a polypeptide of interest may be obtained from any prokaryotic, eukaryotic, or other source. For purposes of the present invention, the term "obtained from" as used herein in connection with a given source shall mean that the polypeptide is produced by the source or by a cell in which a gene from the source has been inserted.

The techniques used to isolate or clone a nucleotide sequence encoding a polypeptide of interest are known in the art and include isolation from genomic DNA, preparation from cDNA, or a combination thereof. The cloning of the nucleotide sequence from such genomic DNA can be effected, e.g., by using the well known polymerase chain reaction (PCR). See, for example, Innis et al, 1990, *PCR Protocols. A Guide to Methods and Application*, Academic Press, New York. The cloning procedures may involve excision and isolation of a desired nucleotide fragment comprising the nucleotide sequence encoding the polypeptide, insertion of the fragment into a vector molecule, and incorporation of the recombinant vector into the mutant fungal cell where multiple copies or clones of the nucleotide sequence will be replicated. The nucleotide sequence may be of genomic, cDNA, RNA, semisynthetic, synthetic origin, or any combinations thereof.

In the methods of the present invention, the polypeptide may also include a fused or hybrid polypeptide in which another polypeptide is fused at the N-terminus or the C-terminus of the polypeptide or fragment thereof. A fused polypeptide is produced by fusing a nucleotide sequence (or a portion thereof) encoding one polypeptide to a nucleotide sequence (or a portion thereof) encoding another polypeptide. Techniques for producing fusion polypeptides are known in the art, and include, ligating the coding sequences encoding the polypeptides so that they are in frame and expression of the fused polypeptide is under control of the same promoter(s) and terminator. The hybrid polypeptide may comprise a combination of partial or complete polypeptide sequences obtained from at least two different polypeptides wherein one or more may be heterologous to the mutant fungal cell.

Nucleic Acid Constructs

The present invention also relates to nucleic acid constructs comprising a nucleotide sequence encoding a polypeptide operably linked to a signal peptide sequence of the present invention and one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleotide molecule, either single- or double-stranded, which is isolated from a naturally occurring gene or which has been modified to contain segments of nucleic acids combined and juxtaposed in a manner that would not otherwise exist in nature. The term nucleic acid construct is synonymous with the term expression cassette when the nucleic acid construct contains a coding sequence and all the control sequences required for expression of the coding sequence.

An isolated nucleotide sequence encoding a polypeptide may be further manipulated in a variety of ways to provide for expression of the polypeptide. Manipulation of the nucleotide sequence prior to its insertion into a vector may be desirable or necessary depending on the expression vector. The techniques for modifying nucleotide sequences utilizing recombinant DNA methods are well known in the art.

In the methods of the present invention, the nucleotide sequence may comprise one or more native control sequences or one or more of the native control sequences may be replaced with one or more control sequences foreign to the nucleotide sequence for improving expression of the coding sequence in a host cell.

The term "control sequences" is defined herein to include all components which are necessary or advantageous for the expression of a polypeptide of interest. Each control sequence may be native or foreign to the nucleotide sequence encoding the polypeptide. Such control sequences include, but are not limited to, a leader, polyadenylation sequence, propeptide sequence, signal peptide sequence of the present invention, and transcription terminator. At a minimum, the control sequences include a signal peptide sequence of the present invention, and transcriptional and translational stop signals. The control sequences may be provided with linkers for the purpose of introducing specific restriction sites facilitating ligation of the control sequences with the coding region of the nucleotide sequence encoding a polypeptide.

The control sequence may be an appropriate promoter sequence, which is recognized by a host cell for expression of the nucleotide sequence. The promoter sequence contains transcriptional control sequences which mediate the expression of the polypeptide. The promoter may be any sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awarnori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase, *Fusarium oxysporum* trypsin-like protease (WO 96/00787), *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, *Yeast* 8: 423-488.

The control sequence may be a suitable transcription terminator sequence, which is recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, which is operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. In yeast, the ADH2 system or GAL4 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a signal peptide sequence of the present invention, a nucleotide sequence encoding a polypeptide of interest, and transcriptional and translational stop signals. The various nucleotide and control sequences described above may be joined together to produce a recombinant expression vector which may include one or more convenient restriction sites to allow for insertion or substitution of the promoter and/or nucleotide sequence encoding the polypeptide at such sites. Alternatively, the nucleotide sequence may be expressed by inserting the nucleotide sequence or a nucleic acid construct comprising the signal peptide sequence and/or nucleotide sequence encoding the polypeptide into an appropriate vector for expression. In creating the expression vector, the coding sequence is located in the vector so that the coding sequence is operably linked with a signal peptide sequence of the present invention and one or more appropriate control sequences for expression.

The recombinant expression vector may be any vector (e.g., a plasmid or virus) which can be conveniently subjected to recombinant DNA procedures and can bring about the expression of the nucleotide sequence. The choice of the vector will typically depend on the compatibility of the vector with the host cell into which the vector is to be introduced. The vectors may be linear or closed circular plasmids.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain an element(s) that permits stable integration of the vector into the host cell's genome or autonomous replication of the vector in the cell independent of the genome.

For integration into the host cell genome, the vector may rely on the nucleotide sequence encoding the polypeptide or any other element of the vector for stable integration of the vector into the genome by homologous or nonhomologous recombination. Alternatively, the vector may contain additional nucleotide sequences for directing integration by homologous recombination into the genome of the host cell. The additional nucleotide sequences enable the vector to be integrated into the host cell genome at a precise location(s) in the chromosome(s). To increase the likelihood of integration at a precise location, the integrational elements should preferably contain a sufficient number of nucleotides, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

Examples of origins of replication useful in a filamentous fungal cell are AMA1 and ANS1 (Gems et al., 1991, *Gene* 98:61-67; Cullen et al., 1987, *Nucleic Adds Research* 15: 9163-9175; WO 00/24883). Isolation of the AMA1 gene and construction of plasmids or vectors comprising the gene can be accomplished according to the methods disclosed in WO 00/24883.

More than one copy of a nucleotide sequence encoding a polypeptide may be inserted into the host cell to increase production of the gene product. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a signal peptide sequence of the present invention operably linked to a nucleotide sequence encoding a polypeptide, which are advantageously used in the recombinant production of the polypeptides. A vector comprising a signal peptide sequence of the present invention operably linked to a nucleotide sequence encoding a polypeptide is introduced into a host cell so that the vector is maintained as a chromosomal integrant or as a self-replicating extra-chromosomal vector as described earlier. The term "host cell"

encompasses any progeny of a parent cell that is not identical to the parent cell due to mutations that occur during replication. The choice of a host cell will to a large extent depend upon the gene encoding the polypeptide and its source.

The host cell may be any fungal cell useful in the methods of the present invention. "Fungi" as used herein includes the phyla Ascomycota, Basidiomycota, Chytridiomycota, and Zygomycota (as defined by Hawksworth et al, *In, Ainsworth and Bisby's Dictionary of The Fungi*, 8th edition, 1995, CAB International, University Press, Cambridge, UK) as well as the Oomycota (as cited in Hawksworth et al, 1995, supra, page 171) and all mitosporic fungi (Hawksworth et al., 1995, supra).

In a preferred aspect, the fungal host cell is a yeast cell. "Yeast" as used herein includes ascosporogenous yeast (Endomycetales), basidiosporogenous yeast, and yeast belonging to the Fungi Imperfect (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteria Symposium Series* No. 9, 1980).

In a more preferred aspect, the yeast host cell is a *Candida, Hansenula, Kluyveromyces, Pichia, Saccharomyces, Schizosaccharomyces,* or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred aspect, the yeast host cell is a *Kluyveromyces lactic* cell. In another most preferred aspect, the yeast host cell is a *Yarrowia lipolytica* cell.

In another preferred aspect, the fungal host cell is a filamentous fungal cell. "Filamentous fungi" include all filamentous forms of the subdivision Eumycota and Oomycota (as defined by Hawksworth et al, 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In a more preferred aspect, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium,* or *Trichoderma*.

In an even more preferred aspect, the filamentous fungal host cell is an *Aspergillus awamori, Aspergillus foetidus, Aspergillus japonicus, Aspergillus nidulans, Aspergillus niger* or *Aspergillus oryzae* cell. In another even more preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi; Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another even more preferred aspect, the filamentous fungal host cell is a *Humicola insolens, Humicola lanuginosa, Mucor miehei, Myceliophthora thermophlia, Neurospora crassa, Penicillium purpurogenum, Thielavia terrestris, Trichoderma harzianum, Trichoderma koningli, Trichoderma longibrachiatum, Trichoderma reesei;* or *Trichoderma viride* cell.

In a most preferred aspect, the *Fusarium venenatum* cell is *Fusarium venenatum* A3/5, which was originally deposited as *Fusarium graminearum* ATCC 20334 and recently reclassified as *Fusarium venenatum* by Yoder and Christianson, 1998, *Fungal Genetics and Biology* 23: 62-80 and O'Donnell et al., 1998, *Fungal Genetics and Biology* 23: 57-67; as well as taxonomic equivalents of *Fusarium venenatum* regardless of the species name by which they are currently known. In another preferred aspect, the *Fusarium venenatum* cell is a morphological mutant of *Fusarium venenatum* A3/5 or *Fusarium venenatum* ATCC 20334, as disclosed in WO 97/26330.

In another most preferred aspect, the *Trichoderma* cell is *Trichoderma reesei* ATCC 56765, *Trichoderma reesei* ATCC 13631, *Trichoderma reesei* CBS 526.94, *Trichoderma reesei* CBS 529.94, *Trichoderma longibrachiatum* CBS 528.94, *Trichoderma longibrachiatum* ATCC 2106, *Trichoderma longibrachiatum* CBS 592.94, *Trichoderma viride* NRRL 3652, *Trichoderma viride* CBS 517.94, and *Trichoderma viride* NIBH FERM/BP 447.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al, 1984, *Proceedings of the National Academy of Sciences USA* 81: 1470-1474. Suitable procedures for transformation of *Trichoderma reesei* host cells is described in Penttila et al., 1987, *Gene* 61: 155-164, and Gruber et al., 1990, *Curr Genet.* 18(1):71-6. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al, 1983, *Journal of Bacteriology* 153: 163; and Hinnen et al, 1978, *Proceedings of the National Academy of Sciences USA* 75: 1920.

Degradation of Biomass

The present invention also relates to methods for degrading or converting a cellulose-containing and/or hemicellulose-containing biomass, comprising treating the biomass with an effective amount of one or more polypeptides obtained by the methods of the present invention, wherein the one or more polypeptides have enzyme activity against the cellulose-containing and/or hemicellulose-containing biomass. For example, the methods of the present invention may be used to produce enzymes and host cells for use in the production of ethanol from biomass. Ethanol can be produced by enzymatic degradation of biomass and conversion of the released polysaccharides to ethanol. This kind of ethanol is often referred to as bioethanol or biofuel. It can be used as a fuel additive or extender in blends of from less than 1% and up to 100% (a fuel substitute).

The methods of the present invention may also be used to produce enzymes and host cells for use in the production of monosaccharides, disaccharides, and polysaccharides as chemical or fermentation feedstocks from biomass for the production of ethanol, plastics, or other products or intermediates. The enzymes may be in the form of a crude fermentation broth with or without the cells removed or in the form of a semi-purified or purified enzyme preparation. Alternatively, a host cell of the present invention may be used as a source of one or more enzymes in a fermentation process with the biomass.

Biomass can include, but is not limited to, wood resources, municipal solid waste, wastepaper, and crop residues (see, for example, Wiselogel et al., 1995, in *Handbook on Bioethanol* (Charles E. Wyman, editor), pp. 105-118, Taylor & Francis, Washington D.C.; Wyman, 1994, *Bioresource Technology* 50: 346; Lynd, 1990, *Applied Biochemistry and Biotechnology* 24/25: 695-719; Mosier et al., 1999, *Recent Progress in Bioconversion of Lignocellulosics*, in *Advances in Biochemical Engineering/Biotechnology*, T. Scheper, managing editor, Volume 65, pp. 23-40, Springer-Verlag, New York).

The predominant polysaccharide in the primary cell wall of biomass is cellulose, the second most abundant is hemi-cellulose, and the third is pectin. The secondary cell wall, produced after the cell has stopped growing, also contains polysaccharides and is strengthened through polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which helps stabilize the cell wall matrix.

Three major classes of glycohydrolases are used to breakdown cellulosic biomass:

(1) The "endo-1,4-beta-glucanases" or 1,4-beta-D-glucan-4-glucanohydrolases (EC 3.2.1.4), which act randomly on soluble and insoluble 1,4-beta-glucan substrates.

(2) The "exo-1,4-beta-D-glucanases" including both the 1,4-beta-D-glucan glucohydrolases (EC 3.2.1.74), which liberate D-glucose from 1,4-beta-D-glucans and hydrolyze D-cellobiose slowly, and cellobiohydrolases (1,4-beta-D-glucan cellobiohydrolases, EC 3.2.1.91), which liberate D-cellobiose from 1,4-beta-glucans.

(3) The "beta-D-glucosidases" or beta-D-glucoside glucohydrolases (EC 3.2.1.21), which act to release D-glucose units from cellobiose and soluble cellodextrins, as well as an array of glycosides.

These three classes of enzymes work together synergistically resulting in efficient decrystallization and hydrolysis of native cellulose from biomass to yield reducing sugars.

The methods of the present invention may also be used to produce other enzymes in conjunction with the above-noted enzymes to further degrade the hemicellulose component of the biomass substrate, (see, for example, Brigham et al., 1995, in *Handbook on Bioethanol* (Charles E. Wyman, editor), pp. 119-141, Taylor & Francis, Washington D.C.; Lee, 1997, *Journal of Biotechnology* 56: 1-24). Such enzymes include, but are not limited to, enzymes that degrade beta-1,3-1,4-glucan such as endo-beta-1,3(4)-glucanase, endoglucanase (beta-glucanase, cellulase), and beta-glucosidase; degrade xyloglucans such as xyloglucanase, endoglucanase, and cellulase; degrade xylan such as xylanase, xylosidase, alpha-arabinofuranosidase, alpha-glucuronidase, and acetyl xylan esterase; degrade mannan such as mannanase, mannosidase, alpha-galactosidase, and mannan acetyl esterase; degrade galactan such as galactanase; degrade arabinan such as arabinanase; degrade homogalacturonan such as pectate lyase, pectin lyase, pectate lyase, polygalacturonase, pectin acetyl esterase, and pectin methyl esterase; degrade rhamnogalacturonan such as alpha-arabinofuranosidase, beta-galactosidase, galactanase, arabinanase, alpha-arabinofuranosidase, rhamnogalacturonase, rhamnogalacturonan lyase, and rhamnogalacturonan acetyl esterase; degrade xylogalacturonan such as xylogalacturonosidase, xylogalacturonase, and rhamnogalacturonan lyase; and degrade lignin such as lignin peroxidases, manganese-dependent peroxidases, hybrid peroxidases, with combined properties of lignin peroxidases and manganese-dependent peroxidases, and laccases. Other enzymes include esterases, lipases, oxidases, phospholipases, phytases, proteases, and peroxidases.

The present invention is further described by the following examples which should not be construed as limiting the scope of the invention.

EXAMPLES

Strains

*Trichoderma reesei* RutC30 (ATCC 56765; Montenecourt and Eveleigh, 1979, *Adv. Chem. Ser.* 181: 289-301) was derived from *Trichoderma reesei* Qm6A (ATCC 13631; Mandels and Reese, 1957, *J. Bacteria.* 73: 269-278). *Trichoderma reesei* RutC30 and *Saccharomyces cerevisiae* YNG318 (MATα, ura3-52, leu-2Δ2, pep4Δ1, his4-539) (WO97/07205) were used as hosts for expression of *Aspergillus oryzae* beta-glucosidase. *Aspergillus fumigatus* PaHa34 was used as the source of the Family GH3A beta-glucosidase.

Media and Buffer Solutions

YP medium was composed per liter of 10 g of yeast extract and 20 g of bactopeptone.

Yeast selection medium was composed per liter of 6.7 g of yeast nitrogen base, 0.8 g of complete supplement mixture (CSM, Qbiogene, Inc., Carlsbad, Calif.; missing uracil and containing 40 mg/ml of adenine), 5 g of casamino acids (without amino acids), 100 ml of 0.5 M succinate pH 5.0, 40 ml of 50% glucose, 1 ml of 100 mM $CuSO_4$, 50 mg of ampicillin, and 25 mg of chloramphenicol.

Yeast selection plate medium was composed per liter of yeast selection medium supplemented with 20 g of bacto agar and 150 mg of 5-bromo-4-chloro-3-indolyl-beta-D-glucopyranoside (X-Glc, INALCO SPA, Milano, Italy) but lacking both ampicillin and chloramphenicol.

COVE selection plates were composed per liter of 342.3 g of sucrose, 20 ml of COVE salt solution, 10 mM acetamide, 15 mM $CsCl_2$, and 25 g of Noble agar.

COVE2 plates were composed per liter of 30 g of sucrose, 20 ml COVE salt solution, 10 mM acetamide, and 25 g of Noble agar.

COVE salt solution was composed per liter of 26 g of KCl, 26 q of $MgSO_4.7H_2O$, 76 g of $KH_2PO_4$, and 50 ml of COVE trace metals.

COVE trace metals solution was composed per liter of 0.04 g of $NaB_4O_7.10H_2O$, 0.4 g of $CuSO_4.5H_2O$, 1.2 g of $FeSO_4.7H_2O$, 0.7 g of $MnSO_4.2O$, 0.8 g of $Na_2MoO_2.2H_2O$, and 10 g of $ZnSO_4.7H_2O$.

Cellulase-inducing media was composed per liter of 20 g of Arbocel B800-natural cellulose fibers (J. Rettenmaier USA LP, Schoolcraft, Mich.), 10 g of corn steep solids (Sigma Chemical Co., St. Louis, Mo.), 1.45 g of $(NH)_2SO_4$, 2.08 g of $KH_2PO_4$, 0.28 g of $CaCl_2$, 0.42 g of $MgSO_4.7H_2O$, 0.42 ml *Trichoderma reesei* Trace Metals, and 2 drops of pluronic acid; pH to 6.0 with 10 N NaoH.

*Trichoderma reesei* trace metals solution was composed per liter of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, and 336 g of citric acid.

PEG Buffer was composed per liter of 500 g of PEG 4000 (BDH, Poole, England), 10 mM $CaCl_2$, and 10 mM Tris-HCl pH 7.5 (filter sterilize).

STC was composed per liter of 1 M sorbitol, 10 mM $CaCl_2$, and 10 mM Tris-HCl pH 7.5 (filter sterilize).

Inoculum Medium was composed per liter of 20 g of glucose, 10 g of corn steep solids (Sigma Chemical Co., St. Louis, Mo.), 1.45 g of $(NH_4)_2SO_4$, 2.08 g of $KH_2PO_4$, 0.28 g of $CaCl_2$, 0.42 g of $MgSO_4.7H_2O$, 0.42 ml of *Trichoderma reesei* trace metals solution, and 2 drops of pluronic acid; final pH 5.0.

Fermentation Medium was composed per liter of 4 g of glucose, 10 g of corn steep solids, 30 g of Arbocel B800-natural cellulose fibers (J. Rettenmaier USA LP, Schoolcraft, Mich.), 3.8 g of $(NH_4)_2SO_4$, 2.8 g of $KH_2PO_1$, 2.08 g of $CaCl_2$, 1.63 g of $MgSO_4.7H_2O$, 0.75 ml of *Trichoderma reesei* trace metals solution, and 1.8 ml of pluronic acid.

Feed Medium was composed per liter of 600 g of glucose, 20 g of Cellulose B800, 35.5 g of $H_3PO4$, and 5 ml of pluronic acid.

Beta-Glucosidase Activity Assay

For *Trichoderma reesei* samples, beta-glucosidase activity was determined at ambient temperature using 25 µl aliquots of culture supernatants, diluted 1:10 in 50 mM succinate pH 5.0, using 200 µl of 0.5 mg/ml p-nitrophenyl-beta-D-glucopyranoside as substrate in 50 mM succinate pH 5.0. After 15 minutes incubation the reaction was stopped by adding 100 µl of 1 M Tris-HCl pH 8.0 and the absorbance was read spectrophotometrically at 405 nm.

For *Saccharomyces cerevisiae* samples, culture supernatant samples were diluted 0.6-fold with 0.1 M succinate pH 5.0 in 96-wells microtiter plates. Twenty five µl of the diluted samples were taken from each well and added to a new 96-well plate, containing 200 µl of 1 mg/ml p-nitrophenyl-beta-D-glucopyranoside substrate. The plates were incubated at ambient temperature for 1.5 hours and the reaction stopped by adding 2 M Tris-HCl pH 9. The plates were then read spectrophotometrically at 405 nm.

One unit of beta-glucosidase activity corresponded to production of 1 µmol of p-nitrophenyl per minute per liter at pH 5.0, ambient temperature. *Aspergillus niger* beta-, glucosidase (Novozyme 188, Novozymes A/S, Bagsvaerd, Denmark) was used as an enzyme standard.

DNA Sequencing

DNA sequencing was performed on an ABI3700 (Applied Biosystems, Foster City, Calif.) using dye terminator chemistry (Giesecke et al, 1992, *Journal of Virol. Methods* 38: 47-60). Sequences were assembled using phred/phrap/consed (University of Washington, Seattle Wash.) with sequence specific primers.

Example 1

Construction of pAlLo1 Expression Vector

Expression vector pAlLo1 was constructed by modifying pBANe6 (U.S. Pat. No. 6,461,837), which comprises the NA2-tpi promoter, *Aspergillus niger* amyloglucosidase terminator sequence (AMG terminator), and *Aspergillus nidulans* acetamidase gene (amdS). Modification of pBANe6 was performed by first eliminating three Nco I restriction sites at positions 2051, 2722, and 3397 bp from the amdS selection marker by site directed mutagenesis. All changes were designed to be "silent" leaving the actual protein sequence of the amdS gene product unchanged. Removal of these three sites was performed simultaneously with a GeneEditor Site-Directed Mutagenesis Kit (Promega, Madison, Wis.) according to the manufacturer's instructions using the following primers (underlined nucleotide represents the changed base):

```
AMDS3NcoMut (2050):
                                   (SEQ ID NO: 1)
5'-GTGCCCCATGATACGCCTCCGG-3'

AMDS2NcoMut (2721):
                                   (SEQ ID NO: 2)
5'-GAGTCGTATTTCCAAGGCTCCTGACC-3'

AMDS1NcoMut (3396):
                                   (SEQ ID NO: 3)
5'-GGAGGCCATGAAGTGGACCAACGG-3'
```

A plasmid comprising all three expected sequence changes was then submitted to site-directed mutagenesis, using a QuickChange Mutagenesis Kit (Stratagene, La Jolla, Calif.), to eliminate the Nco I restriction site at the end of the AMG terminator at position 1643. The following primers (underlined nucleotide represents the changed base) were used for mutagenesis:

Upper Primer to mutagenize the *Aspergillus niger* amyloglucosidase (AMG) terminator sequence:

```
                                   (SEQ ID NO: 4)
5'-CACCGTGAAAGCCATGCTCTTTCCTTCGTGTAGAAGACCAGACAG-
3'
```

Lower Primer to mutagenize the *Aspergillus niger* amyloglucosidase (AMG) terminator sequence:

```
                                   (SEQ ID NO: 5)
5'-CTGGTCTTCTACACGAAGGAAAGAGCATGGCTTTCACGGTGTCTG-
3'
```

The last step in the modification of pBANe6 was the addition of a new Nco I restriction site at the beginning of the polylinker using a QuickChange Mutagenesis Kit and the following primers (underlined nucleotides represent the changed bases) to yield pAlLo1 (FIG. 1). Upper Primer to mutagenize the *Aspergillus niger* amylase promoter (NA2-tpi):

```
                                   (SEQ ID NO: 6)
5'-CTATATACACAACTGGATTTACCATGGGCCCGCGGCCGCAGATC-
3'
```

Lower Primer to mutagenize the *Aspergillus niger* amylase promoter (NA2-tpi):

```
                                   (SEQ ID NO: 7)
5'-GATCTGCGGCCGCGGGCCCATGGTAAATCCAGTTGTGTATATAG-
3'
```

Figure 14:
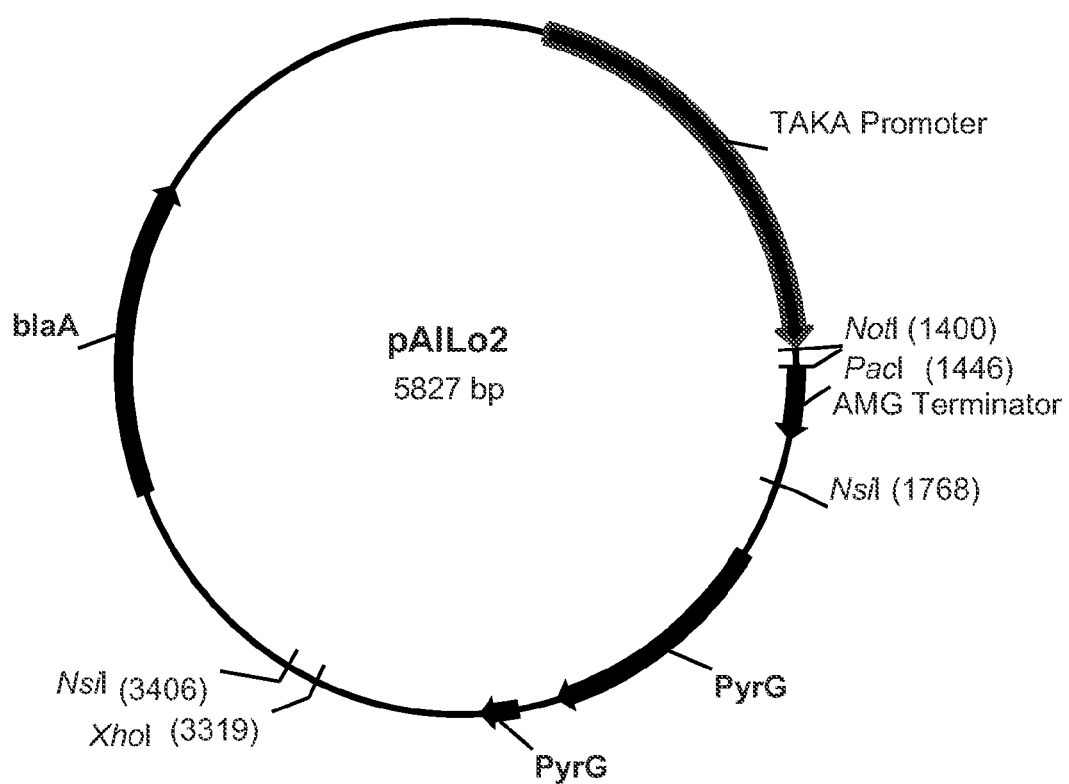
FIG. 14 shows a restriction map of pAlLo2.
Figure 15:
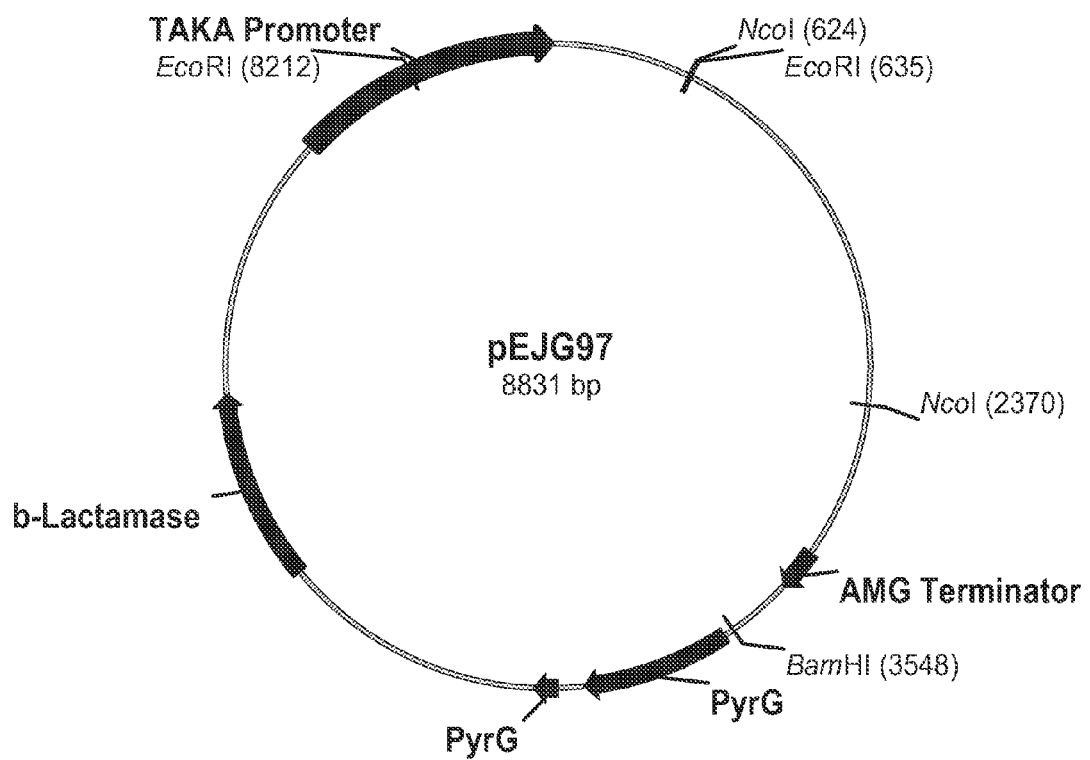
FIG. 15 shows a restriction map of pEJG97.

The amdS gene of pAlLo1 was swapped with the *Aspergillus nidulans* pyrG gene. Plasmid pBANe10 (FIG. 14) was used as a source for the pyrG gene as a selection marker. Analysis of the sequence of pBANe10 showed that the pyrG marker was contained within an Nsi I restriction fragment and does not contain either Nco I or Pac I restriction sites. Since the amdS is also flanked by Nsi I restriction sites the strategy to switch the selection marker was a simple swap of Nsi I restriction fragments. Plasmid DNA from pAlLo1 and pBANe10 were digested with the restriction enzyme Nsi I and the products purified by agarose gel electrophoresis. The Nsi I fragment from pBANe10 containing the pyrG gene was ligated to the backbone of pAlLo1 to replace the original Nsi I DNA fragment containing the amdS gene. Recombinant clones were analyzed by restriction digest to determine that they had the correct insert and also its orientation. A clone with the pyrG gene transcribed in the counterclockwise direction was selected. The new plasmid has been designated pAlLo2 (FIG. 15).

Example 2

Construction of pMJ04 Expression Vector

Expression vector pMJ04 was constructed by PCR amplifying the *Trichoderma reesei* exocellobiohydrolase 1 gene (cbh1) terminator from *Trichoderma reesei* RutC30 genomic DNA using primers 993429 (antisense) and 993428 (sense) shown below. The antisense primer was engineered to have a Pac I site at the 5'-end and a Spe I site at the 3'-end of the sense primer.

Primer 993429 (antisense):

(SEQ ID NO: 8)
5'-AACGTTAATTAAGGAATCGTTTTGTGTTT-3'

Primer 993428 (sense):

(SEQ ID NO: 9)
5'-AGTACTAGTAGCTCCGTGGCGAAAGCCTG-3'

*Trichoderma reesei* RutC30 genomic DNA was isolated using a DNeasy Plant Maxi Kit (Qiagen, Chatsworth, Calif.).

The amplification reactions (50 µl) were composed of 1× ThermoPol Reaction Buffer (New England Biolabs, Beverly, Mass.), 0.3 mM dNTPs, 100 ng of *Trichoderma reesei* RutC30 genomic DNA, 0.3 µM primer 993429, 0.3 µM primer 993428, and 2 units of Vent polymerase (New England Biolabs, Beverly, Mass.). The reactions were incubated in an Eppendorf Mastercycler 5333 (Eppendorf Scientific, Inc., Westbury, N.Y.) programmed as follows: 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using 40 mM Tris base-20 mM sodium acetate-1 mM disodium EDTA (TAE) buffer where a 229 bp product band was excised from the gel and purified using a QIAquick Gel Extraction Kit (QIAGEN, Chatsworth, Calif.) according to the manufacturer's instructions.

Figure 2:
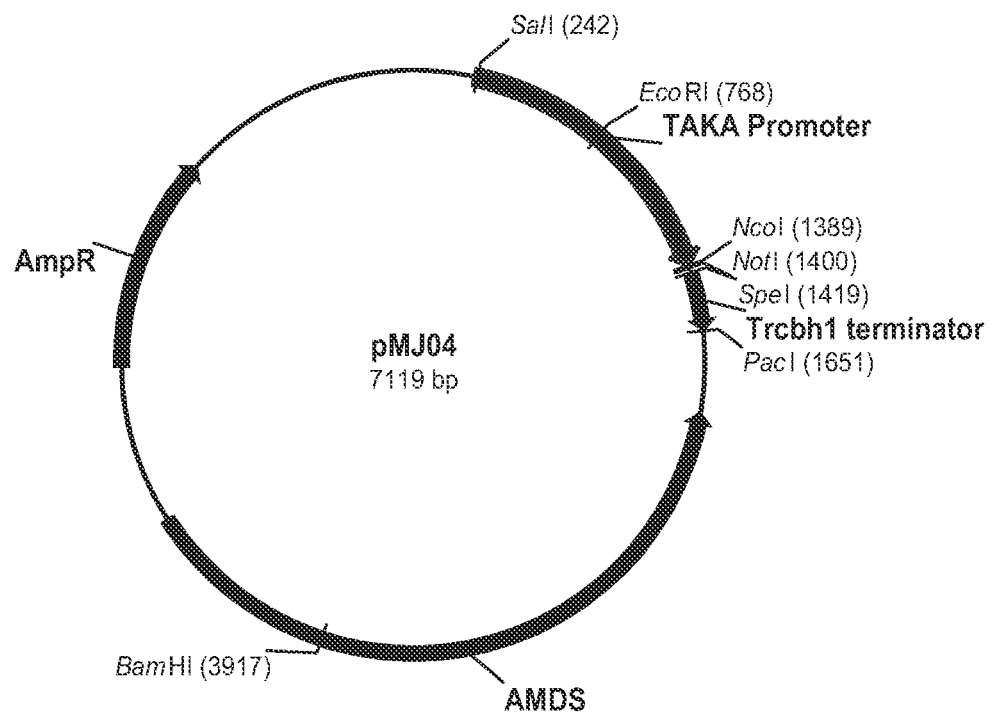
FIG. 2 shows a restriction map of pMJ04.

The resulting PCR fragment was digested with Par: I and Spe I and ligated into pAlLo01 digested with the same restriction enzymes using a Rapid Ligation Kit (Roche, Indianapolis, Ind.), to generate pMJ04 (FIG. 2).

Example 3

Construction of pCaHj568 Expression Vector

Expression plasmid pCaHj568 was constructed from pCaHj170 (U.S. Pat. No. 5,763,254) and pMT2188. Plasmid pCaHj170 comprises the *Humicola insolens* endoglucanase V (EGV) coding region. Plasmid pMT2188 was constructed as follows: The pUC19 origin of replication was PCR amplified from pCaHj483 (WO 98/00529) with primers 142779 and 142780 shown below. Primer 142780 introduces a BbuI site in the PCR fragment.

142779:

(SEQ ID NO: 10)
5'-TTGAATTGAAAATAGATTGATTTAAAACTTC-3'

142780:

(SEQ ID NO: 11)
5'-TTGCATGCGTAATCATGGTCATAGC-3'

The Expand PCR system (Roche Molecular Biochemicals, Basel, Switserland) was used for the amplification following the manufacturer's instructions for this and the subsequent PCR amplifications. PCR products were separated on a 1% agarose gel using TAE buffer and an 1160 bp fragment was isolated and purified using a Jetquick Gel Extraction Spin Kit (Genomed, Wielandstr, Germany).

The URA3 gene was amplified from the *Saccharomyces cerevisiae* cloning vector pYES2 (Invitrogen, Carlsbad, Calif.) using primers 140288 and 142778 below. Primer 140288 introduces an Eco RI site in the PCR fragment.

140288:

(SEQ ID NO: 12)
5'-TTGAATTCATGGGTAATAACTGATAT-3'

142778:

(SEQ ID NO: 13)
5'-AAATCAATCTATTTTCAATTCAATTCATCATT-3'

PCR products were separated on a 1% agarose gel using TAE buffer and an 1126 bp fragment was isolated and purified using a Jetquick Gel Extraction Spin Kit.

The two PCR fragments were fused by mixing and amplification using primers 142780 and 140288 shown above by overlap method splicing (Horton et al, 1989, *Gene* 77: 61-68). PCR products were separated on 1% agarose gel using TAE buffer and a 2263 bp fragment was isolated and purified using a Jetquick Gel Extraction Spin Kit.

Figure 3:
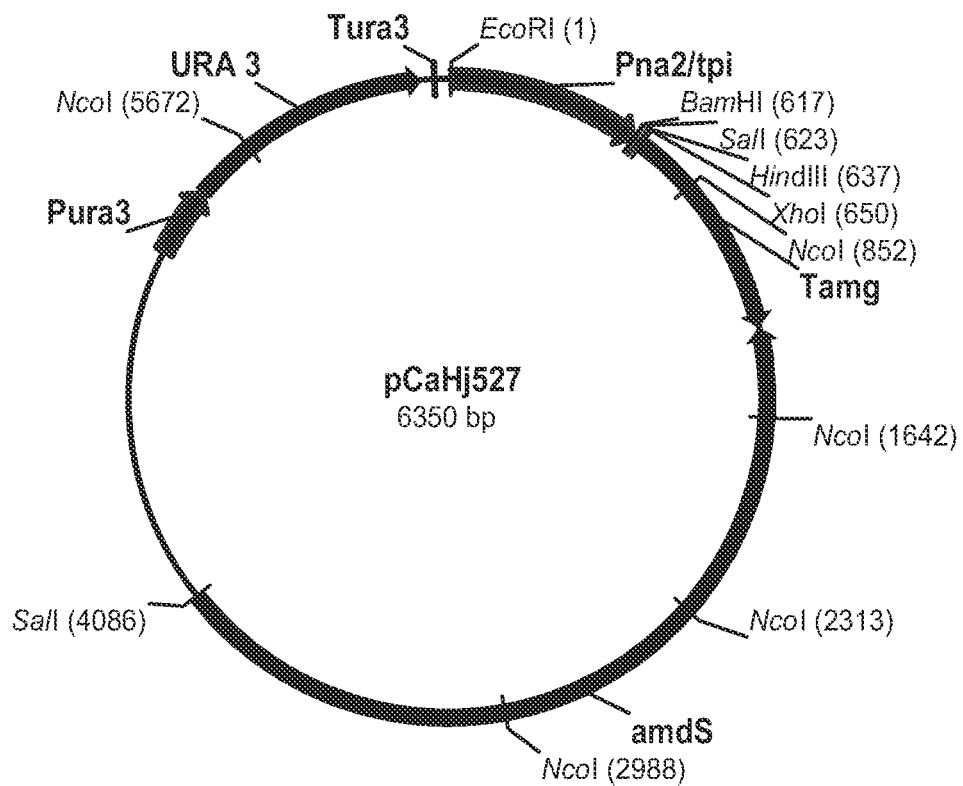
FIG. 3 shows a restriction map of pCaHj527.

The resulting fragment was digested with Eco RI and Bbu I and ligated to the largest fragment of pCaHj483 digested with the same enzymes. The ligation mixture was used to transform pyrF-negative *E. coli* strain DB6507 (ATCC 35673) made competent by the method of Mandel and Higa, 1970, *J. Mol. Biol.* 45: 154. Transformants were selected on solid M9 medium (Sambrook et al., 1989, Molecular Cloning, A Laboratory Manual, 2nd edition, Cold Spring Harbor Laboratory Press) supplemented per liter with 1 g of casaminoacids, 500 µg of thiamine, and 10 mg of kanamycin. A plasmid from one transformant was isolated and designated pCaHj527 (FIG. 3).

The NA2/tpi promoter present on pCaHj527 was subjected to site directed mutagenesis by a simple PCR approach. Nucleotides 134-144 were converted from GTACTAAAACC to CCGTTAAATTT using mutagenic primer 141223:

Primer 141223:

(SEQ ID NO: 14)
5'-GGATGCTGTTGACTCCGGAAATTTAACGGTTTGGTCTTGCATCCC-3'

Nucleotides 423-436 were converted from ATGCAATT-TAAACT to CGGCAATTTAACGG using mutagenic primer 141222:

```
Primer 141222:
                                       (SEQ ID NO: 15)
5'-GGTATTGTCCTGCAGACGGCAATTTAACGGCTTCTGCGAATCGC-
3'
```

Figure 4:
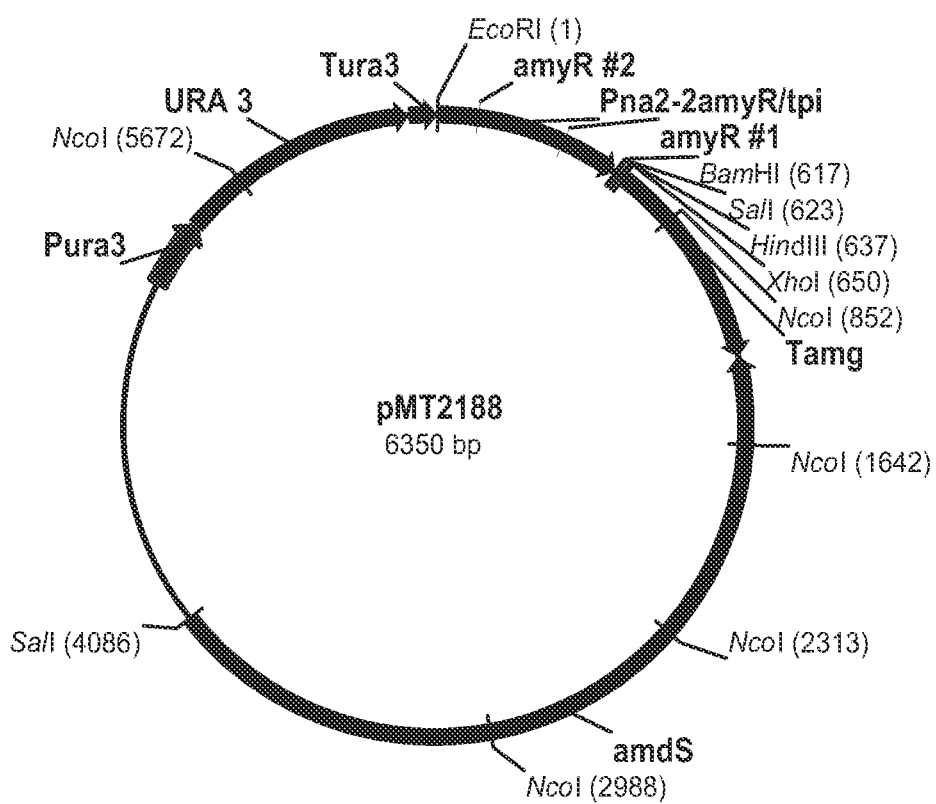
FIG. 4 shows a restriction map of pMT2188.

The resulting plasmid was designated pMT2188 (FIG. 4).

Figure 5:
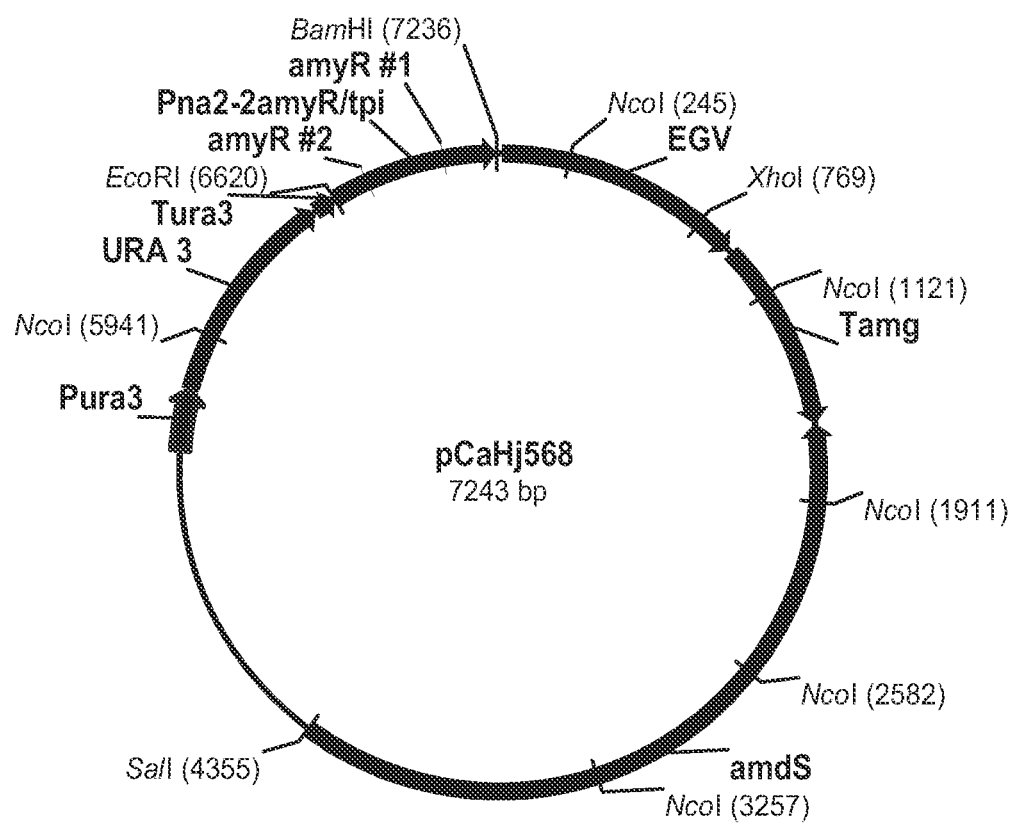
FIG. 5 shows a restriction map of pCaHj568.

The *Humicola insolens* endoglucanase V coding region was transferred from pCaHj170 as a Bam HI-Sal I fragment into pMT2188 digested with Bam HI and Xho I to generate pCaHj568 (FIG. 5).

Example 4

Construction of pMJ05 Expression Vector

Expression vector pMJ05 was constructed by PCR amplifying the 915 bp *Humicola insolens* endoglucanase V coding region from pCaHj568 using primers HiEGV-F and HiEGV-R shown below.

```
HiEGV-F (sense):
                                       (SEQ ID NO: 16)
5'-AAGCTTAAGCATGCGTTCCTCCCCCCTCC-3'

HiEGV-R (antisense):
                                       (SEQ ID NO: 17)
5'-CTGCAGAATTCTACAGGCACTGATGGTACCAG-3'
```

The amplification reactions (50 μl) were composed of 1× ThermoPol Reaction Buffer, 0.3 mM dNTPs, 10 ng/μl pCaHj568 plasmid, 0.3 μM HiEGV-F primer, 0.3 μM HiEGV-R primer, and 2 units of Vent polymerase. The reactions were incubated in an Eppendorf Mastercycler 5333 programmed as follows: 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using TAE buffer where a 937 bp product band was excised from the gel and purified using a QIAquick Gel Extraction Kit according to the manufacturer's instructions.

This 937 bp purified fragment was used as template DNA for subsequent amplifications using the following primers:

```
HiEGV-R (antisense):
                                       (SEQ ID NO: 18)
5'-CTGCAGAATTCTACAGGCACTGATGGTACCAG-3'

HiEGV-F-overlap (sense):
                                       (SEQ ID NO: 19)
5'-ACCGCGGACTGCGCATCATGCGTTCCTCCCCCCTCC-3'
```

Primer sequences in italics are homologous to 17 bp of the *Trichoderma reesei* cbh1 promoter and underlined primer sequences are homologous to 29 bp of the *Humicola insolens* endoglucanase V coding region. The 36 bp overlap between the promoter and the coding sequence allowed precise fusion of the 994 bp fragment comprising the *Trichoderma reesei* cbh1 promoter to the 918 bp fragment comprising the *Humicola insolens* endoglucanase V open reading frame.

The amplification reactions (50 μl) were composed of 1× ThermoPol Reaction Buffer, 0.3 mM dNTPs, 1 ul of 937 bp purified PCR fragment, 0.3 μM HiEGV-F-overlap primer, 0.3 μM HiEGV-R primer, and 2 units of Vent polymerase. The reactions were incubated in an Eppendorf Mastercycler 5333 programmed as follows: 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using TAE buffer where a 945 bp product band was excised from the gel and purified using a QIAquick Gel Extraction Kit according to the manufacturer's instructions.

A separate PCR was performed to amplify the *Trichoderma reesei* cbh1 promoter sequence extending from 994 bp upstream of the ATG start codon of the gene from *Trichoderma reesei* RutC30 genomic DNA using the following primers (sense primer was engineered to have a Sal I restriction site at the 5'-end):

```
TrCBHIpro-F (sense):
                                       (SEQ ID NO: 20)
5'-AAACGTCGACCGAATGTAGGATTGTTATC-3'

TrCBHIpro-R (antisense):
                                       (SEQ ID NO: 21)
5'-GATGCGCAGTCCGCGGT-3'
```

The amplification reactions (50 μl) were composed of 1× ThermoPol Reaction Buffer, 0.3 mM dNTPs, 100 ng of *Trichoderma reesei* RutC30 genomic DNA, 0.3 μM TrCBHIpro-F primer, 0.3 μM TrCBHIpro-R primer, and 2 units of Vent polymerase. The reactions were incubated in an Eppendorf Mastercycler 5333 programmed as follows: 30 cycles each for 30 seconds at 94° C., 30 seconds at 55° C., and 120 seconds at 72° C. (5 minute final extension). The reaction products were isolated on a 1.0% agarose gel using TAE buffer where a 998 bp product band was excised from the gel and purified using a QIAquick Gel Extraction Kit according to the manufacturer's instructions.

The 998 bp purified PCR fragment was used to as template DNA for subsequent amplifications using the following primers:

```
TrCBHIpro-F:
                                       (SEQ ID NO: 22)
5'-AAACGTCGACCGAATGTAGGATTGTTATC-3'

TrCBHIpro-R-overlap:
                                       (SEQ ID NO: 23)
5'-GGAGGGGGAGGAACGCATGATGCGCAGTCCGCGGT-3'
```

Sequences in italics are homologous to 17 bp of the *Trichoderma reesei* cbh1 promoter and underlined sequences are homologous to 29 bp of the *Humicola insolens* endoglucanase V coding region. The 36 bp overlap between the promoter and the coding sequence allowed precise fusion of the 994 bp fragment comprising the *Trichoderma reesei* cbh1 promoter to the 918 bp fragment comprising the *Humicola insolens* endoglucanase V open reading frame.

The amplification reactions (50 μl) were composed of 1× ThermoPol Reaction Buffer, 0.3 mM dNTPs, 1 μl of 998 bp purified PCR fragment, 0.3 μM TrCBH1pro-F primer, 0.3 μM TrCBH1pro-R-overlap primer, and 2 units of Vent polymerase. The reactions were incubated in an Eppendorf Mastercycler 5333 programmed as follows: 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using TAE buffer where a 1017 bp product band was excised from the gel and purified using a QIAquick Gel Extraction Kit according to the manufacturer's instructions.

The 1017 bp *Trichoderma reesei* cbh1 promoter PCR fragment and the 945 bp *Humicola insolens* endoglucanase V PCR fragments were used as template DNA for subsequent amplification using the following primers to precisely fuse the 994 bp *Trichoderma reesei* cbh1 promoter to the 918 bp *Humicola insolens* endoglucanase V coding region using overlapping PCR.

```
TrCBHIpro-F:
                                    (SEQ ID NO: 24)
5'-AAACGTCGACCGAATGTAGGATTGTTATC-3'

HIEGV-R:
                                    (SEQ ID NO: 25)
5'-CTGCAGAATTCTACAGGCACTGATGGTACCAG-3'
```

The amplification reactions (50 µl) were composed of 1× ThermoPol Reaction Buffer, 0.3 mM dNTPs, 0.3 µM TrCBH1pro-F primer, 0.3 µM HiEGV-R primer, and 2 U of Vent polymerase. The reactions were incubated in an Eppendorf Mastercycler 5333 programmed as follows: 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using TAE buffer where a 1926 bp product band was excised from the gel and purified using a QIAquick Gel Extraction Kit according to the manufacturer's instructions.

Figure 6:
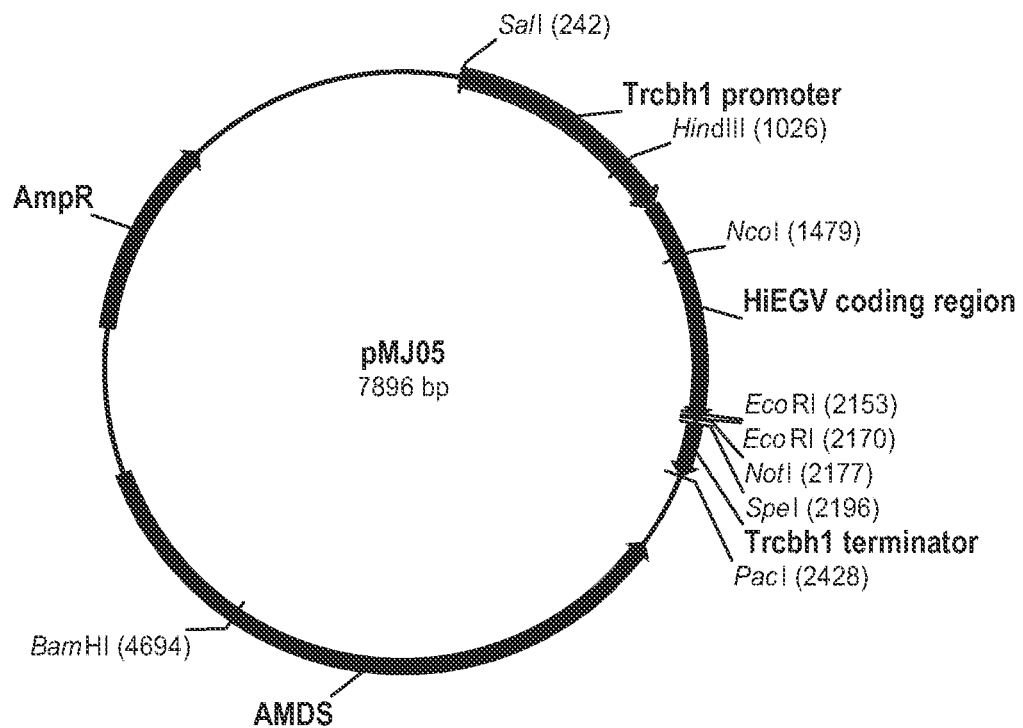
FIG. 6 shows a restriction map of pMJ05.

The resulting 1926 bp fragment was cloned into pCR-Blunt-II-TOPO vector using a Zero Blunt™ TOPO PCR Cloning Kit (Invitrogen, Carlsbad, Calif.) following the manufacturer's protocol. The resulting plasmid was digested with Not I and SalI and the 1926 bp fragment purified and ligated into pMJ04 expression vector which was also digested with the same two restriction enzymes, to generate pMJ05 (FIG. 6).

Example 5

Construction of pSMai130 Expression Vector

A 2586 bp DNA fragment spanning from the ATG start codon to the TAA stop codon of the *Aspergillus oryzae* beta-glucosidase coding sequence (SEQ ID NO: 42 for cDNA sequence and SEQ ID NO: 43 for the deduced amino acid sequence; *E. coli* DSM 14240) was amplified by PCR from pJaL660 (WO 2002/095014) as template with primers 993467 (sense) and 993456 (antisense) shown below. A Spe I site was engineered at the 5' end of the antisense primer to facilitate ligation. Primer sequences in italics are homologous to 24 bp of the *Trichoderma reesei* cbh1 promoter and underlined sequences are homologous to 22 bp of the *Aspergillus oryzae* beta-glucosidase coding region.

```
Primer 993467:
                                    (SEQ ID NO: 26)
5'-ATAGTCAACCGCGGACTGCGCATCATGAAGCTTGGTTGGATCGAG
G-3'

Primer 993456:
                                    (SEQ ID NO: 27)
5'-ACTAGTTTACTGGGCCTTAGGCAGCG-3'
```

The amplification reactions (50 µl) were composed of Pfx Amplification Buffer (Invitrogen, Carlsbad, Calif.), 0.25 mM dNTPs, 10 ng of pJaL660 plasmid, 6.4 µM primer 993467, 3.2 µM primer 993456, 1 mM MgCl$_2$, and 2.5 units of Pfx DNA polymerase (Invitrogen, Carlsbad, Calif.). The reactions were incubated in an Eppendorf Mastercycler 5333 programmed as follows: 30 cycles each for 60 seconds at 94° C., 60 seconds at 55° C., and 180 seconds at 72° C. (15 minute final extension). The reaction products were isolated on a 1.0% agarose gel using TAE buffer where a 2586 bp product band was excised from the gel and purified using a QIAquick Gel Extraction Kit according to the manufacturer's instructions.

A separate PCR was performed to amplify the *Trichoderma reesei* cbh1 promoter sequence extending from 1000 bp upstream of the ATG start codon of the gene, using primer 993453 (sense) and primer 993463 (antisense) shown below to generate a 1000 bp PCR fragment. Primer sequences in italics are homologous to the 24 bp of the *Trichoderma reesei* cbh1 promoter and underlined primer sequences are homologous to the 22 bp of the *Aspergillus oryzae* beta-glucosidase coding region. The 46 bp overlap between the promoter and the coding sequence allows precise fusion of the 1000 bp fragment comprising the *Trichoderma reesei* cbh1 promoter to the 2586 bp fragment comprising the *Aspergillus oryzae* beta-glucosidase open reading frame.

```
Primer 993453:
                                    (SEQ ID NO: 28)
5'-GTCGACTCGAAGCCCGAATGTAGGAT-3'

Primer 993463:
                                    (SEQ ID NO: 29)
5'-CCTCGATCCAACCAAGCTTCATGATGCGCAGTCCGCGGTTGACT
A-3'
```

The amplification reactions (50 µl) were composed of Pfx Amplification Buffer, 0.25 mM dNTPs, 100 ng of *Trichoderma reesei* RutC30 genomic DNA, 6.4 µM primer 993453, 12 µM primer 993463, 1 mM MgCl$_7$, and 2.5 units of Pfx DNA polymerase. The reactions were incubated in an Eppendorf Mastercycler 5333 programmed as follows: 30 cycles each for 60 seconds at 94° C., 60 seconds at 55° C., and 180 seconds at 72° C. (15 minute final extension). The reaction products were isolated on a 1.0% agarose gel using TAE buffer where a 1000 bp product band was excised from the gel and purified using a QIAquick Gel Extraction Kit according to the manufacturer's instructions.

The purified fragments were used as template DNA for subsequent amplification using primer 993453 (sense) and primer 993456 (antisense) shown above to precisely fuse the 1000 bp fragment comprising the *Trichoderma reesei* cbh1 promoter to the 2586 bp fragment comprising the *Aspergillus oryzae* beta-glucosidase open reading frame by overlapping PCR.

The amplification reactions (50 µl) were composed of Pfx Amplification Buffer, 0.25 mM dNTPs, 6.4 µM primer 99353, 3.2 µM primer 993456, 1 mM MgCl$_2$, and 2.5 units of Pfx DNA polymerase. The reactions were incubated in an Eppendorf Mastercycler 5333 programmed as follows: 30 cycles each for 60 seconds at 94° C., 60 seconds at 60° C., and 240 seconds at 72° C. (15 minute final extension).

Figure 7:
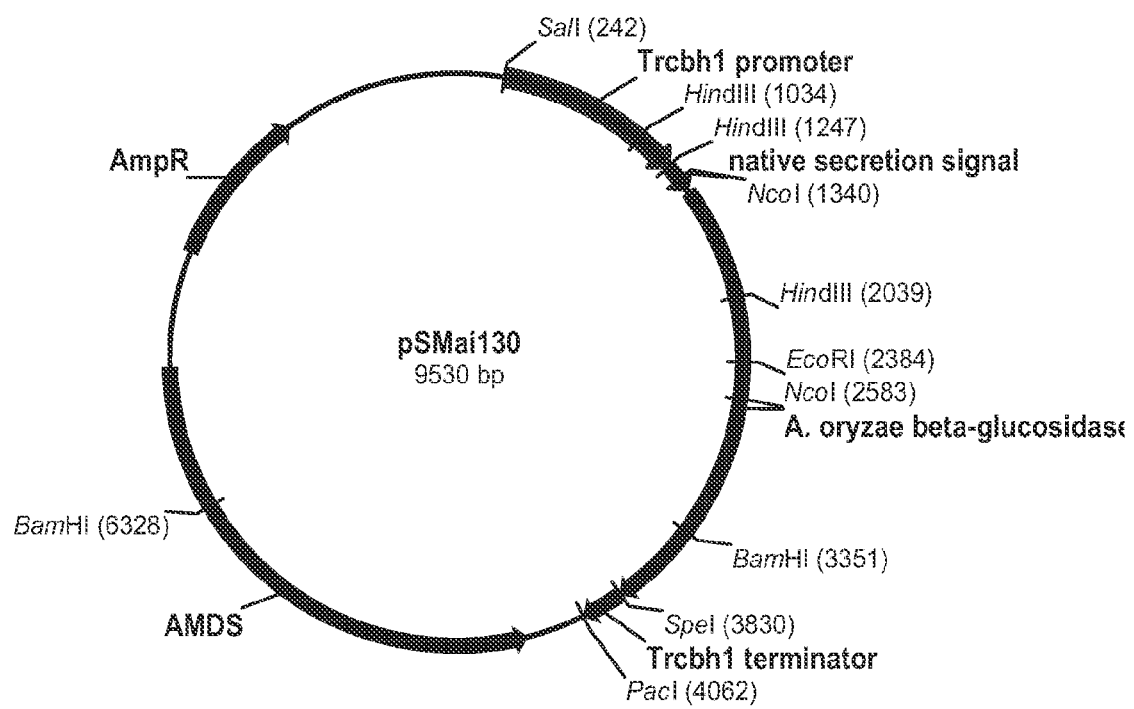
FIG. 7 shows a restriction map of pSMai130.

The resulting 3586 bp fragment was digested with Sal I and Spa I and ligated into pMJ04, digested with the same two restriction enzymes, to generate pSMai130 (FIG. 7).

Example 6

Construction of pSMai135

The *Aspergillus oryzae* beta-glucosidase coding region (minus the native signal sequence, see FIG. 8) from Lys-20 to the TAA stop codon was PCR amplified from pJaL660 as template with primer 993728 (sense) and primer 993727 (antisense) shown below. Sequences in italics are homologous to 20 bp of the *Humicola insolens* endoglucanase V signal sequence and sequences underlined are homologous to 22 bp of the *Aspergillus oryzae* beta-glucosidase coding region. A Spe I site was engineered into the 5' end of the antisense primer.

Primer 993728:
(SEQ ID NO: 30)
5'-*TGCCGGTGTTGGCCCTTGCC*AAGGATGATCTCGCGTACTCCC-3'

Primer 993727:
(SEQ ID NO: 31)
5'-GACTAGTCTTACTGGGCCTTAGGCAGCG-3'

The amplification reactions (50 µl) were composed of Pfx Amplification Buffer, 0.25 mM dNTPs, 10 ng/µl pJal660, 6.4 µM primer 993728, 3.2 µM primer 993727, 1 mM MgCl$_2$, and 2.5 units of Pfx DNA polymerase. The reactions were incubated in an Eppendorf Mastercycler 5333 programmed as follows: 30 cycles each for 60 seconds at 94° C., 60 seconds at 55° C., and 180 seconds at 72° C. (15 minute final extension). The reaction products were isolated on a 1.0% agarose gel using TAE buffer where a 2523 bp product band was excised from the gel and purified using a QIAquick Gel Extraction Kit according to the manufacturer's instructions.

A separate PCR amplification was performed to amplify 1000 bp of the *Trichoderma reesei* cbh1 promoter and 63 bp of the putative *Humicola insolens* endoglucanase V signal sequence (ATG start codon to Ala-21, FIG. 9, SEQ ID NO: 36), using primer 993724 (sense) and primer 993729 (antisense) shown below. Primer sequences in italics are homologous to 20 bp of the *Humicola insolens* endoglucanase V signal sequence and underlined primer sequences are homologous to the 22 bp of the *Aspergillus oryzae* beta-glucosidase coding region. Plasmid pMJ05, which comprises the *Humicola insolens* endoglucanase V coding region under the control of the cbh1 promoter, was used as a template to generate a 1063 bp fragment comprising the *Trichoderma reesei* cbh1 promoter/*Humicola insolens* endoglucanase V signal sequence fragment. A 42 bp of overlap was shared between the *Trichoderma reesei* cbh1 promoter/*Humicola insolens* endoglucanase V signal sequence and the *Aspergillus oryzae* coding sequence to provide a perfect linkage between the promoter and the ATG start codon of the 2523 bp *Aspergillus oryzae* beta-glucosidase, Primer 993724:
(SEQ ID NO: 32)
5'-ACGCGTCGACCGAATGTAGGATTGTTATCC-3'

Primer 993729:
(SEQ ID NO: 33)
5'-GGGAGTACGCGAGATCATCCTT*GGCAAGGGCCAACACCGGCA*-3'

The amplification reactions (50 µl) were composed of Pfx Amplification Buffer, 0.25 mM dNTPs, 10 ng/µl pMJ05, 6.4 µM primer 993728, 3.2 µM primer 993727, 1 mM MgCl$_2$, and 2.5 units of Pfx DNA polymerase. The reactions were incubated in an Eppendorf Mastercycler 5333 programmed as follows: 30 cycles each for 60 seconds at 94° C., 60 seconds at 60° C., and 240 seconds at 72° C. (15 minute final extension). The reaction products were isolated on a 1.0% agarose gel using TAE buffer where a 1063 bp product band was excised from the gel and purified using a QIAquick Gel Extraction Kit according to the manufacturer's instructions.

The purified overlapping fragments were used as a template for amplification using primer 993724 (sense) and primer 993727 (antisense) described above to precisely fuse the 1063 bp fragment comprising the *Trichoderma reesei* cbh1 promoter/*Humicola insolens* endoglucanase V signal sequence to the 2523 bp fragment comprising the *Aspergillus oryzae* beta-glucosidase open reading frame by overlapping PCR.

The amplification reactions (50 µl) were composed of Pfx Amplification Buffer, 0.25 mM dNTPs, 6.4 µM primer 993724, 3.2 µM primer 993727, 1 mM MgCl$_7$, and 2.5 units of Pfx DNA polymerase. The reactions were incubated in an Eppendorf Mastercycler 5333 programmed as follows: 30 cycles each for 60 seconds at 94° C., 60 seconds at 60° C., and 240 seconds at 72° C. (15 minute final extension). The reaction products were isolated on a 1.0% agarose gel using TAE buffer where a 3591 bp product band was excised from the gel and purified using a QIAquick Gel Extraction Kit according to the manufacturer's instructions.

Figure 10:
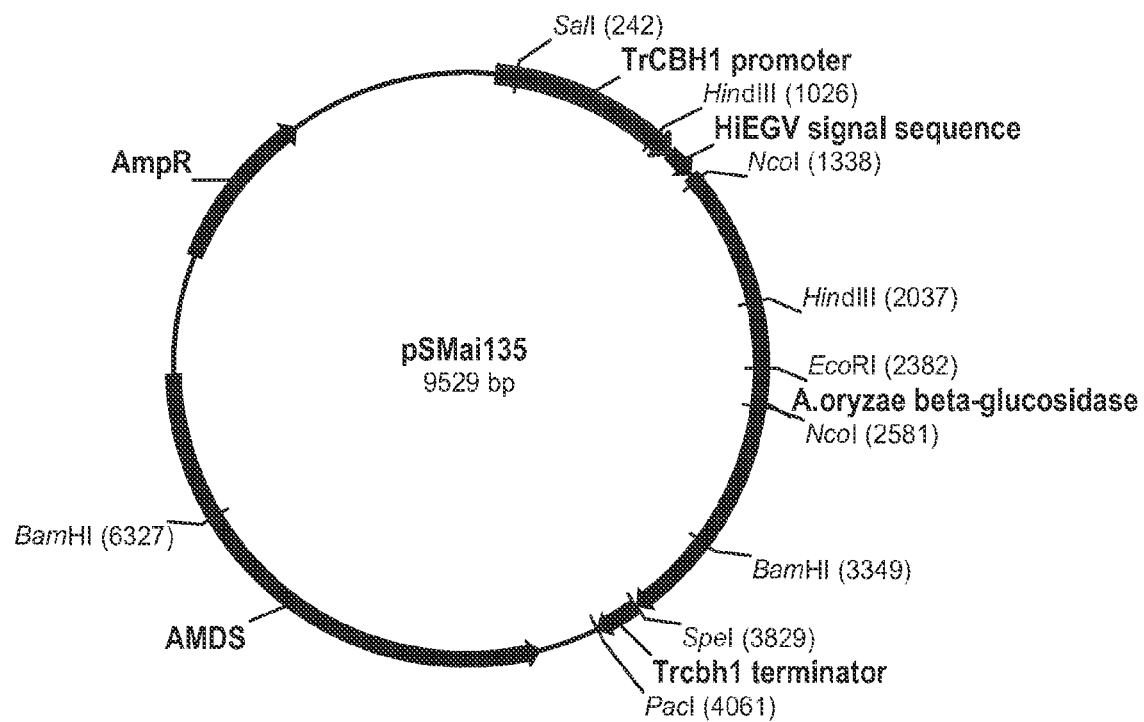
FIG. 10 shows a restriction map of pSMai135.

The resulting 3591 bp fragment was digested with Sal I and Spe I and ligated into pMJ04 digested with the same restriction enzymes to generate pSMail35 (FIG. 10).

Example 7

Expression of *Aspergillus oryzae* Beta-Glucosidase Comparing Native and Heterologous *Humicola insolens* Endoglucanase V Secretion Signal in *Trichoderma reesei*

Plasmid pSMail30, in which the *Aspergillus oryzae* beta-glucosidase is expressed from the cbh1 promoter and native secretion signal (FIG. 8, SEQ ID NOs: 34 (DNA sequence) and 35 (deduced amino acid sequence)), or pSMail35 encoding the mature *Aspergillus oryzae* beta-glucosidase enzyme linked to the *Humicola insolens* endoglucanase V secretion signal (FIG. 9, SEQ ID NOs: 36 (DNA sequence) and 37 (deduced amino acid sequence)), was introduced into *Trichoderma reesei* RutC30 by PEG-mediated transformation (Penttila et al., 1987, supra). Both plasmids contain the *Aspergillus nidulans* amdS gene to enable transformants to grow on acetamide as the sole nitrogen source.

*Trichoderma reesei* RutC30 was cultivated at 27° C. and 90 rpm in 25 ml of YP medium supplemented with 2% (w/v) glucose and 10 mM uridine for 17 hours. Mycelia was collected by filtration using Millipore's Vacuum Driven Disposable Filtration System (Millipore, Bedford, Mass.) and washed twice with deionized water and twice with 1.2 M sorbitol. Protoplasts were generated by suspending the washed mycelia in 20 ml of 1.2 M sorbitol containing 15 mg of Glucanex (Novozymes A/S, Bagsvaerd, Denmark) per ml and 0.36 units of chitinase (Sigma Chemical Co., St. Louis, Mo.) per ml and incubating for 15-25 minutes at 34° C. with gentle shaking at 90 rpm. Protoplasts were collected by centrifuging for 7 minutes at 400×g and washed twice with cold 1.2 M sorbitol. The protoplasts were counted using a haemacytometer and re-suspended in SIC to a final concentration of 1×10$^8$ protoplasts per ml. Excess protoplasts were stored in a Cryo 1° C. Freezing Container (Nalgene, Rochester, N.Y.) at −80° C.

Approximately 7 µg of Pme I digested expression plasmid (pSMail30 or pSMail35) was added to 100 µl of protoplast solution and mixed gently, followed by 260 µl of PEG buffer, mixed, and incubated at room temperature for 30 minutes. STC (3 ml) was then added, mixed and the transformation solution was plated onto COVE plates using *Aspergillus nidu-* lans amdS selection. The plates were incubated at 28° C. for 5-7 days. Transformants were sub-cultured onto COVE2 plates and grown at 28° C.

One hundred and ten amdS positive transformants were obtained with pSMai130 and 65 transformants with pSMai135. Twenty transformants designated SMA130 obtained with pSMai130 (native secretion signal) and 67 transformants designated SMA135 obtained with pSMai135 (heterologous secretion signal) twere subcultured onto fresh plates containing acetamide and allowed to sporulate for 7 days at 28° C.

The 20 SMA130 and 67 SMA135 *Trichoderma reesei* transformants were cultivated in 125 ml baffled shake flasks containing 25 ml of cellulase-inducing media at pH 6.0 inoculated with spores of the transformants and incubated at 28° C. and 200 rpm for 7 days, *Trichoderma reesei* RutC30 was run as a control. Culture broth samples were removed at day 7. One ml of each culture broth was centrifuged at 15,700×g for 5 minutes in a micro-centrifuge and the supernatants transferred to new tubes. Samples were stored at 4° C. until enzyme assay. The supernatants were assayed for beta-glucosidase activity using p-nitrophenyl-beta-D-glucopyranoside as substrate, as described above.

All 20 SMA130 transformants exhibited equivalent beta-glucosidase activity to that of the host strain, *Trichoderma reesei* RutC30. In contrast, a number of SMA135 transformants showed beta-glucosidase activities several-fold more than that of *Trichoderma reesei* RutC30. Transformant SMA135-04 produced the highest beta-glucosidase activity having 7 times more beta-glucosidase activity than produced by *Trichoderma reesei* RutC30 as a control.

SDS-PAGE was carried out using Criterion Tris-HCl (5% resolving) gels (BioRad, Hercules, Calif.) with The Criterion System (BioRad, Hercules, Calif.). Five µl of day 7 supernatants (see above) were suspended in 2× concentration of Laemmli Sample Buffer (BioRad, Hercules, Calif.) and boiled in the presence of 5% beta-mercaptoethanol for 3 minutes. The supernatant samples were loaded onto a polyacrylamide gel and subjected to electrophoresis with 1× Tris/Glycine/SDS as running buffer (BioRad, Hercules, Calif.). The resulting gel was stained with BioRad's Bio-Safe Coomassie Stain.

No beta-glucosidase protein was visible by SDS-PAGE for the *Trichoderma reesei* SMA130 transformant culture broth supernatants. In contrast, 26 of the 38 *Trichoderma reesei* SMA135 transformants produced a protein of approximately 110 kDa that was not visible in *Trichoderma reesei* RutC30 as control. Transformant *Trichoderma reesei* SMA135-04 produced the highest level of beta-glucosidase.

Example 8

Fermentation of *Aspergillus oryzae* SMA135-04

Fermentation was performed on *Aspergillus oryzae* SMA135-04 to determine the production level of beta-glucosidase activity. *Trichoderma reesei* RutC30 (host strain) was run as a control. Spores of *Trichoderma reesei* SMA135-04 were inoculated into 500 ml shake flasks, containing 100 ml of Inoculum Medium. The flasks were placed into an orbital shaker at 28° C. for approximately 48 hours at which time 50 ml of the culture was inoculated into 1.8 liters of Fermentation Medium (see above) in a 2 liter fermentation vessel. The fermentations were run at a pH of 5.0, 28° C., with minimum dissolved oxygen at a 25% at a 1.0 VVM air flow and an agitation of 1100. Feed Medium was administrated into the fermentation vessel at 18 hours with a feed rate of 3.6 g/hour for 33 hours and then 7.2 g/hour. The fermentations ran for 165 hours at which time the final fermentation broths were centrifuged and the supernatants stored at −20° C. until beta-glucosidase activity assay using the procedure described earlier.

Beta-glucosidase activity on the *Trichoderma reesei* SMA135-04 fermentation sample was determined to be approximately 8 times more active than that of *Trichoderma reesei* RutC30.

Example 9

Construction of pSATe111 and pALFd1 *Saccharomyces cerevisiae* Expression Vectors A 2,605 bp DNA fragment comprising the region from the ATG start codon to the TAA stop codon of the *Aspergillus oryzae* beta-glucosidase coding sequence (SEQ ID NO: 42 for cDNA sequence and SEQ ID NO: 43 for the deduced amino acid sequence) was amplified by PCR from pJaL660 (WO 2002/095014) as template with primers 992127 (sense) and 992328 (antisense) shown below:

```
992127:
                                         (SEQ ID NO: 38)
5'-GCAGATCTACCATGAAGCTTGGTTGGATCGAG-3'

992328:
                                         (SEQ ID NO: 39)
5'-GCCTCAGATTACTGGGCCTTAGGCAGCGAG-3'
```

Primer 992127 has an upstream BglII site and the primer 992328 has a downstream Xho I site.

Figure 11:
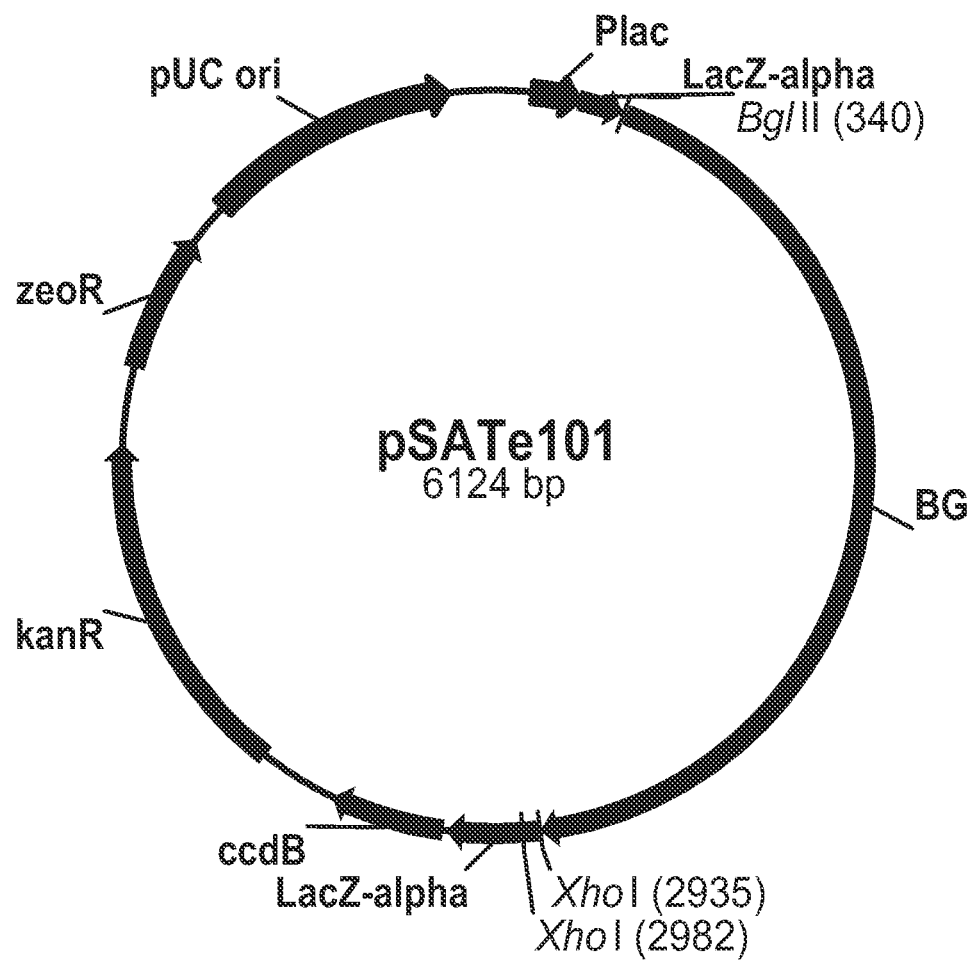
FIG. 11 shows a restriction map of pSATe101.

The amplification reactions (50 µl) were composed of 1×PCR buffer containing $MgCl_2$ (Roche Applied Science, Manheim, Germany), 0.25 mM dNTPs, 50 µM primer 992127, 50 µM primer 992328, 80 ng of pJaL660, and 2.5 units of Pwo DNA Polymerase (Roche Applied Science, Manheim, Germany). The reactions were incubated in an Eppendorf Mastercycler 5333 programmed for 1 cycle at 94° C. for 5 minutes followed by 25 cycles each at 94° C. for 60 seconds, 55° C. for 60 seconds, and 72° C. for 120 seconds (10 minute final extension). The PCR product was then subcloned into the pCR-Blunt II-TOPO vector using the ZeroBlunt™ TOPO PCR Cloning Kit (Invitrogen, Carlsbad, Calif.) following the manufacturer's instructions to generate plasmid pSATe101. (FIG. 11). Plasmid pSATe101 was digested with Bgl II and Xho I to liberate the beta-glucosidase gene. The reaction products were isolated on a 1.0% agarose gel using TAE buffer where a 2.6 kb product band was excised from the gel and purified using a QIAquick Gel Extraction Kit according to the manufacturer's instructions.

Figure 12:
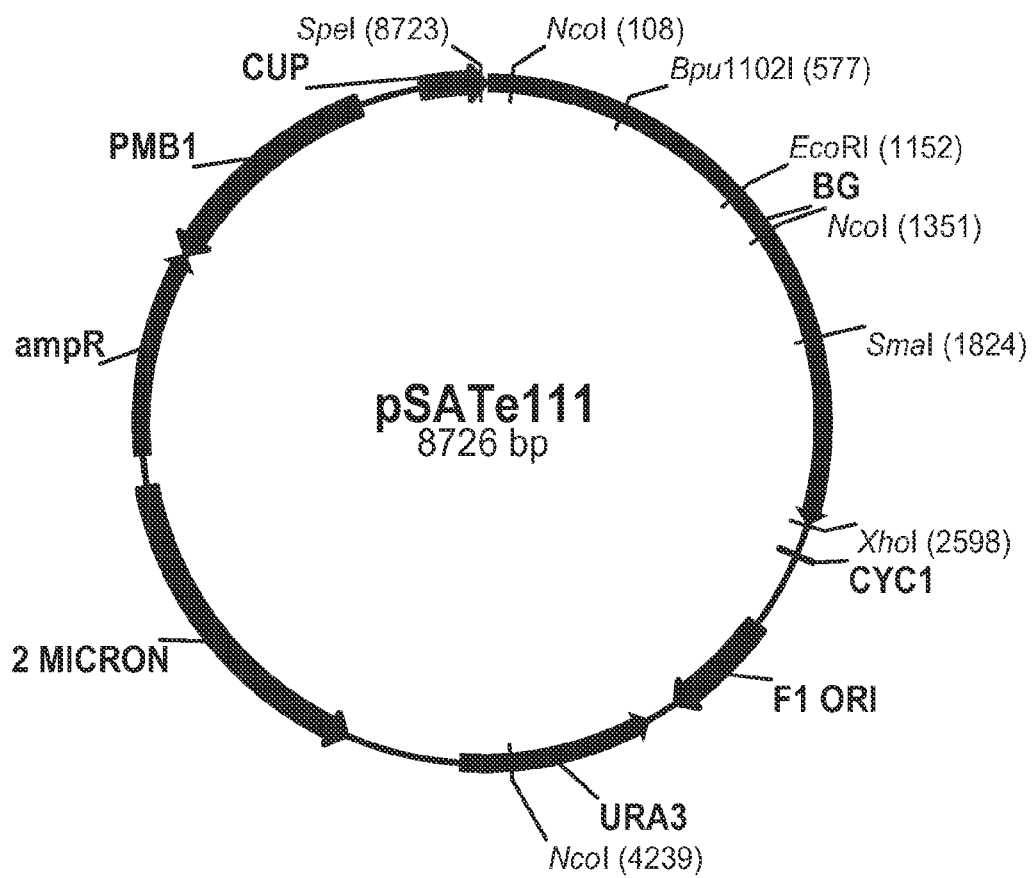
FIG. 12 shows a restriction map of pSATe111.

The 2.6 kb PCR product was digested and cloned into Sam HI and Xho I sites of the copper inducible 2 µm yeast expression vector pCu426 (Labbe and Thiele, 1999, *Methods Enzymol* 306: 145-53), to generate pSATe111 (FIG. 12).

Plasmid pALFd1 was constructed to determine if enhanced *Aspergillus oryzae* beta glucosidase production and secretion could also be achieved in *Saccharomyces cerevisiae* by swapping the native *Aspergillus oryzae* beta-glucosidase secretion signal with the *Humicola insolens* endoglucanase V signal peptide.

Plasmid pSATe111 was digested with Xho I and Spe I to release 2.6 kb (*Aspergillus oryzae* beta-glucosidase) and 6 kb (rest of the vector) fragments. The 6 kb fragment was isolated and ligated to the 2.6 kb PCR fragment, containing the *Aspergillus oryzae* beta-glucosidase coding region (minus the secretion signal sequence) and the *Humicola insolens* endoglucanase V signal sequence, which was amplified from pSMail35 using primers 993950 and 993951 shown below. The primers contain the Xho I and Spe I restriction sites at their ends for subsequent subcloning into the Xho I and Spe I restriction sites of pSATe111.

```
Primer 993950:
                                         (SEQ ID NO: 40)
5'-AATCCGACTAGTGGATCTACCATGCGTTCCTCCCCCCTCC-3'

Primer 993951:
                                         (SEQ ID NO: 41)
5'-GCGGGCCTCGAGTTACTGGGCCTTAGGCAGCG-3'
```

Figure 13:
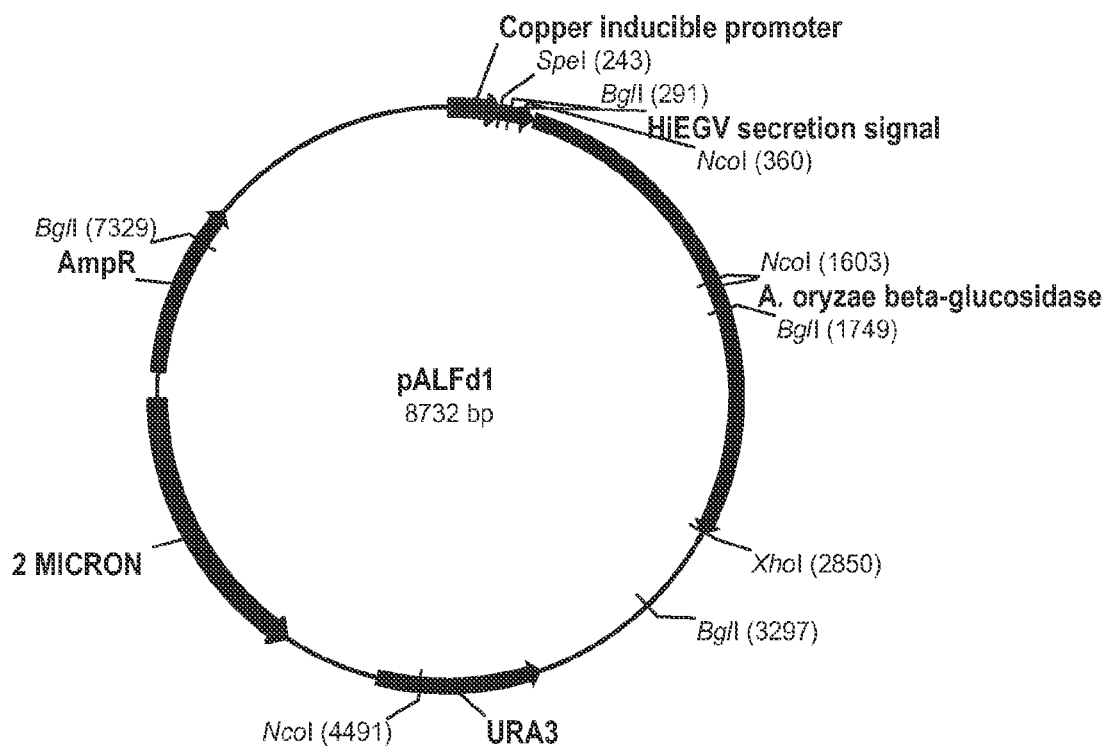
FIG. 13 shows a restriction map of pALFd1.

The amplification reactions (100 µl) were composed of PCR Thermo Pol Buffer, 0.20 mM dNTPs, 0.14 µg of pSMail35 plasmid DNA, 50 µM primer 993950, 50 µM primer 993951, and 2 units of Vent DNA polymerase. The reactions were incubated in a RoboCycler Gradient 40 Thermal Cycler (Stratagene, La Jolla, Calif.) programmed as follows: one cycle of 1 minute at 95° C., 25 cycles each for 1 minute at 95° C., 1 minute at 60 or 64° C., and 3 minutes at 72° C. (10 minute final extension). The reaction products were visualized on a 0.7% agarose gel using TAE buffer. The resulting 2.6 kb fragment bands were purified using a PCR MinElute PCR Purification (QIAGEN, Chatsworth, Calif.) according to the manufacturer's instructions. The purified fragments were combined and digested with Xho I and Spe I and ligated into pSATe111 digested with the same two restriction enzymes to generate pALFd1 (FIG. 13).

Example 10

Expression of *Aspergillus oryzae* Beta-Glucosidase Comparing Native and Heterologous Secretion Signal in *Saccharomyces cerevisiae*

Plasmid pALFd1 (approximately 600 ng) was transformed into freshly made *Saccharomyces cerevisiae* YNG 318 competent cells according to the YEASTMAKER Yeast Transformation Protocol, CLONTECH Laboratories, Inc., Palo Alto, Calif. Transformed cells were plated onto yeast selection plates containing 0.15 mg of the chromogenic substrate 5-bromo-4-chloro-3-indolyl-beta-D-glucopyranoside per ml, which yield blue colonies when beta-glucosidase is present. The plates were incubated at 30° C. for 4 days.

Colonies harboring the expression vector with the *Humicola insolens* endoglucanase V secretion signal were generally darker blue in color than the colonies that had the native *Aspergillus oryzae* beta-glucosidase signal sequence, indicating that more *Aspergillus oryzae* beta-glucosidase was secreted using the *Humicola insolens* endoglucanase V secretion signal. Approximately, 242 blue colonies from both constructs were picked using an automated colony picker (QPix, Genetix USA, Inc., Boston, Mass.). The 242 transformants were inoculated into yeast selection medium (which contains copper) to induce expression and secretion of *Aspergillus oryzae* beta-glucosidase. Broth from day 7 96-well culture was taken from each of the 245 colonies and assayed for beta-glucosidase activity using p-nitrophenyl-beta-D-glucopyranoside as substrate as described above. The results showed that colonies expressing beta-glucosidase with the heterologous signal sequence were 6.6 times more active than the colonies that were transformed with the *Aspergillus oryzae* beta-glucosidase with the native secretion signal.

Example 11

Identification of a Glycosyl Hydrolase Family GH3A Gene in the Genomic Sequence of *Aspergillus fumigatus*

A tblastn search (Altschul et al., 1997, *Nucleic Acids Res.* 25: 3389-3402) of the *Aspergillus fumigatus* partial genome sequence (The Institute for Genomic Research, Rockville, Md.) was carried out using as query a beta-glucosidase protein sequence from *Aspergillus aculeatus* (Accession No. P48825). Several genes were identified as putative Family GH3A homologs based upon a high degree of similarity to the query sequence at the amino acid level. One genomic region of approximately 3000 bp with greater than 70% identity to the query sequence at the amino acid level was chosen for further study.

Example 12

*Aspergillus fumigatus* Genomic DNA Extraction

*Aspergillus fumigatus* PaHa34 was grown in 250 ml of potato dextrose medium in a baffled shake flask at 37° C. and 240 rpm. Mycelia were harvested by filtration, washed twice in TE buffer (10 mM Tris-1 mM EDTA), and frozen under liquid nitrogen. Frozen mycelia were ground by mortar and pestle to a fine powder, which was resuspended in pH 8.0 buffer containing 10 mM Tris, 100 mM EDTA, 1% Triton X-100, 0.5 M guanidine-HCl, and 200 mM NaCl. DNase-free RNase A was added at a concentration of 20 µg/ml and the lysate was incubated at 37° C. for 30 minutes. Cellular debris was removed by centrifugation, and DNA was isolated by using a Qiagen Maxi 500 column (QIAGEN Inc., Chatsworth, Calif.). The columns were equilibrated in 10 ml of QBT washed with 30 ml of QC, and eluted with 15 ml of QF (all buffers from QIAGEN Inc., Chatsworth, Calif.). DNA was precipitated in isopropanol, washed in 70% ethanol, and recovered by centrifugation. The DNA was resuspended in TE buffer.

Example 13

Cloning of the Family GH3A Beta-Glucosidase Gene and Construction of an *Aspergillus oryzae* Expression Vector Two synthetic oligonucleotide primers shown below were designed to PCR amplify an *Aspergillus fumigatus* PaHa34 gene encoding a Family GH3A beta-glucosidase from the genomic DNA prepared in Example 14. An in Fusion Cloning Kit (BD Biosciences, Palo Alto, Calif.) was used to clone the fragment directly into the expression vector, pAILo2 (FIG. 14), without the need for restriction digests and ligation.

```
Forward primer:
                                         (SEQ ID NO: 44)
5'-ACTGGATTTACCATGAGATTCGGTTGGCTCG-3'

Reverse primer:
                                         (SEQ ID NO: 45)
5'-AGTCACCTCTAGTTACTAGTAGACACGGGGC-3'
```

Bold letters represent coding sequence. The remaining sequence is homologous to the insertion sites of pAILo2, described in Example 7.

Fifty picomoles of each of the primers above were used in a PCR reaction containing 100 ng of *Aspergillus fumigatus* genomic DNA, 1×Pfx Amplification Buffer, 1.5 µl of 10 mM blend of dATP, dTTP, dGTP, and dCTP, 2.5 units of Pfx DNA Polymerase, 1 µl of 50 mM MgSO₄ and 2.5 µl of 10×pCRx Enhancer solution (Invitrogen, Carlsbad, Calif.) in a final volume of 50 µl. The reactions were incubated in an Eppendorf Mastercycler 5333 programmed as follows: one cycle at 94° C. for 2 minutes; and 30 cycles each at 94° C. for 15 seconds, 55° C. for 30 seconds, and 68° C. for 3 minutes. The heat block then went to a 4° C. soak cycle.

The reaction products were isolated on a 1.0% agarose gel using TAE buffer where a 3 kb product band was excised from the gel and purified using a QIAquick Gel Extraction Kit according to the manufacturer's instructions.

The fragment was then cloned into the pAlLo2 expression vector using an Infusion Cloning Kit. The vector was digested with Nco I and Pac I. The fragment was purified by gel electrophoresis and Qiaquick gel purification. The gene fragment and digested vector were ligated together in a reaction resulting in the expression plasmid pEJG97 (FIG. 15) in which transcription of the Family GH3A beta-glucosidase gene was under the control of the NA2-tpi promoter. The ligation reaction (50 µl) was composed of 1× InFusion Buffer (BD Biosciences, Palo Alto, Calif.), 1×BSA (BD Biosciences, Palo Alto, Calif.), 1 µl of Infusion enzyme (diluted 1:10) (BD Biosciences, Palo Alto, Calif.), 150 ng of pAlLo2 digested with Nco I and Pac I, and 50 ng of the *Aspergillus fumigatus* beta-glucosidase purified PCR product. The reaction was incubated at room temperature for 30 minutes. One µl of the reaction was used to transform *E. coli* XL10 Solopac Gold cells (Stratagene, La Jolla, Calif.). An *E. coli* transformant containing the pEJG97 plasmid was detected by restriction digestion of the plasmid DNA.

Example 14

Figure 16A:
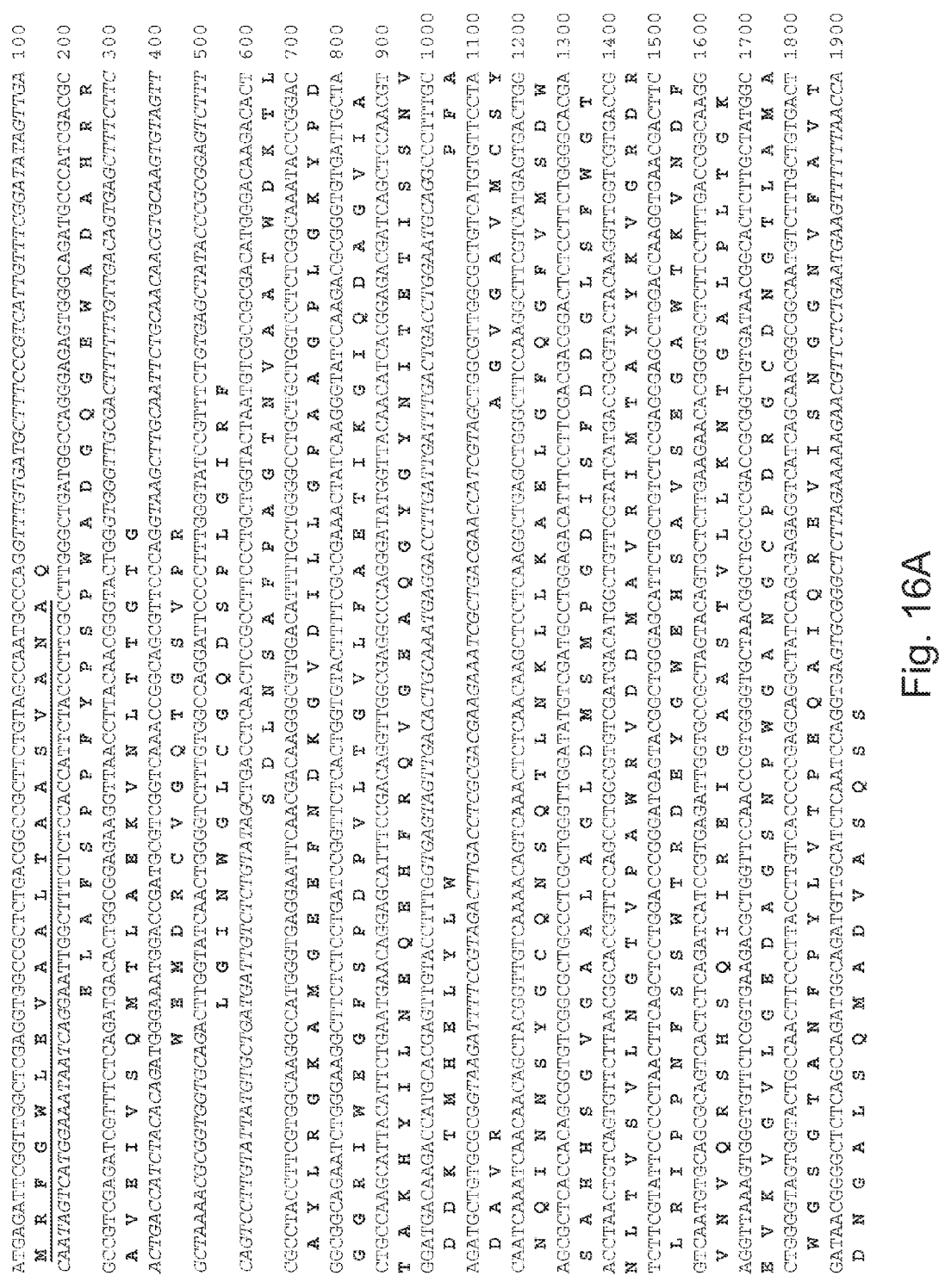
Figure 16B:
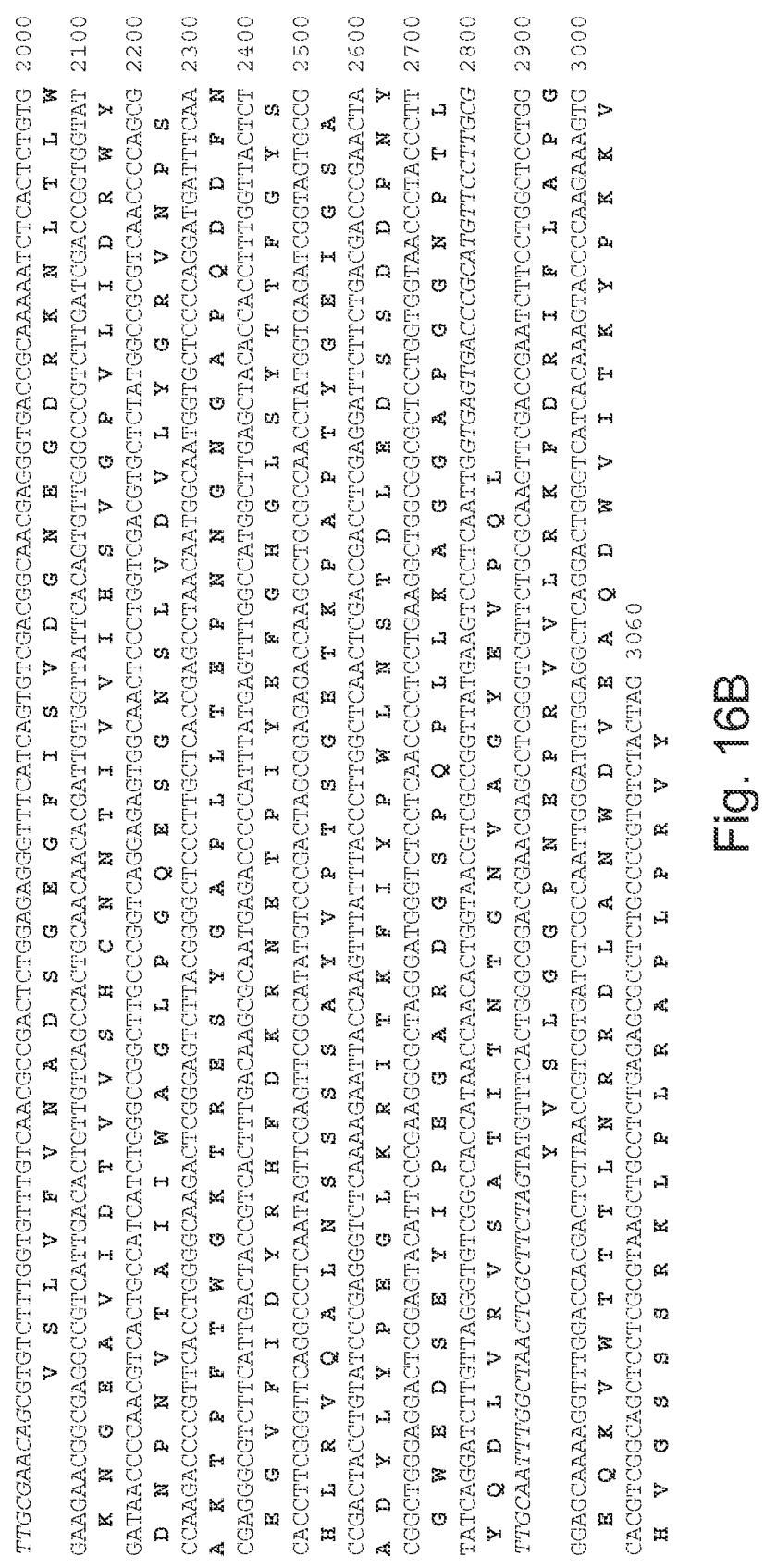

Characterization of the *Aspergillus fumigatus* Genomic Sequence Encoding a Family GH3A Beta-Glucosidase DNA sequencing of the *Aspergillus fumigatus* beta-glucosidase gene from pEJG97 was performed as described previously using a primer walking strategy. A gene model for the *Aspergillus fumigatus* sequence was constructed based on similarity to homologous genes from *Aspergillus aculeatus*, *Aspergillus niger*; and *Aspergillus kawachii*. The nucleotide sequence (SEQ ID NO: 46) and deduced amino acid sequence (SEQ ID NO: 47) are shown in FIG. 16. The genomic fragment encodes a polypeptide of 863 amino acids, interrupted by 8 introns of 62, 55, 58, 63, 58, 58, 63 and 51 bp. The % G+C content of the gene is 54.3%. Using the SignalP software program (Nielsen et al., 1997, *Protein Engineering* 10:1-6), a signal peptide of 19 residues was predicted. The predicted mature protein contains 844 amino acids with a molecular mass of 91.7 kDa.

A comparative alignment of beta-glucosidase sequences was determined using the Clustal W method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Aspergillus fumigatus* beta-glucosidase gene shares 78%, 76%, and 76% identity to the deduced amino acid sequences of the *Aspergillus aculeatus* (accession number P48825), *Aspergillus niger* (accession number 000089), and *Aspergillus kawachii* (accession number P87076) beta-glucosidases.

Example 15

Expression of the *Aspergillus fumigatus* Family GH3A Beta-Glucosidase Gene in *Aspergillus oryzae* JAL250

*Aspergillus oryzae* Jal250 protoplasts were prepared according to the method of Christensen et al., 1988, *Bio/Technology* 6: 1419-1422. Five µg of pEJG97 (as well as pAlLo2 as a vector control) was used to transform *Aspergillus oryzae* JAL250.

The transformation of *Aspergillus oryzae* Jal250 with pEJG97 yielded about 100 transformants. Ten transformants were isolated to individual PDA plates.

Confluent PDA plates of five of the ten transformants were washed with 5 ml of 0.01% Tween 20 and inoculated separately into 25 ml of MDU2BP medium in 125 ml glass shake flasks and incubated at 34° C., 250 rpm. Five days after incubation, 0.5 µl of supernatant from each culture was analyzed using 8-16% Tris-Glycine SDS-PAGE gels (invitrogen, Carlsbad, Ga.) according to the manufacturer's instructions. SDS-PAGE profiles of the cultures showed that one of the transformants (designated transformant 1) had a major band of approximately 130 kDa.

Example 16

Extraction of Total RNA from *Aspergillus oryzae*

The *Aspergillus oryzae* transformant described in Example 13 was frozen in liquid nitrogen and stored at −80° C. Subsequently, the frozen tissue was ground in an electric coffee grinder with a few chips of dry ice added to keep the powdered mycelia frozen. Then, the ground material was transferred with a spatula to a 50 ml sterile conical tube which had been previously filled with 20 ml of Fenozol (Active Motif, Inc., Carlsbad, Calif.). The mixture was mixed rapidly to dissolve the frozen material to a thick solution, and placed in a 50° C. water bath for 15 minutes. Five ml of RNase-free chloroform was added to the mixture and vortexed vigorously. Then, the mixture was allowed to stand at room temperature for 10 minutes. Next the mixture was centrifuged at 1300×g in a Sorvall RT7 centrifuge (Sorvall, Inc, Newtown, Conn.) at room temperature for 20 minutes. The top phase was transferred to a new conical tube and an equal volume of phenol-chloroform-isoamylalcohol (25:24:1) was added. The mixture was vortexed and centrifuged for 10 minutes. This procedure was repeated twice so that three phenol-chloroform isoamylalcohol extractions were done. Then, the top phase was transferred to a new tube and an equal volume of chloroform:isoamylalcohol (24:1) was added. The mixture was vortexed once again and centrifuged for 10 minutes. After centrifugation, the aqueous phase (approximately 5 ml) was transferred to a new Oak Ridge tube and 0.5 ml of 3 M sodium acetate pH 5.2 and 6.25 ml of isopropanol were added. The mixture was mixed and incubated at room temperature for 15 minutes. Subsequently, the mixture was centrifuged at 12,000×g for 30 minutes, at 4° C. in a Sorvall RC5B (Sorvall, Inc, Newtown, Conn.). Following centrifugation, the supernatant was removed and 18 ml of 70% ethanol was carefully added to the pellet. Another centrifugation step was done for 10 minutes at 4° C. at 12,000×g. The supernatant was carefully removed and the pellet was air dried. The RNA pellet was resuspended in 500 µl of diethyl pyrocarbonate (DEPC)-treated water. Heating at 65° C. for 10 minutes aided in resuspension. The total RNA was stored at −80° C. Quantitation and assessing RNA quality was done on an Agilent Bioanalyzer 2100 (Englewood, Colo.) using RNA chips. All the materials and reagents used in this protocol were RNAse-free.

Example 17

Cloning of the *Aspergillus fumigatus* Beta-Glucosidase cDNA Sequence

The total RNA described in Example 16 was used to clone the *Aspergillus fumigatus* beta-glucosidase cDNA sequence (SEQ ID NO: 48 for cDNA sequence and SEQ ID NO: 49 for the deduced amino acid sequence). The mRNA from the total RNA was purified using a Poly(A)Purist Mag Kit (Ambion, Inc., Austin, Tex.) following the manufacturer's instructions. The *Aspergillus fumigatus* beta-glucosidase cDNA sequence, was then amplified in two fragments: a 1,337 bp DNA fragment spanning from the ATG start codon to the 1,332 position (labeled as 5' fragment) and a second 1,300 bp DNA fragment (labeled 3' fragment) spanning from the 1,303 position until the stop codon using the ProStar UltraHF RT-PCR System (Stratagene, La Jolla, Calif.), following the manufacturer's protocol for a 50 µl reaction using 200 ng of poly-A mRNA with primes Afuma (sense) and Afumc (antisense) for the 5' fragment and primers Afumd (sense) and Afumb (antisense) for the 3' fragment as shown below:

```
Afuma:
                                        (SEQ ID NO: 50)
5'-GGCTCATGAGATTCGGTTGGCTCGAGGTC-3'

Afumc:
                                        (SEQ ID NO: 51)
5'-GCCGTTATCACAGCCGCGGTCGGGGCAGCC-3'

Afumd:
                                        (SEQ ID NO: 52)
5'-GGCTGCCCCGACCGCGGCTGTGATAACGGC-3'

Afumb:
                                        (SEQ ID NO: 53)
5'-GCTTAATTAATCTAGTAGACACGGGGCAGAGGCGG-3'
```

Primer Afuma has an upstream Bsp HI site and primer Afumb has a downstream Pac I site. Twenty nine nucleotides at the 3'-end of the 1,337 fragment overlapped with the 5'-end of the 1,303 fragment. In the overlap region there was a unique Sac II site.

Figure 17:
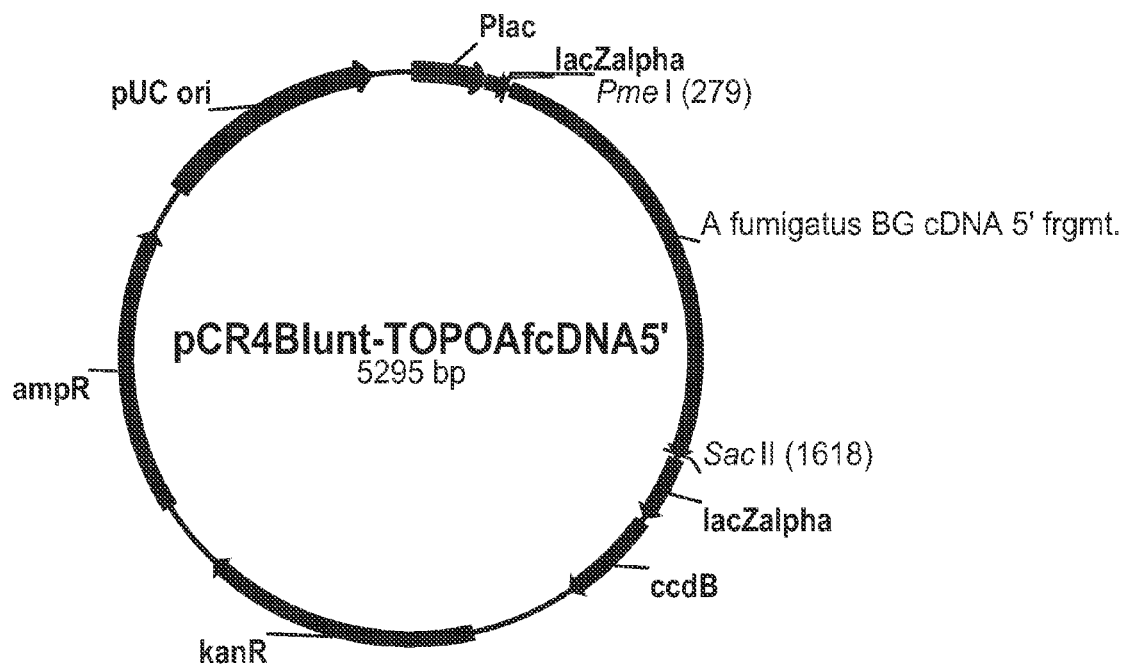
FIG. 17 shows a restriction map of pCR4Blunt™-TOPOAfcDNA5'.
Figure 18:
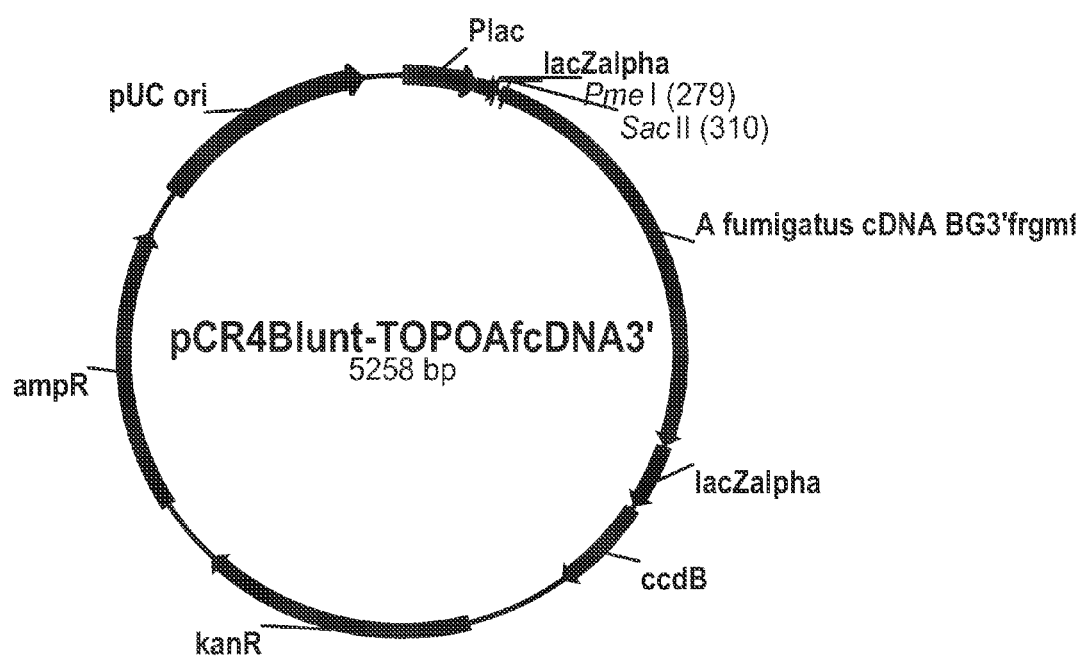
FIG. 18 shows a restriction map of pCR4Blunt-TOPOAfcDNA3'.

Both fragments were subcloned individually into the pCR-BluntII-TOPO vector using a Zero Blunt™ TOPED PCR Cloning Kit for sequencing, following the manufacturer's protocol, generating plasmids pCR4Blunt-TOPOAfcDNA5' (FIG. 17) and pCR4Blunt-TOPOAfcDNA3' (FIG. 18), containing the 5' and 3' fragments, respectively.

The entire coding region of both *Aspergillus fumigatus* beta-glucosidase fragments was confirmed by sequencing using 0.5 µl of each plasmid DNA and 3.2 pmol of the following primers:

```
BGLU1.for:
                                        (SEQ ID NO: 54)
5'-ACACTGGCGGAGAAGG-3'

BGLU2.for:
                                        (SEQ ID NO: 55)
5'-GCCCAGGGATATGGTTAC-3'

-continued
BGLU3.for:
                                        (SEQ ID NO: 56)
5'-CGACTCTGGAGAGGGTTTC-3'

BGLU4.rev:
                                        (SEQ ID NO: 57)
5'-GGACTGGGTCATCACAAAG-3'

BGLU5.rev:
                                        (SEQ ID NO: 58)
5'-GCGAGAGGTCATCAGCA-3'

M13 forward:
                                        (SEQ ID NO: 59)
5'-GTAAAACGACGGCCAGT-3'

M13 reverse:
                                        (SEQ ID NO: 60)
5'-CAGGAAACAGCTATGA-3'
```

Sequencing results indicated the presence of several nucleotide changes when comparing the *Aspergillus fumigatus* beta-glucosidase cDNA sequence obtained to the *Aspergillus fumigatus* beta-glucosidase cDNA sequence deduced from genome data of The Institute for Genomic Research (Rockville, Md.). At position 500, T was replaced by C, so that the coding sequence GTT was changed to GCT, so that valine was replaced by alanine. At position 903, T was replaced by C, so that the coding sequence CCC was changed to CCT, however, this change was silent. At position 2,191, G was replaced by C, so that the coding sequence CAG was changed to GAG, so that glutamic acid was replaced by glutamine. Finally, at position 2,368, C was replaced by T, so that the coding sequence CTG was changed to TTG, however, this change was also silent.

Once the two fragments had been sequenced, both clones containing each fragment were digested using approximately 9 µg of each plasmid DNA with Sac II and Pme I. Digestion of the pCR4Blunt-TOPOAfcDNA5' vector with the above enzymes generated a fragment of 3,956 bp (containing most of the vector) and a second fragment of and 1,339 bp (containing the *Aspergillus fumigatus* beta-glucosidase cDNA 5' fragment). Digestion of the pCR4Blunt-TOPOAfcDNA3' vector with these same enzymes generated a 5,227 bp fragment (containing most of the pCR4Blunt-TOPO vector and the *Aspergillus fumigatus* beta-glucosidase cDNA 3' fragment) and a second fragment of 31 bp.

Figure 19:
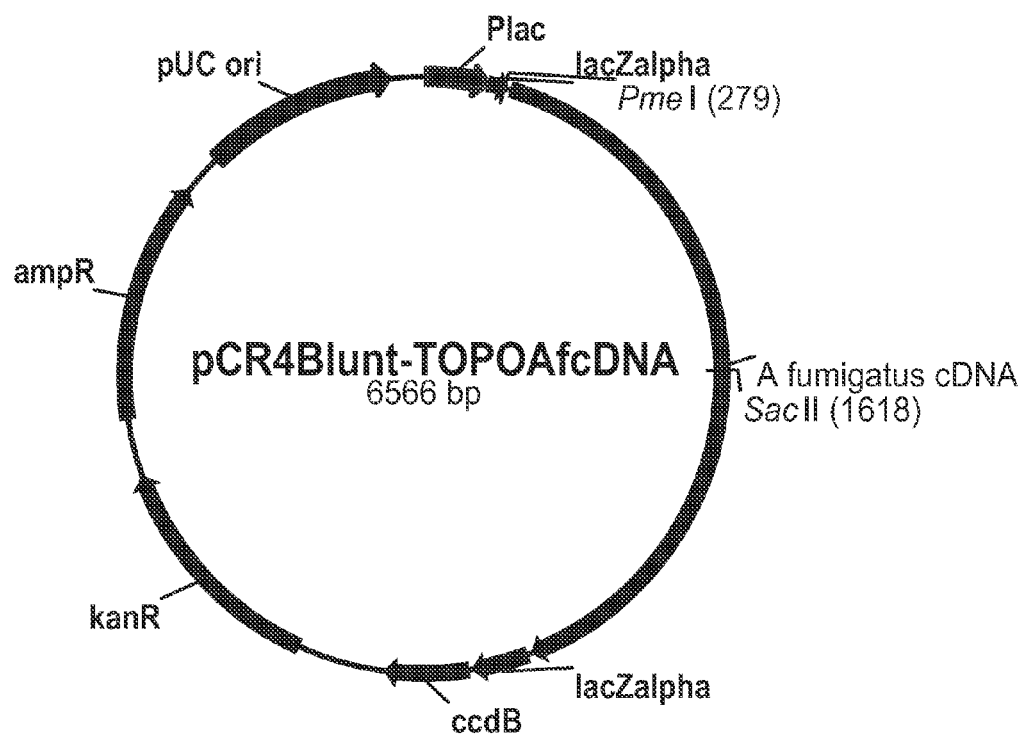
FIG. 19 shows a restriction map of pCR4Blunt-TOPOAfcDNA.

Digested pCR4Blunt-TOPOAfcDNA3' was treated with shrimp alkaline phosphatase for dephosphorylation of the digested DNA products by adding 1×SAP buffer and 1 µl of shrimp alkaline phosphatase (Roche Applied Science, Manheim, Germany) and incubating the reaction for 10 minutes at 37° C. followed by incubation at 85° C. for 10 minutes for enzyme inactivation. Both digestions were run on 0.7% agarose gel with TAE buffer and purified using a QIAGEN Gel Purification Kit according to the manufacturer's instructions. The 1,339 bp and generated from the pCR4Blunt-TOPOAfcDNA5' digestion and the 5,227 bp fragment generated from the pCR4Blunt-TOPOAfcDNA3' digestion were ligated by using the Rapid DNA Ligation Kit (Roche Applied Science, Manheim, Germany) following the manufacturer's instructions. The ligation reaction was transformed into XL1-Blue *E. coli* subcloning-competetent cells according to the manufacturer's instructions (Stratagene, La Jolla, Calif.). Upon transformation, plasmid DNA from an isolated colony was sequenced to confirm that both the 5' and 3' fragments of the *Aspergillus fumigatus* beta-glucosidase cDNA were subcloned in tandem generating a 6,566 bp pCR4Blunt-TOPOAfcDNA vector (FIG. 19).

Example 18

Construction of the pALFd6 and pALFd7 Sacharomyces cerevisiae Expression Vectors The *Aspergillus fumigatus* beta-glucosidase full length cDNA was amplified by PCR using the following primers that have homology to pCu426 and the 5' and 3' sequences of the *Aspergillus fumigatus* beta-glucosidase DNA:

AfumigatusBGUpper:
(SEQ ID NO: 61)
5'-CTTCTTGTTAGTGCAATATCATATAGAAGTCATCGACTAGTGGATC

TACCATGAGATTGGTTGGCTCG-3'

ATGAGATTCGGTTGGCTCG has homology to the 5' end of the Aspergillus fumigatus cDNA AfumigatusBGLower:
(SEQ ID NO: 62)
5'-GCGTGAATGTAAGCGTGACATAACTAATTACATGACTCGAGCTAGT

AGACACGGGGCAGAG-3'

CTAGTAGACACGGGGCAGAG has homology to the 3' end of the Aspergillus fumigatus cDNA The amplification reaction (100 µl) was composed of 0.5 µl of the pCR4Blunt-TOPOAfcDNA plasmid containing the *Aspergillus fumigatus* cDNA sequence, 1×Pfx Amplification Buffer, 50 µM each of dATP, dCTP, dGTP, and dTTP, 50 pmole of each above primer, 1.5 mM MgSO$_4$, and 2.5 units of Platinum Pfx DNA polymerase. The reactions were incubated in an RoboCycler Gradient 40 programmed for 1 cycle at 95° C. for 5 minutes; 25 cycles each at 95° C. for 1 minute, 50° C. for 1 minute; and 72° C. for 3 minutes; and a final extension cycle at 72° C. for 10 minutes. The PCR reaction was purified using a QIAquick PCR Purification Kit (QIAGEN Inc., Valencia, Calif.). DNA was eluted into 30 µl of EB buffer (QIAGEN Inc., Valencia, Calif.). The PCR product comprised 37 bp of homologous DNA sequence which was mixed with 1 µl of pCU426 gapped with Spe I and Xho I for cotransformation into *Saccharomyces cerevisiae* YNG318 competent cells as described in Example 10. These colonies did not turn blue, suggesting some sequencing error in the *Aspergillus fumigatus* beta-glucosidase cDNA sequence. Further sequencing of the *Aspergillus fumigatus* cDNA sequence indicated an insertion of an extra nucleotide in the cDNA sequence, which disrupted the open-reading frame of the enzyme. Therefore, this construct had to be fixed.

Simultaneously to expressing the *Aspergillus fumigatus* beta-glucosidase cDNA in *Saccharomyces cerevisiae*, the *Humicola insolens* endoglucanase V signal sequence was swapped with the native signal sequence of the *Aspergillus fumigatus* cDNA sequence also for expression in *Saccharomyces cerevisiae* to compare the expression of the enzymes with both signal sequences. The *Aspergillus fumigatus* cDNA sequence was amplified by PCR with a primer that has homology to the *Humicola insolens* endoglucanase V signal sequence in pALFd1 as well as homology to the 5'-end of the mature *Aspergillus fumigatus* beta-glucosidase cDNA sequence. The primers used for amplification of the *Aspergillus fumigatus* beta-glucosidase cDNA sequence are the AfumigatusBGLower primer described before and the HiEGVAfumigatus primer described below:

HIEGVAfumigatus:
(SEQ ID NO: 63)
5'-CCGCTCCGCCGTTGTGGCCGCCCTGCCGGTGTTGGCCCTTGCCGAA

TTGGCTTTCTCTCC-3'

GAATTGGCTTTCTCTCC has homology to the 5' end of the Aspergillus fumigatus mature sequence.

Figure 20:
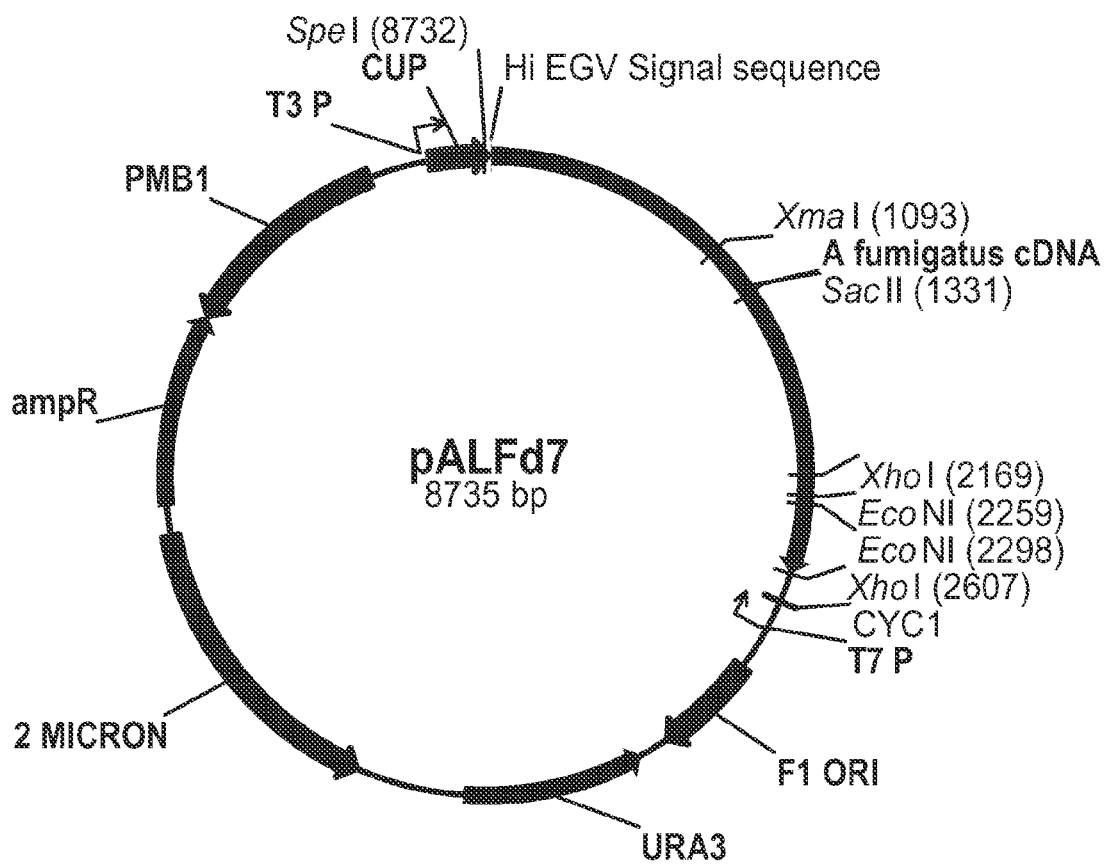
FIG. 20 shows a restriction map of pALFd7.

The amplification reaction (100 µl) was composed of 0.5 µl of the pCR4Blunt-TOPOAfcDNA plasmid containing the *Aspergillus fumigatus* cDNA sequence, 1×Pfx Amplification Buffer, 50 µM each of dATP, dCTP, dGTP, and dTTP, 50 pmole of each above primer, 1.5 mM MgSO$_4$, and 2.5 units of Platinum Pfx DNA polymerase. The reactions were incubated in an RoboCycler Gradient 40 programmed for 1 cycle at 95° C. for 5 minutes; 25 cycles each at 95° C. for 1 minute, 50° C. for 1 minute; and 72° C. for 3 minutes; and a final extension cycle at 72° C. for 10 minutes. The PCR reaction was purified using a QIAquick PCR Purification Kit. DNA was eluted into 10 µl of EB buffer. Three ul of the clean-up PCR product was mixed with 1.8 µl of pALFd1 gapped with Eco NI and Xho I for cotransformation into *Saccharomyces cerevisiae* YNG318 competent cells as described in Example 10. These colonies turned light blue. However, one colony stood out by being very blue. DNA rescue from this colony was done according to the protocol described by Kaiser and Auer, 1993, *BioTechniques* 14: 552, except 20 µl of yeast lysis buffer (1% SDS, 10 mM Tris-HCl, 1 mM EDTA pH 8) was used, and the plasmid was transformed into *E. coli* SURE electroporation-competent cells (Stratagene, La Jolla, Calif.) for sequencing. Full-length sequencing indicated the *Aspergillus fumigatus* beta-glucosidase cDNA sequence was correct. This plasmid was designated pALFd7 (FIG. 20), which comprised the *Aspergillus fumigatus* beta-glucosidase cDNA sequence with the *Humicola insolens* endoglucanase V signal sequence for yeast expression.

To produce a yeast expression vector containing the correct *Aspergillus fumigatus* cDNA sequence with its native signal sequence, the region containing the correct nucleotide sequence from the yeast expression vector containing the *Aspergillus fumigatus* cDNA sequence with the *Humicola insolens* endoglucanase V signal sequence (pALFd7) was amplified by PCR using the above BGLU.5rev primer and the following primer:

BGL.7for:
(SEQ ID NO: 64)
5'-CTGGCGTTGGCGCTGTC-3'

The amplification reaction (100 µl) was composed of 0.5 µl of pALFd7, 1×Pfx Amplification Buffer, 50 µM each of dATP, dCTP, dGTP, and dTTP, 50 pmole of each above primer, 1.5 mM MgSO$_4$, and 23 units of Platinum Pfx DNA polymerase. The reactions were incubated in an RoboCycler Gradient 40 programmed for 1 cycle at 95° C. for 5 minutes; 25 cycles each at 95° C. for 1 minute, 50° C. for 1 minute; and 72° C. for 1 minutes; and a final extension cycle at 72° C. for 10 minutes.

The 701 bp PCR fragment was purified using a QIAquick PCR Purification Kit. DNA was eluted into 10 µl of EB buffer. Three ul of the clean-up PCR product was mixed with 3 µl of the yeast expression vector containing the *Aspergillus fumigatus* cDNA sequence with the native signal sequence and the extra nucleotide gapped with the Sac II and Xma I vector for cotransformation into *Saccharomyces cerevisiae* YNG318 competent cells as described as described in Example 10.

Figure 21:
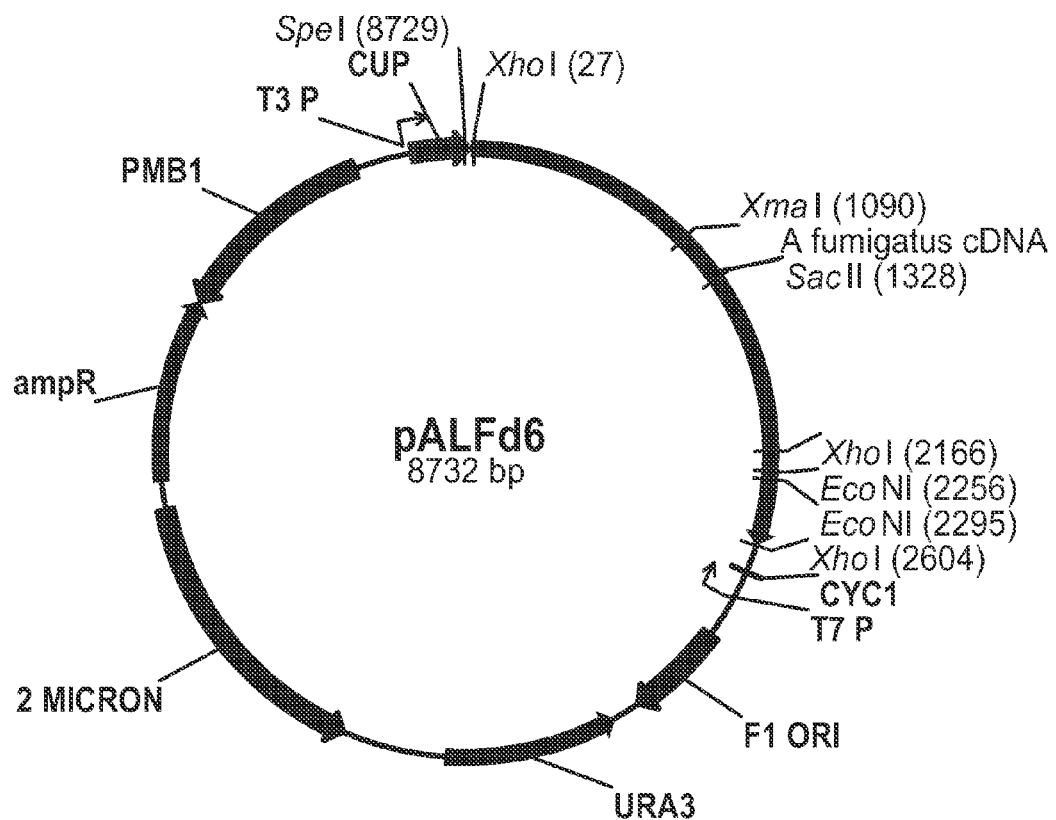
FIG. 21 shows a restriction map of pALFd6.

These colonies turned blue. DNA rescue from one randomly picked blue colony was done as above, the plasmid was transformed into *E. coli* SURE electroporation-competent cells (Stratagene, La Jolla, Ga.) for sequencing. Full-length sequencing indicated the *Aspergillus fumigatus* beta-glucosidase cDNA sequence was correct. This yeast expression vector was designated pALFd6 (FIG. 21), which comprised the *Aspergillus fumigatus* cDNA sequence with its native signal sequence.

Example 19

Expression of *Aspergillus fumigatus* Beta-Glucosidase Comparing Native and Heterologous Secretion Signal in *Saccharomyces cerevisiae*

Plasmids pALFd6 (containing the *Aspergillus fumigatus* with its native signal sequence) and pALFd7 (containing the *Aspergillus fumigatus* with the heterologous signal sequence), approximately 1 μg, were individually transformed into freshly made *Saccharomyces cerevisiae* YNG318 competent cells, plated onto yeast selection plates, and were incubated at 30° C. for 4 days as described in Example 10.

Two blue colonies from both constructs were picked manually and inoculated into yeast selection medium (which contains copper) to induce expression and secretion of *Aspergillus oryzae* beta-glucosidase. Broth from day 5 was then assayed in duplicate for beta-glucosidase activity using p-nitrophenyl-beta-D-glucopyranoside as substrate as described above. Cultures expressing beta-glucosidase with the heterologous signal sequence produced 2.5-fold more beta-glucosidase than cultures expressing beta-glucosidase with its native signal sequence.

DEPOSIT OF BIOLOGICAL MATERIAL

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
|---|---|---|
| *E. coli* TOP10 (pEJG113) | NRRL B-30695 | Oct. 17, 2003 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A nucleic acid construct comprising a nucleotide sequence encoding a signal peptide operably linked to a polynucleotide encoding a polypeptide, wherein the nucleotide sequence encoding the signal peptide is foreign to the polynucleotide encoding the polypeptide, and the 3' end of the nucleotide sequence encoding the signal peptide is immediately upstream of the initiator codon of the polynucleotide encoding the polypeptide; wherein the nucleotide sequence encoding the signal peptide is selected from the group consisting of:
   (i) a nucleotide sequence encoding a signal peptide comprising or consisting of the amino acid sequence of SEQ ID NO: 37; and
   (ii) a nucleotide sequence comprising or consisting of SEQ ID NO: 36.

2. A recombinant expression vector comprising the nucleic acid construct of claim 1.

3. A recombinant host cell comprising the nucleic acid construct of claim 1.

4. The nucleic acid construct of claim 1, wherein the nucleotide sequence encodes a signal peptide comprising the amino acid sequence of SEQ ID NO: 37.

5. The nucleic acid construct of claim 1, wherein the nucleotide sequence encodes a signal peptide consisting of the amino acid sequence of SEQ ID NO: 37.

6. The nucleic acid construct of claim 1, wherein the nucleotide sequence encoding the signal peptide comprises SEQ ID NO: 36.

7. The nucleic acid construct of claim 1, wherein the nucleotide sequence encoding the signal peptide consists of SEQ ID NO: 36.

* * * * *